United States Patent
Mathews et al.

(10) Patent No.: US 9,102,642 B2
(45) Date of Patent: *Aug. 11, 2015

(54) HERBICIDALLY ACTIVE CYCLIC DIONES AND DERIVATIVES THEREOF, PROCESSES FOR THEIR PREPARATION, COMPOSITIONS, AND METHODS OF CONTROLLING WEEDS

(75) Inventors: Christopher John Mathews, Bracknell (GB); John Finney, Bracknell (GB); James Nicholas Scutt, Bracknell (GB); Louisa Robinson, Bracknell (GB); John Stephen Delaney, Bracknell (GB)

(73) Assignee: Syngenta Limited, Guildford, Surrey (GB)

( * ) Notice: Subject to any disclaimer, the term of this patent is extended or adjusted under 35 U.S.C. 154(b) by 99 days.

This patent is subject to a terminal disclaimer.

(21) Appl. No.: 13/147,872

(22) PCT Filed: Jan. 25, 2010

(86) PCT No.: PCT/EP2010/050761
§ 371 (c)(1),
(2), (4) Date: Oct. 14, 2011

(87) PCT Pub. No.: WO2010/089211
PCT Pub. Date: Aug. 12, 2010

(65) Prior Publication Data
US 2012/0021909 A1   Jan. 26, 2012

(30) Foreign Application Priority Data

Feb. 4, 2009   (GB) .................................. 0901835.9

(51) Int. Cl.
| | | |
|---|---|---|
| *C07D 309/32* | (2006.01) | |
| *C07C 49/753* | (2006.01) | |
| *C07D 405/12* | (2006.01) | |
| *C07D 417/12* | (2006.01) | |
| *A01N 43/16* | (2006.01) | |
| *A01N 43/40* | (2006.01) | |
| *A01N 43/42* | (2006.01) | |
| *A01N 43/60* | (2006.01) | |

(52) U.S. Cl.
CPC .............. *C07D 309/32* (2013.01); *A01N 43/16* (2013.01); *A01N 43/40* (2013.01); *A01N 43/42* (2013.01); *A01N 43/60* (2013.01); *C07D 405/12* (2013.01); *C07D 417/12* (2013.01)

(58) Field of Classification Search
USPC ......... 504/121, 124, 128, 137, 238, 241, 242, 504/267, 270, 292, 348; 544/183, 236, 238, 544/278, 318, 354; 546/282.1; 548/170, 548/221; 549/331, 417; 568/315, 327, 329
See application file for complete search history.

(56) References Cited

U.S. PATENT DOCUMENTS

| | | | |
|---|---|---|---|
| 4,175,135 A | 11/1979 | Haines | |
| 4,209,532 A | 6/1980 | Wheeler | |
| 4,409,153 A | 10/1983 | Hodakowski | |
| 4,489,012 A | 12/1984 | Hodakowski | |
| 4,526,723 A | 7/1985 | Wheeler et al. | |
| 4,659,372 A | 4/1987 | Wheeler | |
| 5,502,048 A * | 3/1996 | Chapdelaine et al. | .......... 514/63 |
| 5,801,120 A | 9/1998 | Lee et al. | |
| 6,251,833 B1 | 6/2001 | Erdelen et al. | |
| 6,458,965 B1 | 10/2002 | Lieb et al. | |
| 6,894,005 B1 | 5/2005 | Maetzke et al. | |
| 8,058,210 B2 | 11/2011 | Lieb et al. | |
| 8,084,649 B2 | 12/2011 | Muehlebach et al. | |
| 2003/0216260 A1 | 11/2003 | Ruther et al. | |
| 2006/0166829 A1 | 7/2006 | Fischer et al. | |
| 2010/0113270 A1 | 5/2010 | Mathews et al. | |
| 2010/0210466 A1 | 8/2010 | Muehlebach et al. | |
| 2010/0216638 A1 | 8/2010 | Mathews et al. | |
| 2010/0279868 A1 | 11/2010 | Jeanmart et al. | |
| 2012/0021907 A1 | 1/2012 | Mathews et al. | |

(Continued)

FOREIGN PATENT DOCUMENTS

| | | |
|---|---|---|
| CA | 2322158 A1 | 8/2000 |
| CA | 2325526 A1 | 9/2000 |

(Continued)

OTHER PUBLICATIONS

Muehlebach et al., "Discovery and SAR of pinoxaden: a new broad spectrum, postemergence cereal herbicide," in Pesticide Chemistry. Crop Protection, Public Health, Environmental Safety, ed. H. Ohkawa et al., Jun. 2007, Wiley-VCH Verlag, Weinheim, pp. 101-110.

(Continued)

*Primary Examiner* — Andrew D. Kosar
*Assistant Examiner* — Valerie Rodriguez-Garcia
(74) *Attorney, Agent, or Firm* — R. Kody Jones

(57) ABSTRACT

Compounds of Formula (I), wherein the substituents are as defined in claim 1, are suitable for use as herbicides.

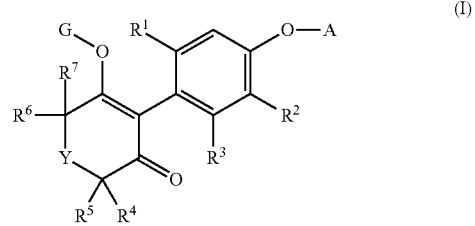

22 Claims, No Drawings

(56) References Cited

U.S. PATENT DOCUMENTS

| | | |
|---|---|---|
| 2012/0021909 A1 | 1/2012 | Mathews et al. |
| 2012/0040826 A1 | 2/2012 | Jeanmart et al. |

FOREIGN PATENT DOCUMENTS

| | | | |
|---|---|---|---|
| CA | 2382432 | A1 | 2/2002 |
| CA | 2382435 | A1 | 2/2002 |
| CA | 2456776 | A1 | 2/2004 |
| DE | 2813341 | C2 | 4/1983 |
| WO | WO 92/16510 | A1 | 10/1992 |
| WO | WO 96/11574 | A1 | 4/1996 |
| WO | WO96/21652 | A1 | 7/1996 |
| WO | WO99/43649 | A1 | 9/1999 |
| WO | WO 99/47525 | A1 | 9/1999 |
| WO | WO99/48869 | A1 | 9/1999 |
| WO | WO 00/37437 | A1 | 6/2000 |
| WO | WO01/17972 | A2 | 3/2001 |
| WO | WO 01/17973 | A2 | 3/2001 |
| WO | WO01/74770 | A1 | 10/2001 |
| WO | WO03/013249 | A1 | 2/2003 |
| WO | WO98/39281 | A1 | 12/2004 |
| WO | WO2004/111042 | A1 | 12/2004 |
| WO | WO 2005/123667 | A1 | 12/2005 |
| WO | WO 2006/034315 | A2 | 3/2006 |
| WO | WO 2006/034446 | A2 | 3/2006 |
| WO | 2008071405 | | 6/2008 |
| WO | WO2008/071405 | A1 | 6/2008 |
| WO | WO2008/110307 | A1 | 9/2008 |
| WO | WO2008/110308 | A2 | 9/2008 |
| WO | 2008145336 | | 12/2008 |
| WO | WO2008/145336 | A1 | 12/2008 |
| WO | WO2009/000533 | A1 | 12/2008 |
| WO | WO2009/015877 | A1 | 2/2009 |
| WO | WO2009/019015 | A1 | 2/2009 |
| WO | WO2009/074314 | A1 | 6/2009 |
| WO | WO2010081755 | A1 | 7/2010 |
| WO | WO2010/089210 | A1 | 8/2010 |
| WO | WO2010/102848 | A1 | 9/2010 |

OTHER PUBLICATIONS

Wenger, J. and Nidermann, T., "Chapter 9: Acetyl-CoA Carboxylase Inhibitors", in Modern Crop Protection Compounds, ed. W. Kraemer et al., Wiley-VCH Verlag, Weinheim, 2007, pp. 335-357.

Wenger, et al., "Chapter 11: Acetyl-CoA Carboxylase Inhibitors", in Modern Crop Protection Compounds, Second Edition, ed. W. Kraemer et al., Wiley-VCH Verlag, Weinheim, available online Jan. 2012, pp. 447-477.

\* cited by examiner

HERBICIDALLY ACTIVE CYCLIC DIONES AND DERIVATIVES THEREOF, PROCESSES FOR THEIR PREPARATION, COMPOSITIONS, AND METHODS OF CONTROLLING WEEDS

This application is a 371 of International Application No. PCT/EP2010/050761 filed Jan. 25, 2010, which claims priority to GB 0901835.9 filed Feb. 4, 2009, the contents of which are incorporated herein by reference.

The present invention relates to novel, herbicidally active cyclic diones, and derivatives thereof, to processes for their preparation, to compositions comprising those compounds, and to their use in controlling weeds, especially in crops of useful plants, or in inhibiting undesired plant growth.

Cyclic diones having herbicidal action are described, for example, in WO08/071,405 and WO08/145,336.

Novel cyclic diones, and derivatives thereof, having herbicidal and growth-inhibiting properties have now been found.

The present invention accordingly relates to compounds of formula I

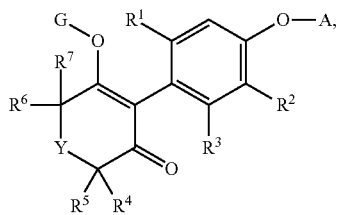

wherein

A is a mono- or bicyclic aryl or heteroaryl which contains a heteroatom selected from nitrogen, oxygen and sulfur, and which is unsubstituted or substituted, $R^1$ is methyl, ethyl, n-propyl, isopropyl, cyclopropyl, halomethyl, haloethyl, vinyl, propenyl, ethynyl, propynyl, halogen, methoxy, ethoxy, halomethoxy or haloethoxy, $R^2$ and $R^3$ are independently of each other hydrogen, methyl, ethyl, n-propyl, isopropyl, cyclopropyl, halomethyl, haloethyl, vinyl, propenyl, ethynyl, propynyl, halogen, methoxy, ethoxy, halomethoxy or haloethoxy, $R^4$, $R^5$, $R^6$ and $R^7$ are independently of each other hydrogen, $C_1$-$C_6$alkyl, $C_1$-$C_6$alkyl substituted by $C_1$-$C_4$alkoxy or halogen, $C_2$-$C_6$ alkenyl, $C_2$-$C_6$ alkenyl substituted by $C_1$-$C_4$alkoxy or halogen, $C_2$-$C_6$alkynyl, $C_2$-$C_6$alkynyl substituted by $C_1$-$C_4$alkoxy or halogen, $C_3$-$C_7$cycloalkyl, $C_3$-$C_7$cycloalkyl substituted by $C_1$-$C_4$alkyl or $C_1$-$C_4$alkoxy, $C_5$-$C_7$cycloalkenyl, $C_5$-$C_7$cycloalkenyl substituted by $C_1$-$C_4$alkyl or $C_1$-$C_4$alkoxy, heterocyclyl or heterocyclyl substituted by $C_1$-$C_4$alkyl or $C_1$-$C_4$alkoxy, or $R^4$ and $R^5$, or $R^6$ and $R^7$, together with the atoms to which they are bonded, form a 5- to 8-membered spiro-carbocyclyl or spiro-heterocyclyl, which contains one or two heteroatoms selected from nitrogen, oxygen or sulfur, or $R^5$ and $R^6$, together with the atoms to which they are bonded, form a 5- to 8-membered carbocyclyl or heterocyclyl, which contains one or two heteroatoms selected from nitrogen, oxygen or sulfur, Y is O, S(O)$_n$, C=O, $CR^8R^9$ or $CR^{10}R^{11}CR^{12}R^{13}$, n is 0, 1 or 2, $R^8$ and $R^9$ are independently of each other hydrogen, $C_1$-$C_6$alkyl, $C_1$-$C_6$alkyl substituted by $C_1$-$C_4$alkoxy or halogen, $C_2$-$C_6$ alkenyl, $C_2$-$C_6$ alkenyl substituted by $C_1$-$C_4$alkoxy or halogen, $C_2$-$C_6$alkynyl, $C_2$-$C_6$alkynyl substituted by $C_1$-$C_4$alkoxy or halogen, $C_3$-$C_7$cycloalkyl, $C_3$-$C_7$cycloalkyl substituted by $C_1$-$C_4$alkyl or $C_1$-$C_4$alkoxy, $C_5$-$C_7$cycloalkenyl, $C_5$-$C_7$cycloalkenyl substituted by $C_1$-$C_4$alkyl or $C_1$-$C_4$alkoxy, heterocyclyl or heterocyclyl substituted by $C_1$-$C_4$alkyl or $C_1$-$C_4$alkoxy, or $R^8$ and $R^9$, together with the atoms to which they are bonded, form a 5- to 8-membered spiro-carbocyclyl or spiro-heterocyclyl, which contains one or two heteroatoms selected from nitrogen, oxygen or sulfur, and $R^{10}$, $R^{11}$, $R^{12}$ and $R^{13}$ are independently of each other hydrogen, $C_1$-$C_6$alkyl or $C_1$-$C_6$alkoxy, and G is hydrogen or an agriculturally acceptable metal, sulfonium, ammonium or latentiating group.

In the substituent definitions of the compounds of the formula I, each alkyl moiety either alone or as part of a larger group (such as alkoxy, alkylthio, alkoxycarbonyl, alkylcarbonyl, alkylaminocarbonyl, dialkylaminocarbonyl) is a straight or branched chain and is, for example, methyl, ethyl, n-propyl, n-butyl, n-pentyl, n-hexyl, isopropyl, n-butyl, sec-butyl, isobutyl, tert-butyl or neopentyl. The alkyl groups are suitably $C_1$-$C_6$alkyl groups, but are preferably $C_1$-$C_4$alkyl or $C_1$-$C_3$alkyl groups, and, more preferably, $C_1$-$C_2$alkyl groups.

Alkenyl and alkynyl moieties can be in the form of straight or branched chains, and the alkenyl moieties, where appropriate, can be of either the (E)- or (Z)-configuration. Examples are vinyl, allyl and propargyl. Alkenyl and alkynyl moieties can contain one or more double and/or triple bonds in any combination. It is understood, that allenyl and alkylinylalkenyl are included in these terms.

Halogen is fluorine, chlorine, bromine or iodine.

Haloalkyl groups are alkyl groups which are substituted with one or more of the same or different halogen atoms and are, for example, $CF_3$, $CF_2Cl$, $CF_2H$, $CCl_2H$, $FCH_2$, $ClCH_2$, $BrCH_2$, $CH_3CHF$, $(CH_3)_2CF$, $CF_3CH_2$ or $CHF_2CH_2$.

In the context of the present specification the term "aryl" refers to ring systems which may be mono- or bicyclic. Examples of such rings include phenyl and naphthyl. A preferred aryl group is phenyl.

The term "heteroaryl" preferably refers to an aromatic ring system containing at least one heteroatom and consisting either of a single ring or of two fused rings. Preferably, single rings will contain up to three and bicyclic systems up to four heteroatoms which will preferably be chosen from nitrogen, oxygen and sulphur. Examples of such groups include furyl, thienyl, pyrrolyl, pyrazolyl, imidazolyl, 1,2,3-triazolyl, 1,2,4-triazolyl, oxazolyl, isoxazolyl, thiazolyl, isothiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyrimidinyl, pyridazinyl, pyrazinyl, 1,2,3-triazinyl, 1,2,4-triazinyl, 1,3,5-triazinyl, benzofuryl, benzisofuryl, benzothienyl, benzisothienyl, indolyl, isoindolyl, indazolyl, benzothiazolyl, benzisothiazolyl, benzoxazolyl, benzisoxazolyl, benzimidazolyl, 2,1,3-benzoxadiazole, quinolinyl, isoquinolinyl, cinnolinyl, phthalazinyl, quinazolinyl, quinoxalinyl, naphthyridinyl, benzotriazinyl, purinyl, pteridinyl and indolizinyl.

The term "heterocyclyl" preferably refers to a non-aromatic preferably monocyclic or bicyclic ring systems containing up to 7 atoms including one or more (preferably one or two) heteroatoms selected from O, S and N. Examples of such rings include tetrahydropyran, 1,3-dioxolane, oxetane, tetrahydrofuran, morpholine, thiomorpholine and piperazine.

Cycloalkyl includes preferably cyclopropyl, cyclobutyl, cyclopentyl and cyclohexyl. Cycloalkylalkyl is preferentially cyclopropylmethyl. Cycloalkenyl includes preferably cyclopentenyl and cyclohexenyl.

Carbocyclic rings include aryl, cycloalkyl or carbocyclic groups, and cycloalkenyl groups.

When present, the optional substituents on aryl, heteroaryl and carbocycles are preferably selected independently, from halogen, nitro, cyano, rhodano, isothiocyanato, $C_1$-$C_6$alkyl, $C_1$-$C_6$haloalkyl, $C_1$-$C_6$alkoxy($C_1$-$C_6$) alkyl, $C_2$-$C_6$alkenyl, $C_2$-$C_6$haloalkenyl, $C_2$-$C_6$alkynyl, $C_3$-$C_7$cycloalkyl (itself optionally substituted with $C_1$-$C_6$alkyl or halogen), $C_{5-7}$cycloalkenyl (itself optionally substituted with $C_1$-$C_6$alkyl or halogen), hydroxy, $C_1$-$C_{10}$alkoxy, $C_1$-$C_{10}$alkoxy($C_1$-$C_{10}$) alkoxy, tri($C_1$-$C_4$)alkylsilyl($C_1$-$C_6$)alkoxy, $C_1$-$C_6$alkoxycarbonyl($C_1$-$C_{10}$)alkoxy, $C_1$-$C_{10}$haloalkoxy, aryl($C_1$-$C_4$)alkoxy (where the aryl group is optionally substituted with halogen or $C_1$-$C_6$alkyl), $C_3$-$C_7$cycloalkyloxy (where the cycloalkyl group is optionally substituted with $C_1$-$C_6$alkyl or halogen), $C_3$-$C_{10}$alkenyloxy, $C_3$-$C_{10}$alkynyloxy, mercapto, $C_1$-$C_{10}$alkylthio, $C_1$-$C_{10}$haloalkylthio, aryl($C_1$-$C_4$)alkylthio, $C_3$-$C_7$cycloalkylthio (where the cycloalkyl group is optionally substituted with $C_1$-$C_6$alkyl or halogen), tri($C_1$-$C_4$)alkylsilyl($C_1$-$C_6$)alkylthio, arylthio, $C_1$-$C_6$alkylsulfonyl, $C_1$-$C_6$haloalkylsulfonyl, $C_1$-$C_6$alkylsulfinyl, $C_1$-$C_6$haloalkylsulfinyl, arylsulfonyl, tri($C_1$-$C_4$)alkylsilyl, aryldi($C_1$-$C_4$)alkylsilyl, $C_1$-$C_4$alkyldiarylsilyl, triarylsilyl, $C_1$-$C_{10}$alkylcarbonyl, $HO_2C$, $C_1$-$C_{10}$alkoxycarbonyl, aminocarbonyl, $C_1$-$C_6$alkylaminocarbonyl, di($C_1$-$C_6$alkyl)-aminocarbonyl, N—($C_1$-$C_3$ alkyl)-N—($C_1$-$C_3$alkoxy)aminocarbonyl, $C_1$-$C_6$alkylcarbonyloxy, arylcarbonyloxy, di($C_1$-$C_6$)alkylaminocarbonyloxy, aryl (itself optionally substituted with $C_1$-$C_6$alkyl or halogen), heteroaryl (itself optionally substituted with $C_1$-$C_6$alkyl or halogen), heterocyclyl (itself optionally substituted with $C_1$-$C_6$alkyl or halogen), aryloxy (where the aryl group is optionally substituted with $C_1$-$C_6$alkyl or halogen), heteroaryloxy (where the heteroaryl group is optionally substituted with $C_1$-$C_6$alkyl or halogen), heterocyclyloxy (where the heterocyclyl group is optionally substituted with $C_1$-$C_6$alkyl or halogen), amino, $C_1$-$C_6$alkylamino, di($C_1$-$C_6$)alkylamino, $C_1$-$C_6$alkylcarbonylamino, N—($C_1$-$C_6$)alkylcarbonyl-N—($C_1$-$C_6$)alkylamino, arylcarbonyl, (where the aryl group is itself optionally substituted with halogen or $C_1$-$C_6$alkyl) or two adjacent positions on an aryl or heteroaryl system may be cyclised to form a 5, 6 or 7 membered carbocyclic or heterocyclic ring, itself optionally substituted with halogen or $C_1$-$C_6$alkyl. Further substituents for aryl or heteroaryl include arylcarbonylamino (where the aryl group is substituted by $C_1$-$C_6$alkyl or halogen), ($C_1$-$C_6$)alkoxycarbonylamino, ($C_1$-$C_6$)alkoxycarbonyl-N—($C_1$-$C_6$)alkylamino, aryloxycarbonylamino (where the aryl group is substituted by $C_1$-$C_6$alkyl or halogen), aryloxycarbonyl-N—($C_1$-$C_6$)alkylamino, (where the aryl group is substituted by $C_1$-$C_6$alkyl or halogen), arylsulphonylamino (where the aryl group is substituted by $C_1$-$C_6$alkyl or halogen), arylsulphonyl-N—($C_1$-$C_6$)alkylamino (where the aryl group is substituted by $C_1$-$C_6$alkyl or halogen), aryl-N—($C_1$-$C_6$)alkylamino (where the aryl group is substituted by $C_1$-$C_6$alkyl or halogen), arylamino (where the aryl group is substituted by $C_1$-$C_6$alkyl or halogen), heteroaryl amino (where the heteroaryl group is substituted by $C_1$-$C_6$alkyl or halogen), heterocyclylamino (where the heterocyclyl group is substituted by $C_1$-$C_6$alkyl or halogen), aminocarbonylamino, $C_1$-$C_6$alkylaminocarbonylamino, di($C_1$-$C_6$)alkylaminocarbonylamino, arylaminocarbonylamino where the aryl group is substituted by $C_1$-$C_6$alkyl or halogen), aryl-N—($C_1$-$C_6$)alkylaminocarbonylamino where the aryl group is substituted by $C_1$-$C_6$alkyl or halogen), $C_1$-$C_6$alkylaminocarbonyl-N—($C_1$-$C_6$)alkylamino, di($C_1$-$C_6$)alkylaminocarbonyl-N—($C_1$-$C_6$)alkylamino, arylaminocarbonyl-N—($C_1$-$C_6$)alkylamino where the aryl group is substituted by $C_1$-$C_6$alkyl or halogen) and aryl-N—($C_1$-$C_6$)alkylaminocarbonyl-N—($C_1$-$C_6$)alkylamino where the aryl group is substituted by $C_1$-$C_6$alkyl or halogen).

The invention relates also to the agriculturally acceptable salts which the compounds of formula I are able to form with transition metal, alkali metal and alkaline earth metal bases, amines, quaternary ammonium bases or tertiary sulfonium bases.

Among the transition metal, alkali metal and alkaline earth metal salt formers, special mention should be made of the hydroxides of copper, iron, lithium, sodium, potassium, magnesium and calcium, and preferably the hydroxides, bicarbonates and carbonates of sodium and potassium.

Examples of amines suitable for ammonium salt formation include ammonia as well as primary, secondary and tertiary $C_1$-$C_{18}$alkylamines, $C_1$-$C_4$hydroxyalkylamines and $C_2$-$C_4$alkoxyalkyl-amines, for example methylamine, ethylamine, n-propylamine, isopropylamine, the four butylamine isomers, n-amylamine, isoamylamine, hexylamine, heptylamine, octylamine, nonylamine, decylamine, pentadecylamine, hexadecylamine, heptadecylamine, octadecylamine, methylethylamine, methylisopropylamine, methylhexylamine, methylnonylamine, methylpentadecylamine, methyloctadecylamine, ethylbutylamine, ethylheptylamine, ethyloctylamine, hexylheptylamine, hexyloctylamine, dimethylamine, diethylamine, di-n-propylamine, di-isopropylamine, di-n-butylamine, di-n-amylamine, di-isoamylamine, dihexylamine, diheptylamine, dioctylamine, ethanolamine, n-propanolamine, isopropanolamine, N,N-diethanolamine, N-ethylpropanolamine, N-butylethanolamine, allylamine, n-but-2-enylamine, n-pent-2-enylamine, 2,3-dimethylbut-2-enylamine, dibut-2-enylamine, n-hex-2-enylamine, propylenediamine, trimethylamine, triethylamine, tri-n-propylamine, tri-isopropylamine, tri-n-butylamine, tri-isobutylamine, tri-sec-butylamine, tri-n-amylamine, methoxyethylamine and ethoxyethylamine; heterocyclic amines, for example pyridine, quinoline, isoquinoline, morpholine, piperidine, pyrrolidine, indoline, quinuclidine and azepine; primary arylamines, for example anilines, methoxyanilines, ethoxyanilines, o-, m- and p-toluidines, phenylenediamines, benzidines, naphthylamines and o-, m- and p-chloroanilines; but especially triethylamine, isopropylamine and di-isopropylamine.

Preferred quaternary ammonium bases suitable for salt formation correspond, for example, to the formula $[N(R_a R_b R_c R_d)]OH$, wherein $R_a$, $R_b$, $R_c$ and $R_d$ are each independently of the others hydrogen, $C_1$-$C_4$alkyl. Further suitable tetraalkylammonium bases with other anions can be obtained, for example, by anion exchange reactions.

Preferred tertiary sulfonium bases suitable for salt formation correspond, for example, to the formula $[SR_e R_f R_g]OH$, wherein $R_e$, $R_f$ and $R_g$ are each independently of the others $C_1$-$C_4$ alkyl. Trimethylsulfonium hydroxide is especially preferred. Suitable sulfonium bases may be obtained from the reaction of thioethers, in particular dialkylsulfides, with alkylhalides, followed by conversion to a suitable base, for example a hydroxide, by anion exchange reactions.

It should be understood that in those compounds of formula I, where G is a metal, ammonium or sulfonium as mentioned above and as such represents a cation, the corresponding negative charge is largely delocalised across the O—C=C—C=O unit.

The compounds of formula I according to the invention also include hydrates which may be formed during the salt formation.

The latentiating groups G are selected to allow its removal by one or a combination of biochemical, chemical or physical processes to afford compounds of formula I where G is H before, during or following application to the treated area or plants. Examples of these processes include enzymatic cleavage, chemical hydrolysis and photoloysis. Compounds bearing such groups G may offer certain advantages, such as improved penetration of the cuticula of the plants treated, increased tolerance of crops, improved compatibility or stability in formulated mixtures containing other herbicides, herbicide safeners, plant growth regulators, fungicides or insecticides, or reduced leaching in soils.

The latentiating group G is preferably selected from the groups $C_1$-$C_8$alkyl, $C_2$-$C_8$haloalkyl, phenyl$C_1$-$C_8$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano or by nitro), heteroaryl$C_1$-$C_8$alkyl (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), $C_3$-$C_8$alkenyl, $C_3$-$C_8$haloalkenyl, $C_3$-$C_8$alkynyl, $C(X^a)$—$R^a$, $C(X^b)$—$X^c$—$R^b$, $C(X^d)$—$N(R^c)$—$R^d$, —$SO_2$—$R^e$, —$P(X^f)(R^f)$—$R^g$ or $CH_2$—$X^f$—$R^h$ wherein $X^a$, $X^b$, $X^c$, $X^d$, $X^e$ and $X^f$ are independently of each other oxygen or sulfur;

$R^a$ is H, $C_1$-$C_{18}$alkyl, $C_2$-$C_{18}$alkenyl, $C_2$-$C_{18}$alkynyl, $C_1$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_3$—($C_1$-$C_5$)oxyalkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_1$-$C_5$)alkylamino($C_1$-$C_5$)alkyl, $C_3$-$C_6$trialkylsilyl($C_1$-$C_5$)alkyl, phenyl($C_1$-$C_5$)alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl($C_1$-$C_5$)alkyl, (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroaryl or heteroaryl substituted by $C_1$-$C_3$ alkyl, $C_1$-$C_3$haloalkyl, $C_1$-$C_3$alkoxy, $C_1$-$C_3$haloalkoxy, halogen, cyano or nitro, $R^b$ is $C_1$-$C_{18}$alkyl, $C_3$-$C_{18}$alkenyl, $C_3$-$C_{18}$alkynyl, $C_2$-$C_{18}$haloalkyl, $C_1$-$C_{10}$cyanoalkyl, $C_1$-$C_{10}$nitroalkyl, $C_2$-$C_{18}$-aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_1$-$C_5$)alkylamino($C_1$-$C_5$)alkyl, $C_3$-$C_6$trialkylsilyl($C_1$-$C_5$)alkyl, phenyl($C_1$-$C_5$)alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl, (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkyl-thio, $C_1$-$C_3$alkylsulfinyl, $C_1$-$C_3$alkylsulfonyl, halogen, cyano, or by nitro), $C_3$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroaryl or heteroaryl substituted by $C_1$-$C_3$ alkyl, $C_1$-$C_3$haloalkyl, $C_1$-$C_3$alkoxy, $C_1$-$C_3$haloalkoxy, halogen, cyano or nitro, $R^c$ and $R^d$ are each independently of each other hydrogen, $C_1$-$C_{10}$alkyl, $C_3$-$C_{10}$alkenyl, $C_3$-$C_{10}$alkynyl, $C_2$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$) alkyl, $C_1$-$C_5$alkoxy($C_1$-$C_5$)alkyl, $C_3$-$C_5$alkenyloxy($C_1$-$C_5$) alkyl, $C_3$-$C_5$alkynyloxy($C_1$-$C_5$)alkyl, $C_1$-$C_5$alkylthio($C_1$-$C_5$) alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_2$-$C_5$)alkylaminoalkyl, $C_3$-$C_6$trialkylsilyl($C_1$-$C_5$)alkyl, phenyl($C_1$-$C_5$)alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl($C_1$-$C_5$)alkyl, (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroaryl or heteroaryl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroarylamino or heteroarylamino substituted by $C_1$-$C_3$alkyl, $C_1$-$C_3$haloalkyl, $C_1$-$C_3$alkoxy, $C_1$-$C_3$haloalkoxy, halogen, cyano or nitro, diheteroarylamino or diheteroarylamino substituted by $C_1$-$C_3$alkyl, $C_1$-$C_3$haloalkyl, $C_1$-$C_3$alkoxy, $C_1$-$C_3$haloalkoxy, halogen, cyano or nitro, phenylamino or phenylamino substituted by $C_1$-$C_3$alkyl, $C_1$-$C_3$haloalkyl, $C_1$-$C_3$alkoxy, $C_1$-$C_3$haloalkoxy, halogen, cyano or by nitro, diphenylamino or diphenylamino substituted by $C_1$-$C_3$alkyl, $C_1$-$C_3$haloalkyl, $C_1$-$C_3$alkoxy, $C_1$-$C_3$haloalkoxy, halogen, cyano or by nitro or $C_3$-$C_7$cycloalkylamino, di-$C_3$-$C_7$cycloalkylamino or $C_3$-$C_7$cycloalkoxy or $R^c$ and $R^d$ may join together to form a 3-7 membered ring, optionally containing one heteroatom selected from O or S, $R^e$ is $C_1$-$C_{10}$alkyl, $C_2$-$C_{10}$alkenyl, $C_2$-$C_{10}$alkynyl, $C_1$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_1$-$C_5$)alkylamino($C_1$-$C_5$)alkyl, $C_3$-$C_6$trialkylsilyl($C_1$-$C_5$)alkyl, phenyl($C_1$-$C_5$)alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl($C_1$-$C_5$)alkyl (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or by nitro, heteroaryl or heteroaryl substituted by $C_1$-$C_3$alkyl, $C_1$-$C_3$haloalkyl, $C_1$-$C_3$alkoxy, $C_1$-$C_3$haloalkoxy, halogen, cyano or by nitro, heteroarylamino or heteroarylamino substituted by $C_1$-$C_3$ alkyl, $C_1$-$C_3$haloalkyl, $C_1$-$C_3$alkoxy, $C_1$-$C_3$haloalkoxy, halogen, cyano or by nitro, diheteroarylamino or diheteroarylamino substituted by $C_1$-$C_3$alkyl, $C_1$-$C_3$haloalkyl, $C_1$-$C_3$alkoxy, $C_1$-$C_3$haloalkoxy, halogen, cyano or nitro, phenylamino or phenylamino substituted by $C_1$-$C_3$alkyl, $C_1$-$C_3$haloalkyl, $C_1$-$C_3$alkoxy, $C_1$-$C_3$haloalkoxy, halogen, cyano or nitro, diphenylamino, or diphenylamino substituted by $C_1$-$C_3$alkyl, $C_1$-$C_3$haloalkyl, $C_1$-$C_3$alkoxy, $C_1$-$C_3$alkoxy, $C_1$-$C_3$haloalkoxy, halogen, cyano or nitro, or $C_3$-$C_7$cycloalkylamino, di$C_3$-$C_7$cycloalkylamino or $C_3$-$C_7$cycloalkoxy, $C_1$-$C_{10}$alkoxy, $C_1$-$C_{10}$haloalkoxy, $C_1$-$C_5$alkylamino or $C_2$-$C_8$dialkylamino, $R^f$ and $R^g$ are each independently of each other $C_1$-$C_{10}$alkyl, $C_2$-$C_{10}$alkenyl, $C_2$-$C_{10}$alkynyl, $C_1$-$C_{10}$alkoxy, $C_1$-$C_{10}$haloalkyl, $C_1$-$C_{10}$cyanoalkyl, $C_1$-$C_{10}$nitroalkyl, $C_1$-$C_{10}$-aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_2$-$C_5$)alkylaminoalkyl, $C_3$-$C_6$trialkylsilyl($C_1$-$C_5$)alkyl, phenyl($C_1$-$C_5$)alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl($C_1$-$C_5$)alkyl (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroaryl or heteroaryl substituted by $C_1$-$C_3$ alkyl, $C_1$-$C_3$haloalkyl, $C_1$-$C_3$alkoxy, $C_1$-$C_3$haloalkoxy, halogen, cyano or by nitro, heteroarylamino or heteroarylamino substituted by $C_1$-$C_3$ alkyl, $C_1$-$C_3$haloalkyl, $C_1$-$C_3$alkoxy, $C_1$-$C_3$haloalkoxy, halogen, cyano or by nitro, diheteroarylamino or diheteroarylamino substituted by $C_1$-$C_3$ alkyl, $C_1$-$C_3$haloalkyl, $C_1$-$C_3$alkoxy, $C_1$-$C_3$haloalkoxy, halogen, cyano or nitro, phenylamino or phenylamino substituted by $C_1$-$C_3$alkyl, $C_1$-$C_3$haloalkyl, $C_1$-$C_3$alkoxy, $C_1$-$C_3$haloalkoxy, halogen, cyano or nitro, diphenylamino, or diphenylamino substituted by $C_1$-$C_3$alkyl, $C_1$-$C_3$haloalkyl, $C_1$-$C_3$alkoxy, $C_1$-$C_3$haloalkoxy, halogen, cyano or nitro, or $C_3$-$C_7$cycloalkylamino, di$C_3$-$C_7$cycloalkylamino or $C_3$-$C_7$cycloalkoxy, $C_1$-$C_{10}$haloalkoxy, $C_1$-$C_5$alkylamino or $C_2$-$C_8$dialkylamino, benzyloxy or phenoxy, wherein the benzyl and phenyl groups may in turn be substituted by $C_1$-$C_3$alkyl, $C_1$-$C_3$haloalkyl, $C_1$-$C_3$alkoxy, $C_1$-$C_3$haloalkoxy, halogen, cyano or nitro, and $R^h$ is $C_1$-$C_{10}$alkyl, $C_3$-$C_{10}$alkenyl, $C_3$-$C_{10}$alkynyl, $C_1$-$C_{10}$haloalkyl, $C_1$-$C_{10}$cyanoalkyl, $C_1$-$C_{10}$nitroalkyl, $C_2$-$C_{18}$-aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_1$-$C_5$)alkylamino($C_1$-$C_5$)alkyl, $C_3$-$C_6$trialkylsilyl($C_1$-$C_5$)alkyl, phenyl($C_1$-$C_5$)alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), heteroaryl($C_1$-$C_5$)alkyl (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), phenoxy($C_1$-$C_5$)alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), heteroaryloxy($C_1$-$C_5$)alkyl (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), $C_3$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen or by nitro, or heteroaryl, or heteroaryl substituted by $C_1$-$C_3$alkyl, $C_1$-$C_3$haloalkyl, $C_1$-$C_3$alkoxy, $C_1$-$C_3$haloalkoxy, halogen, cyano or by nitro.

In particular, the latentiating group G is a group —C($X^a$)—$R^a$ or —C($X^b$)—$X^c$—$R^b$, and the meanings of $X^a$, $R^a$, $X^b$, $X^c$ and $R^b$ are as defined above.

It is preferred that G is hydrogen, an alkali metal or alkaline earth metal, where hydrogen is especially preferred.

Depending on the nature of the substituents, compounds of formula I may exist in different isomeric forms. For example, when G is hydrogen and $R^4$ and $R^5$ are different from $R^6$ and $R^7$, compounds of formula I may exist in different tautomeric forms:

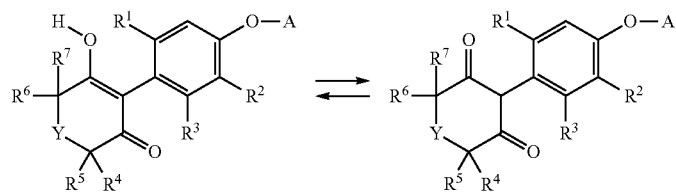
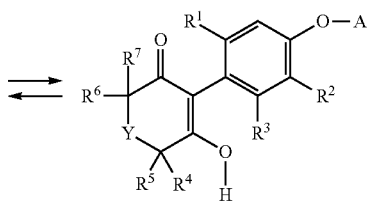

This invention covers all such isomers and tautomers and mixtures thereof in all proportions. Also, when substituents contain double bonds, cis- and trans-isomers can exist. These isomers, too, are within the scope of the claimed compounds of the formula I.

Preferably, in the compounds of formula I, A is phenyl, naphthyl, a 5- or 6-membered heteroaryl or a bicyclic 8- to 10-membered heteroaryl.

Preferably, in the compounds of formula I, A is substituted by halogen, $C_1$-$C_4$alkyl, $C_1$-$C_4$haloalkyl, $C_2$-$C_4$alkenyl, $C_2$-$C_4$haloalkenyl, $C_2$-$C_4$alkynyl, $C_1$-$C_4$alkoxy, $C_1$-$C_4$haloalkoxy, $C_1$-$C_4$alkylthio, $C_1$-$C_4$alkylsulfinyl, $C_1$-$C_4$alkylsulfonyl, $C_1$-$C_4$haloalkylthio, $C_1$-$C_4$haloalkylsulfinyl, $C_1$-$C_4$haloalkylsulfonyl, nitro, cyano, $C_3$-$C_6$cycloalkyl, $C_1$-$C_3$alkylcarbonyl, $C_1$-$C_4$alkoxycarbonyl, aminocarbonyl, $C_1$-$C_3$alkylaminocarbonyl, di-$C_1$-$C_3$alkylaminocarbonyl, $C_1$-$C_3$alkylaminocarbonyloxy, di-$C_1$-$C_3$alkylaminocarbonyloxy, aminothiocarbonyl, $C_1$-$C_3$alkylaminothiocarbonyl, di$C_1$-$C_3$alkylaminothiocarbonyl, $C_1$-$C_4$alkylcarbonylamino, $C_3$-$C_6$cycloalkylcarbonylamino, $C_1$-$C_4$alkoxycarbonylamino, $C_1$-$C_4$alkylthiocarbonylamino, $C_1$-$C_3$alkoxy$C_1$-$C_3$alkyl, $C_1$-$C_6$alkylthio$C_1$-$C_6$alkyl, $C_1$-$C_6$alkylsulfinyl$C_1$-$C_6$alkyl, $C_1$-$C_6$alkylsulfonyl$C_1$-$C_6$alkyl, $C_1$-$C_3$alkylsulfonyloxy, $C_1$-$C_3$haloalkylsulfonyloxy or di$C_1$-$C_6$alkylaminosulfonyl, or 2 substituents on adjacent carbon atoms of A together form a $C_3$-$C_4$alkylene, wherein 1 or 2 methylene groups are optionally substituted by halogen, or wherein 1 or 2 of these methylene groups are replaced by oxygen.

More preferably, A is phenyl, naphthyl, pyridyl, pyrazinyl, pyrimidinyl, pyridazinyl, benzothiazolyl, benzoxazolyl, cinnolinyl, quinolinyl, quinazolinyl, quinoxalinyl or benzotriazinyl in each case substituted by halogen, methyl, ethyl, trifluoromethyl, methoxy, difluoromethoxy, trifluoromethoxy, nitro or cyano.

$R^1$ is preferably methyl, ethyl, n-propyl, cyclopropyl, halogen, halomethoxy or haloethoxy, especially methyl or ethyl.

Preferably, $R^2$ is hydrogen, methyl or halogen, especially hydrogen.

Preferably, $R^3$ is hydrogen, methyl, ethyl, n-propyl, cyclopropyl, halogen, halomethoxy or haloethoxy, especially hydrogen, methyl or ethyl.

Preferably, $R^4$, $R^5$, $R^6$ and $R^7$ are independently of each other hydrogen or $C_1$-$C_6$alkyl, or $R^4$ and $R^5$, or $R^6$ and $R^7$, together with the atoms to which they are bonded form a spiro-tetrahydropyranyl or spiro-tetrahydrofuranyl, or $R^5$ and $R^6$ together with the atoms to which they are bonded form a 6- or 7-membered carbocyclyl.

Preferably, Y is O or $CR^8R^9$, where $R^8$ and $R^9$ are as defined above.

Preferably, $R^8$ and $R^9$ are independently of each other hydrogen or methyl, or $R^8$ and $R^9$ together with the atoms to which they are bonded form a spiro-tetrahydropyranyl or a spiro-tetrahydrofuranyl.

Preferably, G is hydrogen, a group —C($X^a$)—$R^a$ or —C($X^b$)—$X^c$—$R^b$, where the meanings of $X^a$, $R^a$, $X^b$, $X^c$ and $R^b$ are as defined above, and particularly hydrogen.

In a particularly preferred group of compounds of formula I A is phenyl, naphthyl, pyridyl, pyrazinyl, pyrimidinyl, pyridazinyl, benzothiazolyl, benzoxazolyl, cinnolinyl, quinolinyl, quinazolinyl, quinoxalinyl or benzotriazinyl, in each case substituted by halogen, methyl, trifluoromethyl, nitro or cyano, $R^1$ is ethyl, $R^2$ and $R^3$ are hydrogen, $R^4$ to $R^7$ are hydrogen or methyl or $R^5$ and $R^6$, together with the atoms to which they are bonded, form a 6- or 7-membered carbocyclyl, Y is O or $CR^8R^9$, wherein $R^8$ and $R^9$ are independently of each other hydrogen or methyl, or $R^8$ and $R^9$ together with the atoms to which they are bonded form a spiro-tetrahydropyranyl or a spiro-tetrahydrofuranyl, and G is hydrogen.

A compound of formula I wherein Q is $Q_1$ and G is $C_1$-$C_8$alkyl, $C_2$-$C_8$haloalkyl, phenyl$C_1$-$C_8$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsufinyl, $C_1$-$C_3$alkylsulfonyl, halogen, cyano or by nitro), heteroaryl$C_1$-$C_8$alkyl (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsufinyl, $C_1$-$C_3$alkylsulfonyl, halogen, cyano or by nitro), $C_3$-$C_8$alkenyl, $C_3$-$C_8$haloalkenyl, $C_3$-$C_8$alkynyl, C($X^a$)—$R^a$, C($X^b$)—$X^c$—$R^b$, C($X^d$)—N($R^c$)—$R^d$, —$SO_2$—$R^e$, —P($X^e$)($R^f$)—$R^g$ or $CH_2$—$X^f$—$R^h$ where $X^a$, $X^b$, $X^c$, $X^d$, $X^e$, $X^f$, $R^a$, $R^b$, $R^c$, $R^d$, $R^e$, $R^f$, $R^g$ and $R^h$ are as defined above may be prepared by treating a compound of formula (A), which is a compound of formula I wherein G is H, with a reagent G-Z, wherein G-Z is an alkylating agent such as an alkyl halide (the definition of alkyl halides includes simple $C_1$-$C_8$ alkyl halides such as methyl iodide and ethyl iodide, substituted alkyl halides such as chloromethyl alkyl ethers, Cl—$CH_2$—$X^f$—$R^h$, wherein $X^f$ is oxygen, and chloromethyl alkyl sulfides Cl—$CH_2$—$X^f$—$R^h$, wherein $X^f$ is sulfur), a $C_1$-$C_8$alkyl sulfonate, or a di($C_1$-$C_8$alkyl) sulfate, or with a $C_3$-$C_8$alkenyl halide, or with a $C_3$-$C_8$alkynyl halide, or with an acylating agent such as a carboxylic acid, HO—C($X^a$)$R^a$, wherein $X^a$ is oxygen, an acid chloride, Cl—C($X^a$)$R^a$, wherein $X^a$ is oxygen, or acid anhydride, [$R^aC(X^a)$]$_2$O, wherein $X^a$ is oxygen, or an isocyanate, $R^c$N=C=O, or a carbamoyl chloride, Cl—C($X^d$)—N($R^c$)—$R^d$ (wherein $X^d$ is oxygen and with the proviso that neither $R^c$ or $R^d$ is hydrogen), or a thiocarbamoyl chloride Cl—($X^d$)—N($R^c$)—$R^d$ (wherein $X^d$ is sulfur and with the proviso that neither $R^c$ or $R^d$ is hydrogen) or a chloroformate, Cl—C($X^b$)—$X^c$—$R^b$, (wherein $X^b$ and $X^c$ are oxygen), or a chlorothioformate Cl—C($X^b$)—$X^c$—$R^b$ (wherein $X^b$ is oxygen and $X^c$ is sulfur), or a chlorodithioformate Cl—C($X^b$)—$X^c$—$R^b$, (wherein $X^b$ and $X^c$ are sulfur), or an isothiocyanate, $R^c$N=C=S, or by sequential treatment with carbon disulfide and an alkylating agent, or with a phosphorylating agent such as a phosphoryl chloride, Cl—P($X^e$)($R^f$)—$R^g$ or with a sulfonylating agent such as a sulfonyl chloride Cl—$SO_2$—$R^e$, preferably in the presence of at least one equivalent of base.

Where substituents R⁴ and R⁵ are not equal to substituents R⁶ and R⁷, these reactions may produce, in addition to a compound of formula I, a second compound of formula I₄.

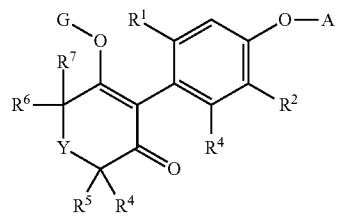

Formula I

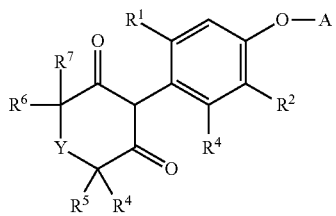

Formula (A)

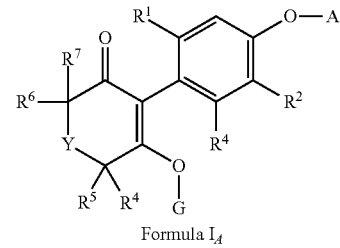

Formula I₄

This invention covers both a compound of formula I and a compound of formula I₄, together with mixtures of these compounds in any ratio.

The O-alkylation of cyclic 1,3-diones is known; suitable methods are described, for example, by T. Wheeler, U.S. Pat. No. 4,436,666. Alternative procedures have been reported by M. Pizzorno and S. Albonico, Chem. Ind. (London), (1972), 425-426; H. Born et al., J. Chem. Soc., (1953), 1779-1782; M. G. Constantino et al., Synth. Commun., (1992), 22 (19), 2859-2864; Y. Tian et al., Synth. Commun., (1997), 27 (9), 1577-1582; S. Chandra Roy et al., Chem. Letters, (2006), 35 (1), 16-17; P. K. Zubaidha et al., Tetrahedron Lett., (2004), 45, 7187-7188.

The O-acylation of cyclic 1,3-diones may be effected by procedures similar to those described, for example, by R. Haines, U.S. Pat. No. 4,175,135, and by T. Wheeler, U.S. Pat. Nos. 4,422,870, 4,659,372 and 4,436,666. Typically diones of formula (A) may be treated with an acylating agent preferably in the presence of at least one equivalent of a suitable base, and optionally in the presence of a suitable solvent. The base may be inorganic, such as an alkali metal carbonate or hydroxide, or a metal hydride, or an organic base such as a tertiary amine or metal alkoxide. Examples of suitable inorganic bases include sodium carbonate, sodium or potassium hydroxide, sodium hydride, and suitable organic bases include trialkylamines, such as trimethylamine and triethylamine, pyridines or other amine bases such as 1,4-diazobicyclo[2.2.2]-octane and 1,8-diazabicyclo[5.4.0]undec-7-ene. Preferred bases include triethylamine and pyridine. Suitable solvents for this reaction are selected to be compatible with the reagents and include ethers such as tetrahydrofuran and 1,2-dimethoxyethane and halogenated solvents such as dichloromethane and chloroform. Certain bases, such as pyridine and triethylamine, may be employed successfully as both base and solvent. For cases where the acylating agent is a carboxylic acid, acylation is preferably effected in the presence of a known coupling agent such as 2-chloro-1-methylpyridinium iodide, N,N'-dicyclohexylcarbodiimide, 1-(3-dimethylaminopropyl)-3-ethylcarbodiimide and N,N'-carbodiimidazole, and optionally in the presence of a base such as triethylamine or pyridine in a suitable solvent such as tetrahydrofuran, dichloromethane or acetonitrile. Suitable procedures are described, for example, by W. Zhang and G. Pugh, Tetrahedron Lett., (1999), 40 (43), 7595-7598; T. Isobe and T. Ishikawa, J. Org. Chem., (1999), 64 (19), 6984-6988 and K. Nicolaou, T. Montagnon, G. Vassilikogiannakis, C. Mathison, J. Am. Chem. Soc., (2005), 127(24), 8872-8888.

Phosphorylation of cyclic 1,3-diones may be effected using a phosphoryl halide or thiophosphoryl halide and a base by procedures analogous to those described by L. Hodakowski, U.S. Pat. No. 4,409,153.

Sulfonylation of a compound of formula (A), may be achieved using an alkyl or aryl sulfonyl halide, preferably in the presence of at least one equivalent of base, for example by the procedure of C. Kowalski and K. Fields, J. Org. Chem., (1981), 46, 197-201.

Compounds of formula (A), wherein Y is $S(O)_n$ and n is 1 or 2 may be prepared from compounds of formula (A) wherein Y is S by oxidation, according to a procedure analogous to that of E. Fehnel and A. Paul, J. Am. Chem. Soc., (1955), 77, 4241-4244.

A compound of formula (A), wherein Y is O, S, C═O or $CR^{12}R^{13}$ may be prepared via the cyclisation of a compound of formula (B), preferably in the presence of an acid or base, and optionally in the presence of a suitable solvent, by analogous methods to those described by T. Wheeler, U.S. Pat. No. 4,209,532. The compounds of the formula (B) have been particularly designed as intermediates in the synthesis of the compounds of the formula I. Compounds of formula (B) wherein R is hydrogen or $C_1$-$C_4$alkyl, (especially methyl, ethyl and tert-butyl) may be cyclised under acidic conditions, preferably in the presence of a strong acid such as sulfuric acid, polyphosphoric acid or Eaton's reagent, optionally in the presence of a suitable solvent such as acetic acid, toluene or dichloromethane.

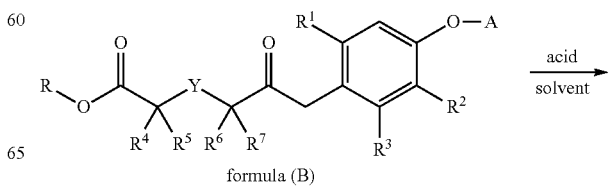

formula (B)

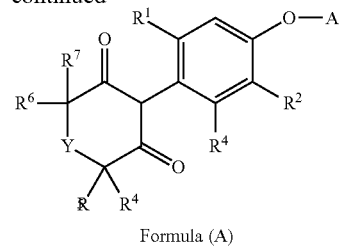

Formula (A)

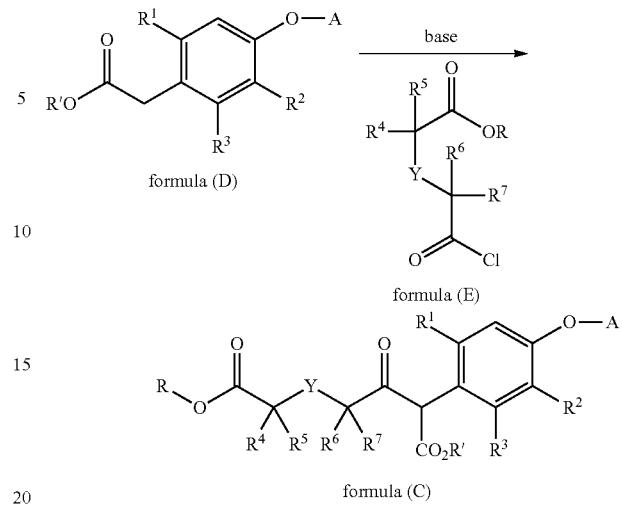

formula (D)

formula (E)

formula (C)

A compound of formula (B) wherein R is alkyl (preferably methyl or ethyl) may be cyclised under acidic or basic conditions, preferably under basic conditions in the presence of at least one equivalent of a strong base such as potassium tert-butoxide, lithium diisopropylamide, sodium bis(trimethylsilyl)amide or sodium hydride and in a solvent such as tetrahydrofuran, toluene, dimethylsulfoxide or N,N-dimethylformamide.

A compound of formula (B), wherein R is H may be esterified to a compound of formula (B), wherein R is alkyl, under known conditions (for example by treatment with an alcohol, R—OH, in the presence of an acid catalyst).

A compound of formula (B), wherein R is H may be prepared by hydrolysis of a compound of formula (C) wherein R is H or alkyl and R' is alkyl (preferably methyl or ethyl), followed by acidification of the reaction mixture to effect decarboxylation, by similar processes to those described by, for example, T. Wheeler, U.S. Pat. No. 4,209,532. Alternatively, a compound of formula (B), wherein R is alkyl (preferably methyl) may be prepared from a compound of formula (C), wherein R is alkyl (preferably methyl), through a Krapcho decarboxylation procedure under known conditions using known reagents (see for example G. Quallich, P. Morrissey, Synthesis, (1993), (1), 51-53).

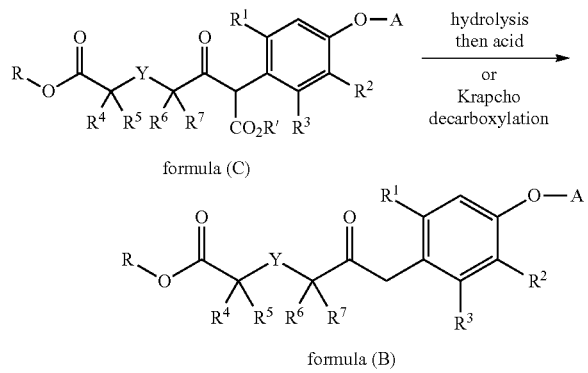

formula (C)

formula (B)

A compound of formula (C) wherein R is alkyl may be prepared by treating a compound of formula (D) with a suitable carboxylic acid chloride of formula (E) wherein R is alkyl under basic conditions. Suitable bases include potassium tert-butoxide, sodium bis(trimethylsilyl)amide and lithium diisopropylamide and the reaction is preferably conducted in a suitable solvent (such as tetrahydrofuran or toluene) at a temperature of between −80° C. and 30° C.:

Alternatively, a compound of formula (C), wherein R is H, may be prepared by treating a compound of formula (D) with a suitable base (such as potassium tert-butoxide, sodium bis(trimethylsilyl)amide and lithium diisopropylamide) in a suitable solvent (such as tetrahydrofuran or toluene) at a suitable temperature (between −80° C. and 30° C.) and reacting the resulting anion with a suitable anhydride of formula (F):

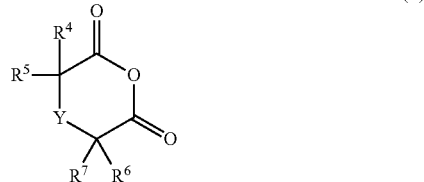

formula (F)

Compounds of formula (E) and formula (F) are known, or may be made by similar methods from commercially available starting materials (see, for example C. Rouvier, Tetrahedron Lett., (1984), (39), 4371-4374; D. Walba and M. Wand, Tetrahedron Lett., (1982), 23 (48), 4995-4998; T. Terasawa and T. Okada, J. Org. Chem., (1977), 42 (7), 1163-1169 and G. Bennett, W. Houlihan, R. Mason, and R. Engstrom, J. Med. Chem., (1976), 19 (5), 709-714; J. Cason, Org. Synth. Coll. Vol. IV, (1963), 630-633).

Compounds of formula (D) are known (see, for example, P. Ple and F. Jung, WO06/040520; M. He et al., WO05/021554; Y. Kohno et al., WO03/029184; W. Marshall, U.S. Pat. No. 3,649,679; M. Ryozo et al., Chem. Pharm. Bull., (1983), 31 (10), 3424-3445) or may be made by similar methods from known compounds.

In a further approach, a compound of formula (A) may be prepared by reacting a compound of formula (G) with a with an aryllead tricarboxylate, in the presence of a suitable ligand and in a suitable solvent. Similar reactions are described in the literature (for example see, M. Muehlebach et al., WO08/071,405; J. Pinhey, B. Rowe, Aust. J. Chem., (1979), 32, 1561-6; J. Morgan, J. Pinhey, J. Chem. Soc. Perkin Trans. 1, (1990), 3, 715-20). Preferably the aryllead tricarboxylate is an aryllead triacetate of formula (H). Preferably the ligand is a nitrogen containing heterocycle such as N,N-dimethylaminopyridine, 1,10-phenanthroline pyridine, bipyridine, or imidazole, and one to ten equivalents of ligand with respect to a compound of formula (J) is preferably used. Most preferably the ligand is N,N-dimethylaminopyridine. The solvent is preferably chloroform, dichloromethane or toluene, most preferably chloroform, or a mixture of chloroform and toluene. Preferably the reaction is conducted at a temperature of −10° C. to 100° C., most preferably at 40-90° C.).

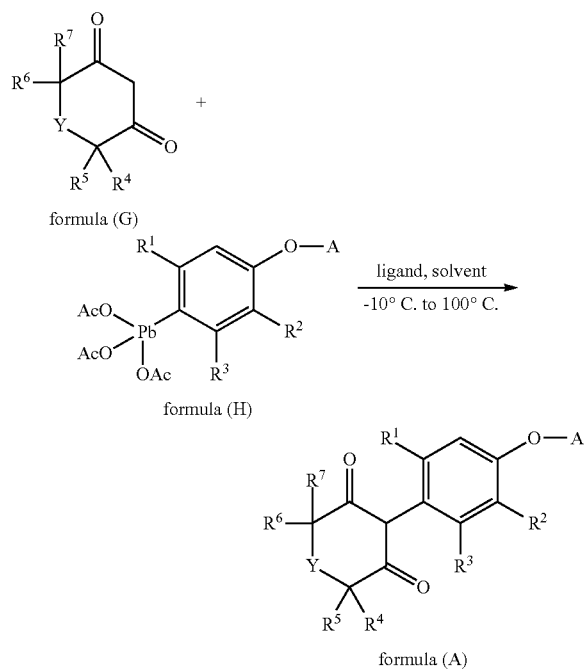

Compounds of formula (G), wherein Y is O, are known compounds or may be prepared by routes analogous to those described in the literature (see, for example, M. Muehlebach et al., WO08/071,405; M. Morgan and E. Heyningen, J. Am. Chem. Soc., (1957), 79, 422-424; I. Korobitsyna and K. Pivnitskii, Russian Journal of General Chemistry, (1960), 30, 4016-4023; T. Terasawa, and T. Okada, J. Org. Chem., (1977), 42 (7), 1163-1169; R. Anderson et al. U.S. Pat. No. 5,089,046; R. Altenbach, K. Agrios, I. Drizin and W. Carroll, Synth. Commun., (2004), 34 (4) 557-565; R. Beaudegnies et al., WO2005/123667; W. Li, G. Wayne, J. Lallaman, S. Chang, and S. Wittenberger, J. Org. Chem. (2006), 71, 1725-1727; R. Altenbach, M. Brune, S. Buckner, M. Coghlan, A. Daza, A. Fabiyi, M. Gopalakrishnan, R. Henry, A. Khilevich, M. Kort, I. Milicic, V. Scott, J. Smith, K. Whiteaker, and W. Carroll, J. Med. Chem., (2006), 49(23), 6869-6887; Carroll et al., WO 2001/083484 A1; J. K. Crandall, W. W. Conover, J. Org. Chem. (1978), 43(18), 3533-5; I. K. Korobitsyna, O. P. Studzinskii, Chemistry of Heterocyclic Compounds (1966), (6), 848-854). Compounds of formula (G), wherein Y is S, are known compounds or may be prepared by routes analogous to those described in the literature (see, for example, E. Fehnel and A. Paul, J. Am. Chem. Soc., (1955), 77, 4241-4244; E. Er and P. Margaretha, Helvetica Chimica Acta (1992), 75(7), 2265-69; H. Gayer et al., DE 3318648 A1). Compounds of formula (G), wherein Y is C=O, are known compounds or may be prepared by routes analogous to those described in the literature (see, for example, R. Götz and N. Götz, WO2001/060776 R. Götz et al. WO 2000/075095; M. Benbakkar et al., Synth. Commun. (1989) 19(18) 3241-3247; A. Jain and T. Seshadri, Proc. Indian Acad. Sci. Sect. A, (1955), 42, 279); N. Ahmad et al., J. Org. Chem., (2007), 72(13), 4803-4815); F. Effenberger et al., Chem. Ber., (1986), 119, 3394-3404 and references therein). Compounds of formula (G), wherein Y is $CR^{12}R^{13}$ are known compounds of may be prepared by routes analogous to those described in the literature (see for example, M. Muehlebach et al., WO08/110,307; M. Muehlebach et al., WO08/110,308; S. Spessard and B. Stoltz, Organic Letters, (2002), Vol. 4, No. 11, 1943-1946; F. Effenberger et al., Chem. Ber., (1984), 117, 3280-3296; W. Childers et al., Tetrahedron Lett., (2006), 2217-2218; W. Childers et al., US2006/0004108; H. Schneider and C. Luethy, EP1352890; D. Jackson, A. Edmunds, M. Bowden and B. Brockbank, WO2005/105745 and WO2005/105717; R. Beaudegnies, C. Luethy, A. Edmunds, J. Schaetzer and S. Wendeborn, WO2005/123667; J-C. Beloeil, J-Y. Lallemand, T. Prange, Tetrahedron, (1986), Vol. 42. No. 13, 3491-3502; G. Stork and R. Danheiser, J. Org. Chem., (1973), 38 (9), 1775-1776; H. Favre et al., Can. J. Chem. (1956), 34 1329-39; R. Shriner and H. Todd, Org. Synth. Coll. Vol. II, (1943), 200-202).

A compound of formula (H) may be prepared from a compound of formula (I) by treatment with lead tetraacetate in a suitable solvent (for example chloroform) at 25° C. to 100° C. (preferably 25-50° C.), and optionally in the presence of a catalyst such as mercury diacetate, according to procedures described in the literature (for example see, K. Shimi, G. Boyer, J-P. Finet and J-P. Galy, Letters in Organic Chemistry, (2005), 2, 407-409; J. Morgan and J. Pinhey, J. Chem. Soc. Perkin Trans. 1; (1990), 3, 715-720).

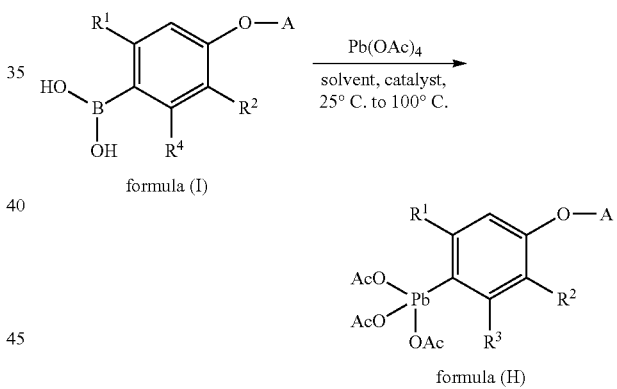

An aryl boronic acid of formula (I) may be prepared from an aryl halide of formula (J), wherein Hal is bromine or iodine by known methods (see, for example, W. Thompson and J. Gaudino, J. Org. Chem., (1984), 49, 5237-5243 and R. Hawkins et al., J. Am. Chem. Soc., (1960), 82, 3053-3059). Thus an aryl halide of formula (J) may be treated with an alkyl lithium or alkyl magnesium halide at low temperature, and the aryl magnesium or aryl lithium reagent obtained is allowed to react with a trialkyl borate, $B(OR'')_3$, preferably trimethylborate, to give an aryl dialkylboronate which may be hydrolysed to the desired boronic acid of formula (I) under acidic conditions. Alternatively the same overall transformation of compound (J) to compound (I) may be achieved through a palladium-catalysed borylation reaction under known conditions using known reagents (see for example T. Ishiyama, M. Murata, N. Miyaura, J. Org. Chem. (1995), 60, 7508-7501; and K. L. Billingsley, T. E. Barder, S. L. Buchwald, Angew. Chem. Int. Ed. (2007), 46, 5359-5363), followed by hydrolysis of the intermediate boronate ester.

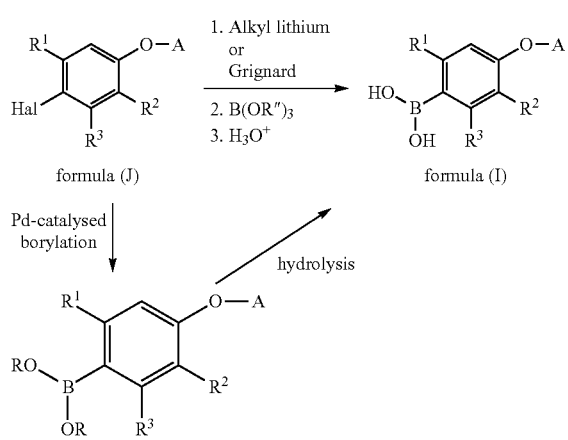

Aryl halides of formula (J) are known compounds or may be made by known methods from known compounds (See, for example, R. Trust et al., J. Med. Chem., (1979), 22 (9), 1068-1074).

In a further approach, a compound of formula (A) may be prepared by cross-coupling an aryl halide of formula (K), wherein Hal is bromine or iodine, with a phenol, A-OH, in the presence of a suitable catalyst, optionally a suitable ligand or additive, a suitable base and a suitable solvent, under conditions similar to those described, for example, by S. Hu et al., J. Org. Chem., (2008), 73, 7814-7817; P. Chan et al., Tetrahedron Lett., (2008), 49, 2018-2022); R. Hosseinzadeh et al., Synthetic Commun., (2008) 38, 3023-3031; S. Buchwald et al., J. Am. Chem. Soc., (2006), 128, 10694-10695; H. Rao et al., Chem. Eur. J., (2006), 12, 3636-3646; M. Taillefer et al., Adv. Synth. Catal. (2006), 348, 499-505; M. Beller et al., Tetrahedron Lett., (2005), 46 (18), 3237-3240; M. Taillefer et al., Org. Lett. (2004), 6 (6), 913; D. Ma and Q. Cai, Org. Lett. (2003), 5 (21), 3799-3802; J. Song et al., Org. Lett. (2002), 4 (9), 1623-1626; R. Venkataraman et al., Org. Lett. (2001), 3 (26), 4315-4317; S. Buchwald et al., J. Am. Chem. Soc. (1999), 121, 4369-4378; S. Buchwald et al., J. Am. Chem. Soc., (1997), 119, 10539-10540; G. Mann and J. Hartwig, Tetrahedron Lett., (1997), 38 (46), 8005-8008.

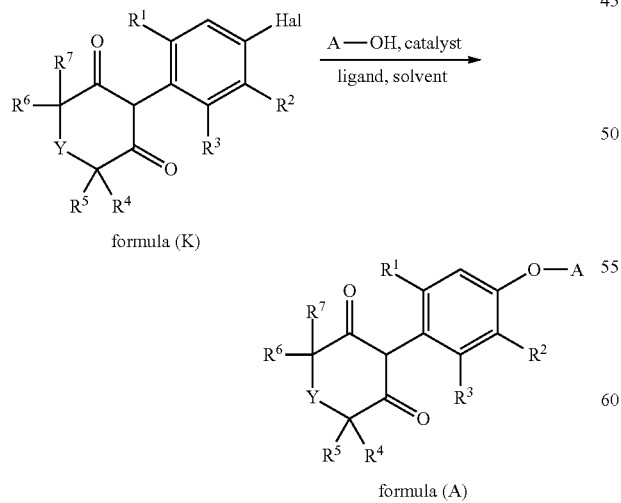

Suitable catalysts include palladium and copper catalysts such as palladium(II) acetate, bis(dibenzylideneacetone)palladium(II), copper powder, copper(II) acetate, copper(I) chloride, copper(I) bromide, copper(II) bromide, copper(I) iodide, copper(I) oxide, copper(II) sulfate, copper(I) trifluoromethanesulfonate and copper(II) trifluoromethanesulfonate. Optionally the catalysts are used in conjunction with appropriate ligands or additives, such as N-methylglycine N,N-dimethylglycine, 1-butylimidazole, ethyl acetate, ethylene glycol diacetate, 8-hydroxyquinoline, L-proline, 1-naphthoic acid, triphenylphosphine, 1,1'-bis(diphenylphosphino)ferrocene, salicylaldoxime, 2-(N,N-dimethylamino)-2'-di-tert-butylphosphinobiphenyl, neocuproine, pyrrolidine-2-phosphionic acid phenyl monoester, 2,2,6,6-tetramethylheptane-3,5-dione, tetrabutylammonium bromide, 2,2-bipyridine or 1,10-phenanthroline. Suitable bases are cesium carbonate, cesium fluoride, potassium fluoride, potassium phosphate and sodium hydroxide. Suitable solvents are acetonitrile, N,N,-dimethylformamide, 1,4-dioxane or toluene, or mixed solvent systems such as toluene/tetrahydrofuran and 1,4-dioxane/water.

The use of copper(I) iodide and copper(II) trifluoromethanesulfonate catalysts is preferred.

A compound of formula (K) may be prepared according to procedures similar to those described by M. Muehlebach et al., WO08/071,405. For example, a compound of formula (K) may be prepared from a compound of formula (G) by reaction with a compound of formula (L) under conditions similar to those used for the preparation of a compound of formula (A) from a compound of formula (G).

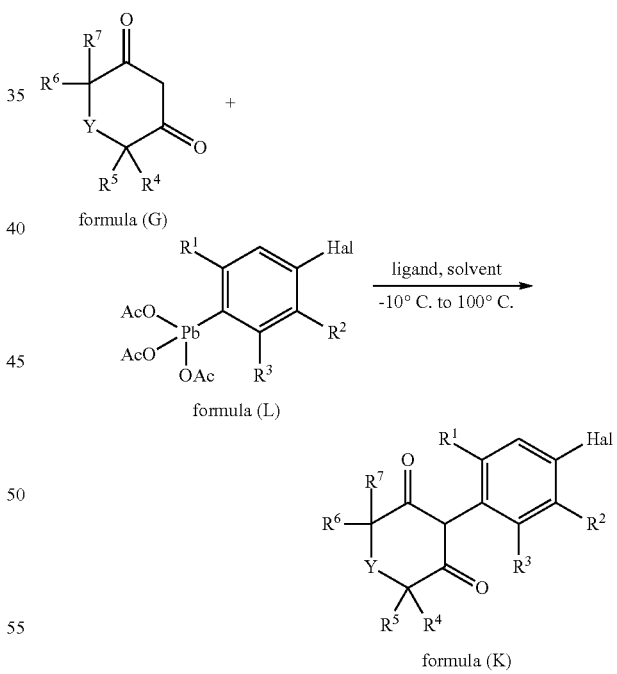

In a further approach, a compound of formula (A) may be prepared by reacting a compound of formula (M) with an aryl halide of formula A-Hal, wherein Hal represents fluorine, chlorine, bromine or iodine. When A-Hal is an aryl bromide or aryl iodide, the reaction may be effected using suitable copper or palladium catalysts under conditions described previously for the preparation of a compound of formula (A) from a compound of formula (K).

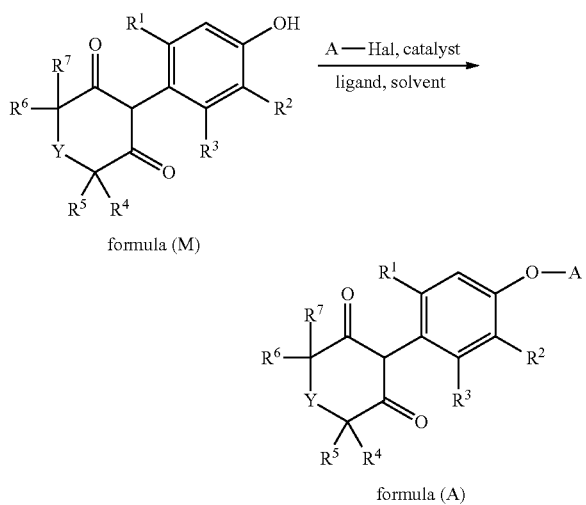

formula (M)

formula (A)

Alternatively, when A-Hal is a suitably electron-deficient aryl halide (for example an aryl fluororide or aryl chloride additionally bearing one or more electron-withdrawing substituents such as trifluoromethyl, nitro or cyano), or a suitable heteroaryl halide (for example a halopyridine, halopyrimidine, or other electron-deficient heteroaryl halide) the reaction may be effected in the presence of a suitable base such as potassium carbonate or cesium carbonate, without the need for a catalyst and a ligand.

A compound of formula (M) may be prepared from a compound of formula (K). In one approach, a compound of formula (K) is deprotonated with a base (such as a Grignard reagent or alkyllithium reagent), and then treated with an alkyllithium reagent to effect metal-halogen exchange. The resulting organometallic species may then be converted into a compound of formula (M) either by treatment with a trialkylborate such as trimethyl borate followed by oxidation (for example by hydrogen peroxide, N-methyl morpholine N-oxide or oxone) as described, for example by G. Prakash et al., J. Org. Chem., (2001), 66 (2), 633-634; J-P Gotteland and S Halazy, Synlett. (1995), 931-932; K. Webb and D. Levy, Tetrahedron Lett., (1995), 36 (29), 5117-5118. In an alternative approach, a compound of formula (M) may be prepared from a compound of formula (K) by treatment with an aqueous solution of an alkali metal hydroxide in the presence of a suitable catalyst and a suitable ligand, according to known procedures. For example, a compound of formula (M) may be prepared by treating a compound of formula (K) with potassium hydroxide in the presence of a palladium catalyst (for example bis(dibenzylidene-acetone)palladium(II), and in the presence of a suitable phosphine ligand such as 2-(di-tert-butylphosphino)-2',4',6'-triisopropylbiphenyl and 2-(di-tert-butylphosphino)-3,4,5,6-tetramethyl-2',4',6'-triisopropylbiphenyl, under conditions described, for example, by S. Buchwald et al., J. Am. Chem. Soc., (2006), 128, 10694-10695. Alternatively, a compound of formula (M) may be prepared by treating a compound of formula (K) treatment with an aqueous solution of sodium hydroxide in the presence of a suitable copper catalyst (for example copper(I) iodide) and a suitable ligand (such as L-proline), under conditions described, for example, by C. Kormos and N. Leadbeater, Tetrahedron (2006), 62 (19), 4728-4732.

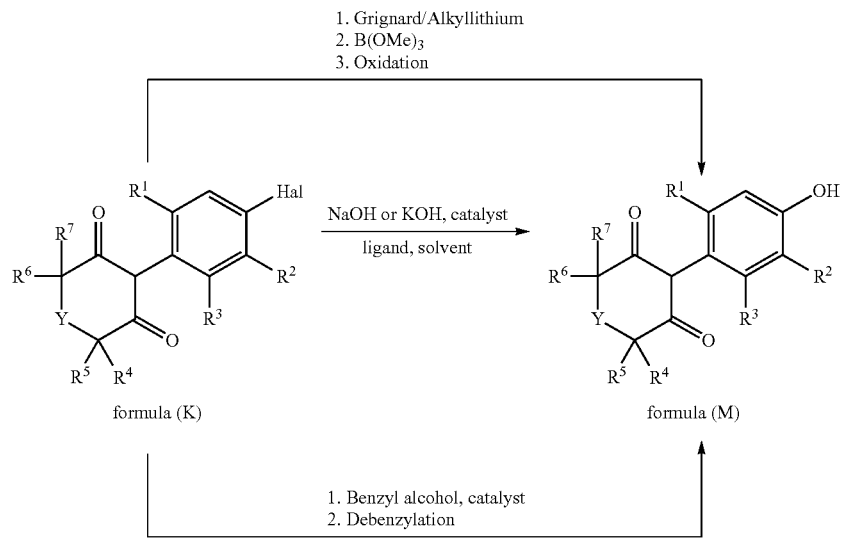

In a third approach to a compound of formula (M) a compound of formula (K) may be treated with a benzyl alcohol in the presence of a suitable copper catalyst, followed by debenzylation under known conditions (for example by catalytic hydrogenolysis).

The compounds of the formula (M) are novel and have been especially designed as intermediates for the synthesis of the compounds of formula I.

In an alternative approach, a compound of formula (A) may be prepared by the reaction of a compound of formula (N), wherein Ar is an aryl moiety (preferably phenyl) with an arylboronic acid of formula (I) in the presence of a suitable palladium catalyst, a suitable base, an optionally in the presence of a suitable ligand or additive, and in a suitable solvent.

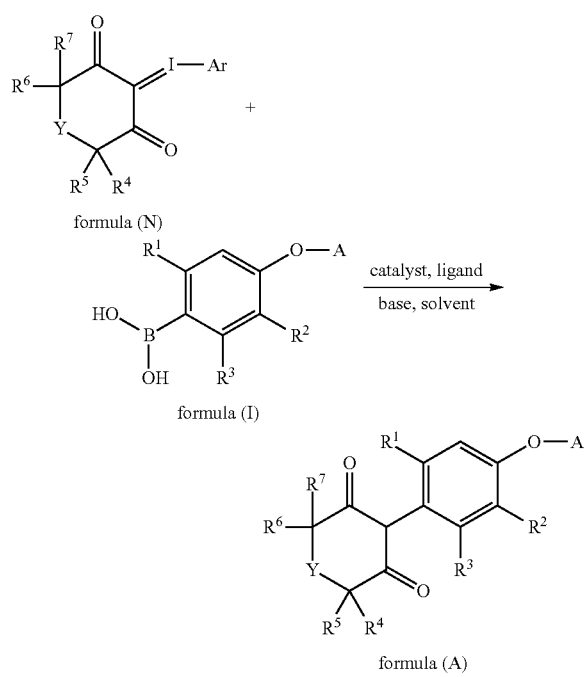

formula (N)

formula (I)

formula (A)

Suitable palladium catalysts include, for example palladium(II) dihalides, palladium(II) acetate and palladium(II) sulfate, and is preferably palladium(II) acetate. Suitable ligands include triphenyl-phosphine, tricyclopentylphosphine, tricyclohexylphosphine, 2-dicyclo-hexylphosphino-2',6'-dimethoxybiphenyl, 2-dicyclohexylphosphino-2',4',6'-triisopropyl-biphenyl, 1,1'-bis(diphenyl-phosphino)ferrocene and 1,2-bis(diphenylphosphino)ethane. The reaction may also be carried out in the presence of other additives, such as tetralkylammonium salts, for example, tetrabutylammonium bromide. Suitable bases include alkali metal hydroxides, especially lithium hydroxide. A suitable solvent is aqueous 1,2-dimethoxyethane.

A compound of Formula (N), wherein Ar is phenyl, may be prepared from a compound of Formula (G) by treatment with a hypervalent iodine reagent such as a (diacetoxy)iodobenzene or iodosylbenzene and a base such as aqueous sodium carbonate, lithium hydroxide or sodium hydroxide in a solvent such as water or an aqueous alcohol such as aqueous ethanol according to the procedures of K. Schank and C. Lick, Synthesis (1983), 392; R. Moriarty et al, J. Am. Chem. Soc, (1985), 107, 1375, or of Z. Yang et al., Org. Lett., (2002), 4 (19), 3333:

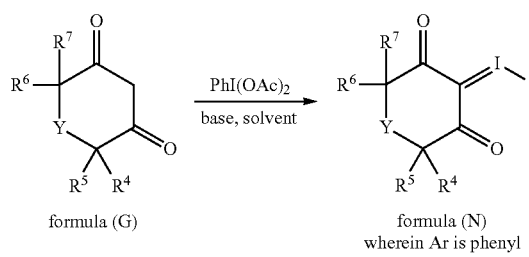

formula (G)

formula (N) wherein Ar is phenyl

In a further approach, a compound of formula I may be prepared by reacting a compound of formula (O) (wherein G is preferably $C_{1-4}$ alkyl, and Hal is a halogen, preferably bromine or iodine), with an arylboronic acid of formula (I) in the presence of a suitable palladium catalyst (for example 0.001-50% palladium(II) acetate with respect to compound (O)) and a base (for example 1 to 10 equivalents potassium phosphate with respect to compound (O)) and preferably in the presence of a suitable ligand (for example 0.001-50% (2-dicyclohexylphosphino)-2',6'-dimethoxybiphenyl with respect to compound (U)), and in a suitable solvent (for example toluene), preferably between 25° C. and 200° C. Similar couplings are known in the literature (see for example, Y. Song, B. Kim and J.-N. Heo, Tetrahedron Letters (2005), 46 (36), 5987-5990).

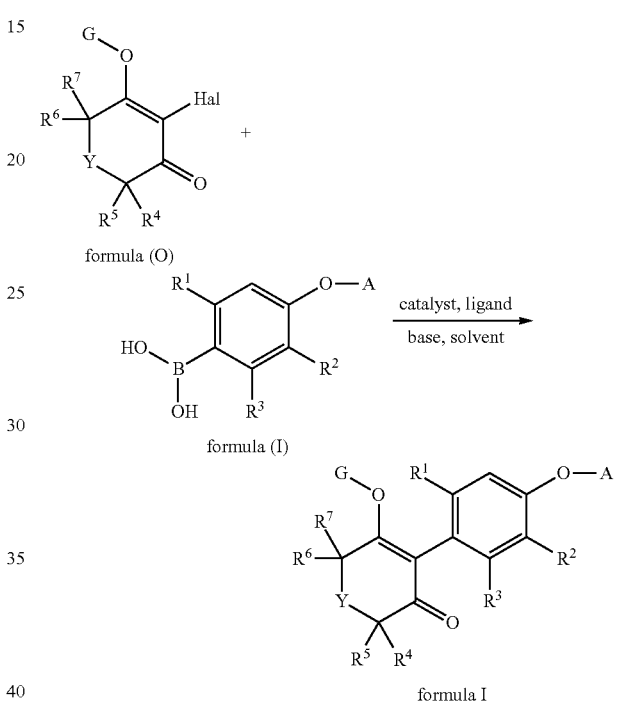

formula (O)

formula (I)

formula I

A compound of formula (O) may be prepared by halogenating a compound of formula (G), followed by reaction of the resulting halide of formula (O) with a $C_1$-$C_4$ alkyl halide or tri-$C_1$-$C_4$-alkylorthoformate under known conditions, for example by the procedures of R. Shepherd and A. White (J. Chem. Soc. Perkin Trans. 1 (1987), 2153-2155) and Y.-L. Lin et al. (Bioorg. Med. Chem. (2002), 10, 685-690). Alternatively, a compound of formula (O) may be prepared by reacting a compound of formula (G) with a $C_1$-$C_4$alkyl halide or a tri-$C_1$-$C_4$-alkylorthoformate, and halogenating the resulting enone of formula (R) under known conditions (see for example Y. Song, B. Kim and J.-N. Heo, Tetrahedron Letters (2005), 46(36), 5987-5990).

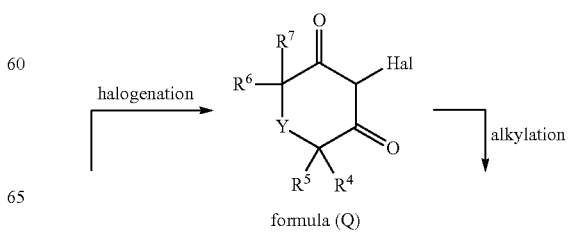

formula (Q)

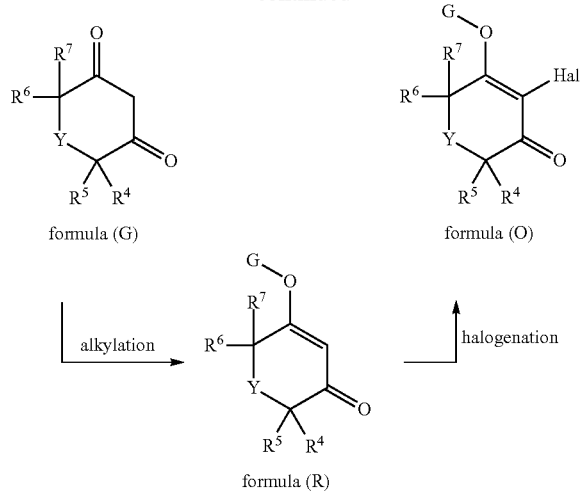

formula (G)

formula (O)

alkylation → formula (R) ← halogenation

In a further approach, a compound of formula (A) may be prepared by reacting a compound of formula (G) with a compound of formula (J) in the presence of a suitable palladium catalyst (for example 0.001-50% palladium(II) acetate with respect to compound (G)) and a base (for example 1 to 10 equivalents potassium phosphate with respect to compound (G)) and preferably in the presence of a suitable ligand (for example 0.001-50% (2-dicyclohexylphosphino)-2',4',6'-triisopropylbiphenyl with respect to compound (G)), and in a suitable solvent (for example dioxane), preferably between 25° C. and 200° C. and optionally under microwave heating.

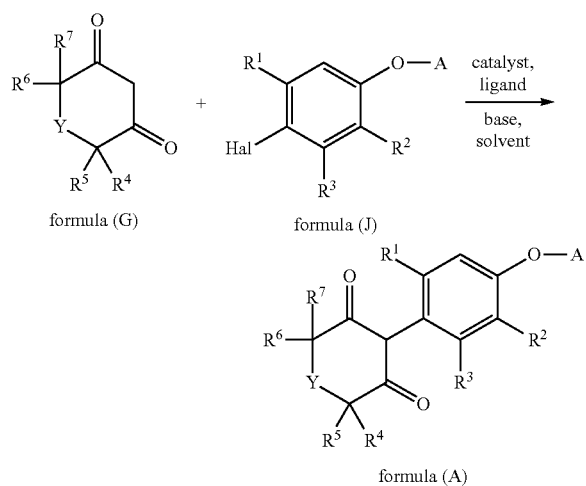

formula (G) + formula (J) → formula (A)

Similar couplings are known in the literature (see for example, S. Buchwald et al., J. Am. Chem. Soc. (2000), 122, 1360-1370; B. Hong et al. WO 2005/000233). Alternatively, a compound of formula (A) may be prepared by reacting a compound of formula (J) with a compound of formula (M) in the presence of a suitable copper catalyst (for example 0.001-50% copper(I) iodide with respect to compound (J)) and a base (for example 1 to 10 equivalents cesium carbonate with respect to compound (J)) and preferably in the presence of a suitable ligand (for example 0.001-50% L-proline with respect to compound (J)), and in a suitable solvent (for example dimethylsulfoxide), preferably between 25° C. and 200° C. Similar couplings are known in the literature (see for example, Y. Jiang et al., Synlett, (2005), 18, 2731-2734, and X. Xie et al., Organic Letters (2005), 7(21), 4693-4695).

The compounds of formula I according to the invention can be used as crop protection agents in unmodified form, as obtained in the synthesis, but they are generally formulated into crop protection compositions in a variety of ways using formulation adjuvants, such as carriers, solvents and surface-active substances. The formulations can be in various physical forms, for example in the form of dusting powders, gels, wettable powders, coated or impregnated granules for manual or mechanical distribution on target sites, water-dispersible granules, water-soluble granules, emulsifiable granules, water-dispersible tablets, effervescent compressed tablets, water-soluble tapes, emulsifiable concentrates, microemulsifiable concentrates, oil-in-water (EW) or water-in-oil (WO) emulsions, other multiphase systems such as oil/water/oil and water/oil/water products, oil flowables, aqueous dispersions, oily dispersions, suspoemulsions, capsule suspensions, soluble liquids, water-soluble concentrates (with water or a water-miscible organic solvent as carrier), impregnated polymer films or in other forms known, for example, from the Manual on Development and Use of FAO Specifications for Plant Protection Products, 5th Edition, 1999. The active ingredient may be incorporated into microfibers or microrods formed of polymers or polymerizable monomers and having diameter of about 0.1 to about 50 microns and aspect ratio of between about 10 and about 1000.

Such formulations can either be used directly or are diluted prior to use. They can then be applied through suitable ground or aerial application spray equipment or other ground application equipment such as central pivot irrigation systems or drip/trickle irrigation means. Diluted formulations can be prepared, for example, with water, liquid fertilisers, micronutrients, biological organisms, oil or solvents.

The formulations can be prepared, for example, by mixing the active ingredient with formulation adjuvants in order to obtain compositions in the form of finely divided solids, granules, solutions, dispersions or emulsions. The active ingredients can also be contained in fine microcapsules consisting of a core and a polymeric shell. Microcapsules usually have a diameter of from 0.1 to 500 microns. They contain active ingredients in an amount of about from 25 to 95% by weight of the capsule weight. The active ingredients can be present in the form of liquid technical material, in the form of a suitable solution, in the form of fine particles in solid or liquid dispersion or as a monolithic solid. The encapsulating membranes comprise, for example, natural and synthetic gums, cellulose, styrene-butadiene copolymers or other similar suitable membrane forming material, polyacrylonitrile, polyacrylate, polyester, polyamides, polyureas, polyurethane, aminoplast resins or chemically modified starch or other polymers that are known to the person skilled in the art in this connection.

Alternatively it is possible for fine so called "microcapsules" to be formed wherein the active ingredient is present in the form of finely divided particles in a solid matrix of a base substance, but in that case the microcapsule is not encapsulated with a diffusion limiting membrane as outlined in the preceding paragraph.

The active ingredients may be adsorbed on a porous carrier. This may enable the active ingredients to be released into their surroundings in controlled amounts (e.g. slow release). Other forms of controlled release formulations are granules or powders in which the active ingredient is dispersed or dissolved in a solid matrix consisting of a polymer, a wax or a suitable solid substance of lower molecular weight. Suitable polymers are polyvinyl acetates, polystyrenes, polyolefins, polyvinyl alcohols, polyvinyl pyrrolidones, alkylated polyvinyl pyrrolidones, copolymers of polyvinyl pyrrolidones and maleic anhydride and esters and half-esters thereof, chemically modified cellulose esters like carboxymethyl cellulose, methyl cellulose, hydroxyethyl cellulose, examples of suitable waxes are polyethylene wax, oxidized polyethylene wax, ester waxes like montan waxes, waxes of natural origin like carnauba wax, candelilla wax, bees wax etc.

Other suitable matrix materials for slow release formulations are starch, stearin, lignin.

The formulation adjuvants suitable for the preparation of the compositions according to the invention are known per se.

As liquid carriers there may be used: water, aromatic solvents such as toluene, m-xylene, o-xylene, p-xylene and mixtures thereof, cumene, aromatic hydrocarbon blends with boiling ranges between 140 and 320° C. known under various trademarks like Solvesso®, Shellsol A®, Caromax®, Hydrosol®, paraffinic and isoparaffinic carriers such as paraffin oils, mineral oils, de-aromatized hydrocarbon solvents with boiling ranges between 50 and 320° C. known for instance under the trademark Exxsol®, non-dearomatized hydrocarbon solvents with boiling ranges between 100 and 320° C. known under the tradename Varsol®, isoparaffinic solvents with boiling ranges between 100 and 320° C. known under tradenames like Isopar® or Shellsol T®, hydrocarbons such as cyclohexane, tetrahydronaphthalene (tetralin), decahydronaphthalene, alpha-pinene, d-limonene, hexadecane, isooctane, ester solvents such as ethyl acetate, n/1-butyl acetate, amyl acetate, i-bornyl acetate, 2-ethylhexyl acetate, $C_6$-$C_{18}$ alkyl esters of acetic acid known under the tradename Exxate®, lactic acid ethylester, lactic acid propylester, lactic acid butylester, benzyl benzoate, benzyl lactate, dipropyleneglycol dibenzoate, dialkyl esters of succinic, maleic and fumaric acid and polar solvents like N-methylpyrrolidone, N-ethyl pyrrolidone, $C_3$-$C_{18}$-alkyl pyrrolidones, gamma-butyrolactone, dimethylsulfoxide, N,N-dimethyl-formamide, N,N-dimethylacetamide, N,N-dimethyllactamide, $C_4$-$C_{18}$ fatty acid dimethylamides, benzoic acid dimethylamide, acetonitrile, acetone, methyl ethyl ketone, methyl-isobutyl ketone, isoamyl ketone, 2-heptanone, cyclohexanone, isophorone, methyl isobutenyl ketone (mesityl oxide), acetophenone, ethylene carbonate, propylene carbonate, butylene carbonate, alcoholic solvents and diluents such as methanol, ethanol, propanol, n/iso-butanol, n/iso-pentanol, 2-ethyl hexanol, n-octanol, tetrahydrofurfuryl alkohol, 2-methyl-2,4-pentanediol, 4-hydroxy-4-methyl-2-pentanon, cyclohexanol, benzyl alcohol, ethylene glycol, ethylene glycol butyl ether, ethylene glycol methyl ether, diethylene glycol, diethylene glycol butyl ether, diethylene glycol ethyl ether, diethylene glycol methyl ether, propylene glycol, dipropylene glycol, dipropylene glycol methyl ether and other similar glycol ether solvents based on ethylene glycol, propylene glycol and butylene glycol feedstocks, triethylene glycol, polyethylene glycol (PEG 400), polypropylenglycols with molecular masses of 400-4000, glycerol, glycerol acetate, glycerol diacetate, glycerol triacetate, 1,4-dioxane, diethylene glycol abietate, chlorobenzene, chlorotoluene, fatty acid esters such as methyl octanoate, isopropyl myristate, methyl laurate, methyl oleate, mixture of $C_8$-$C_{10}$ fatty acid methyl esters, rape seed oil methyl and ethyl esters, soy bean oil methyl and ethyl esters, vegetable oils, fatty acids such as oleic acid, linoleic acid, linolenic acid, esters of phosphoric and phosphonic acid such as triethyl phosphate, $C_3$-$C_{18}$-tris-alkyl phosphates, alkylaryl phosphates, bis-octyl-octyl phosphonates.

Water is generally the carrier of choice for the dilution of the concentrates.

Suitable solid carriers are, for example, talc, titanium dioxide, pyrophyllite clay, silica (fumed or precipated silica and optionally functionalised or treated, for instance silanised), attapulgite clay, kieselguhr, limestone, calcium carbonate, bentonite, calcium montomorillonite, cottonseed husks, wheatmeal, soybean flour, pumice, wood flour, ground walnut shells, lignin and similar materials, as described, for example, in the EPA CFR 180.1001. (c) & (d). Powdered or granulated fertilisers can also be used as solid carriers.

A large number of surface-active substances can advantageously be used both in solid and in liquid formulations, especially in those formulations which can be diluted with a carrier prior to use. Surface-active substances may be anionic, cationic, amphoteric, non-ionic or polymeric and they may be used as emulsifiying, wetting, dispersing or suspending agents or for other purposes. Typical surface-active substances include, for example, salts of alkyl sulfates, such as diethanolammonium lauryl sulfate; Sodium lauryl sulfate, salts of alkylarylsulfonates, such as calcium or sodium dodecylbenzenesulfonate; alkylphenol-alkylene oxide addition products, such as nonylphenol ethoxylates; alcohol-alkylene oxide addition products, such as tridecyl alcohol ethoxylate; soaps, such as sodium stearate; salts of alkylnaphthalenesulfonates, such as sodium dibutylnaphthalenesulfonate; dialkyl esters of sulfosuccinate salts, such as sodium di(2-ethylhexyl)sulfosuccinate; sorbitol esters, such as sorbitol oleate; quaternary amines, such as lauryl trimethylammonium chloride, polyethylene glycol esters of fatty acids, such as polyethylene glycol stearate; block copolymers of ethylene oxide and propylene oxide; and salts of mono- and di-alkyl phosphate esters; and also further substances described e.g. in "McCutcheon's Detergents and Emulsifiers Annual", MC Publishing Corp., Ridgewood, N.J., 1981.

Further adjuvants which can usually be used in pesticidal formulations include crystallisation inhibitors, viscosity-modifying substances, suspending agents, dyes, anti-oxidants, foaming agents, light absorbers, mixing aids, anti-foams, complexing agents, neutralising or pH-modifying substances and buffers, corrosion-inhibitors, fragrances, wetting agents, absorption improvers, micronutrients, plasticisers, glidants, lubricants, dispersants, thickeners, anti-freezes, microbiocides, compatibility agents and solubilisers and also liquid and solid fertilisers.

The formulations may also comprise additional active substances, for example further herbicides, herbicide safeners, plant growth regulators, fungicides or insecticides.

The compositions according to the invention can additionally include an additive (commonly referred to as an adjuvant), comprising a mineral oil, an oil of vegetable or animal origin, alkyl esters of such oils or mixtures of such oils and oil derivatives. The amount of oil additive used in the composition according to the invention is generally from 0.01 to 10%, based on the spray mixture. For example, the oil additive can be added to the spray tank in the desired concentration after the spray mixture has been prepared. Preferred oil additives comprise mineral oils or an oil of vegetable origin, for example rapeseed oil, olive oil or sunflower oil, emulsifiable vegetable oil, such as AMIGO®(Loveland Products Inc.), alkyl esters of oils of vegetable origin, for example the methyl derivatives, or an oil of animal origin, such as fish oil or beef tallow. A preferred additive contains, for example, as active components essentially 80% by weight alkyl esters of fish oils and 15% by weight methylated rapeseed oil, and also 5% by weight of customary emulsifiers and pH modifiers. Especially preferred oil additives comprise alkyl esters of $C_8$-$C_{22}$ fatty acids, especially the methyl derivatives of $C_{12}$-$C_{18}$ fatty acids, for example the methyl esters of lauric acid, palmitic acid and oleic acid, being important. Those esters are known as methyl laurate (CAS-111-82-0), methyl palmitate (CAS-112-39-0) and methyl oleate (CAS-112-62-9). A preferred fatty acid methyl ester derivative is AGNIQUE ME 18 RD-F® (Cognis). Those and other oil derivatives are also known from the Compendium of Herbicide Adjuvants, 5th Edition, Southern Illinois University, 2000.

The application and action of the oil additives can be further improved by combining them with surface-active substances, such as non-ionic, anionic, cationic or amphoteric surfactants. Examples of suitable anionic, non-ionic, cationic or amphoteric surfactants are listed on pages 7 and 8 of WO97/34485. Preferred surface-active substances are anionic surfactants of the dodecylbenzylsulfonate type, especially the calcium salts thereof, and also non-ionic surfactants of the fatty alcohol ethoxylate type. Special preference is given to ethoxylated $C_{12}$-$C_{22}$ fatty alcohols having a degree of ethoxylation of from 5 to 40. Examples of commercially available surfactants are the Genapol types (Clariant). Also preferred are silicone surfactants, especially polyalkyl-oxide-modified heptamethyltrisiloxanes, which are commercially available e.g. as SILWET L-77®, and also perfluorinated surfactants. The concentration of surface-active substances in relation to the total additive is generally from 1 to 50% by weight. Examples of oil additives that consist of mixtures of oils or mineral oils or derivatives thereof with surfactants are TURBOCHARGED, ADIGOR® (both (Syngenta Crop Protection AG), ACTIPRON® (BP Oil UK Limited), AGRI-DEX® (Helena Chemical Company).

The said surface-active substances may also be used in the formulations alone, that is to say without oil additives.

Furthermore, the addition of an organic solvent to the oil additive/surfactant mixture can contribute to a further enhancement of action. Suitable solvents are, for example, SOLVESSO® and AROMATIC® solvents (Exxon Corporation). The concentration of such solvents can be from 10 to 80% by weight of the total weight. Such oil additives, which may be in admixture with solvents, are described, for example, in U.S. Pat. No. 4,834,908. A commercially available oil additive disclosed therein is known by the name MERGE® (BASF). Further oil additives that are preferred according to the invention are SCORE® and ADIGOR® (both Syngenta Crop Protection AG).

In addition to the oil additives listed above, in order to enhance the activity of the compositions according to the invention it is also possible for formulations of alkylpyrrolidones, (e.g. AGRIMAX® from ISP) to be added to the spray mixture. Formulations of synthetic latices, such as, for example, polyacrylamide, polyvinyl compounds or poly-1-p-menthene (e.g. BOND®, COURIER® or EMERALD®) can also be used.

Such adjuvant oils as described in the preceding paragraphs may be employed as the carrier liquid in which an active compound is dissolved, emulsified or dispersed as appropriate to the physical form of the active compound.

The pesticidal formulations generally contain from 0.1 to 99% by weight, especially from 0.1 to 95% by weight, of a compound of formula I and from 1 to 99.9% by weight of a formulation adjuvant, which preferably includes from 0 to 25% by weight of a surface-active substance. Whereas commercial products will preferably be formulated as concentrates, the end user will normally employ dilute formulations.

The rate of application of the compounds of formula I may vary within wide limits and depends upon the nature of the soil, the method of application (pre- or post-emergence; seed dressing; application to the seed furrow; no tillage application etc.), the crop plant, the weed or grass to be controlled, the prevailing climatic conditions, and other factors governed by the method of application, the time of application and the target crop. The compounds of formula I according to the invention are generally applied at a rate of 1-2000 g/ha, preferably 1-1000 g/ha and most preferably at 1-500 g/ha.

Preferred formulations have especially the following representative compositions:
(%=percent by weight):
Emulsifiable Concentrates:
active ingredient: 1 to 95%, preferably 60 to 90%
surface-active agents: 1 to 30%, preferably 5 to 20%
solvents as liquid carrier: 1 to 80%, preferably 1 to 35%
Dusts:
active ingredient: 0.1 to 10%, preferably 0.1 to 5%
solid carriers: 99.9 to 90%, preferably 99.9 to 99%
Suspension Concentrates:
active ingredient: 5 to 75%, preferably 10 to 50%
water: 94 to 24%, preferably 88 to 30%
surface-active agents: 1 to 40%, preferably 2 to 30%
Wettable Powders:
active ingredient: 0.5 to 90%, preferably 1 to 80%
surface-active agents: 0.5 to 20%, preferably 1 to 15
    solid carriers: 5 to 95%, preferably 15 to 90%
Granules:
active ingredient: 0.1 to 30%, preferably 0.1 to 15%
solid carriers: 99.5 to 70%, preferably 97 to 85%
Waterdispersible Granules:
active ingredient: 1 to 90%, preferably 10 to 80%
surface-active agents: 0.5 to 80%, preferably 5 to 30%
solid carriers: 90 to 10%, preferably 70 to 30%

The following Examples further illustrate, but do not limit, the invention.

| F1. Emulsifiable concentrates | | | | |
| --- | --- | --- | --- | --- |
|  | a) | b) | c) | d) |
| active ingredient | 5% | 10% | 25% | 50% |
| calcium dodecylbenzene-sulfonate | 6% | 8% | 6% | 8% |
| castor oil polyglycol ether (36 mol of ethylene oxide) | 4% | — | 4% | 4% |
| octylphenol polyglycol ether (7-8 mol of ethylene oxide) | — | 4% | — | 2% |
| NMP | — | 10% | — | 20% |
| arom. hydrocarbon mixture $C_9$-$C_{12}$ | 85% | 68% | 65% | 16% |

Emulsions of any desired concentration can be prepared from such concentrates by dilution with water.

| F2. Solutions | | | | |
| --- | --- | --- | --- | --- |
|  | a) | b) | c) | d) |
| active ingredient | 5% | 10% | 50% | 90% |
| 1-methoxy-3-(3-methoxy-propoxy)-propane | 40% | 50% | — | — |
| polyethylene glycol MW 400 | 20% | 10% | — | — |
| NMP | — | — | 50% | 10% |
| arom. hydrocarbon mixture $C_9$-$C_{12}$ | 35% | 30% | — | — |

The solutions are suitable for application undiluted or after dilution with water.

| F3. Wettable powders | a) | b) | c) | d) |
|---|---|---|---|---|
| active ingredient | 5% | 25% | 50% | 80% |
| sodium lignosulfonate | 4% | — | 3% | — |
| sodium lauryl sulfate | 2% | 3% | — | 4% |
| sodium diisobutylnaphthalene-sulfonate | — | 6% | 5% | 6% |
| octylphenol polyglycol ether (7-8 mol of ethylene oxide) | — | 1% | 2% | — |
| highly dispersed silicic acid | 1% | 3% | 5% | 10% |
| kaolin | 88% | 62% | 35% | — |

The active ingredient is thoroughly mixed with the adjuvants and the mixture is thoroughly ground in a suitable mill, yielding wettable powders which can be diluted with water to give suspensions of any desired concentration.

| F4. Coated granules | a) | b) | c) |
|---|---|---|---|
| active ingredient | 0.1% | 5% | 15% |
| highly dispersed silica | 0.9% | 2% | 2% |
| inorg. carrier (diameter 0.1-1 mm) e.g. CaCO$_3$ or SiO$_2$ | 99.0% | 93% | 83% |

The active ingredient is dissolved in methylene chloride, the solution is sprayed onto the carrier and the solvent is subsequently evaporated off in vacuo.

| F5. Coated granules | a) | b) | c) |
|---|---|---|---|
| active ingredient | 0.1% | 5% | 15% |
| polyethylene glycol MW 200 | 1.0% | 2% | 3% |
| highly dispersed silica | 0.9% | 1% | 2% |
| inorg. carrier (diameter 0.1-1 mm) e.g. CaCO$_3$ or SiO$_2$ | 98.0% | 92% | 80% |

The finely ground active ingredient is applied uniformly, in a mixer, to the carrier moistened with polyethylene glycol. Non-dusty coated granules are obtained in this manner.

| F6. Extruded granules | a) | b) | c) | d) |
|---|---|---|---|---|
| active ingredient | 0.1% | 3% | 5% | 15% |
| sodium lignosulfonate | 1.5% | 2% | 3% | 4% |
| carboxymethylcellulose | 1.4% | 2% | 2% | 2% |
| kaolin | 97.0% | 93% | 90% | 79% |

The active ingredient is mixed and ground with the adjuvants and the mixture is moistened with water. The resulting mixture is extruded and then dried in a stream of air.

| F7. Water-dispersible granules | a) | b) | c) | d) |
|---|---|---|---|---|
| active ingredient | 5% | 10% | 40% | 90% |
| sodium lignosulfonate | 20% | 20% | 15% | 7% |
| dibutyl naphthalene sulfonate | 5% | 5% | 4% | 2% |
| Gum arabic | 2% | 1% | 1% | 1% |
| Diatomaceous earth | 20% | 30% | 5% | — |
| Sodium sulfate | 4% | 5% | — | — |
| kaolin | 48% | 30% | 30% | — |

The active ingredient is mixed and ground with the adjuvants and the mixture is moistened with water. The resulting mixture is extruded and then dried in a stream of air.

| F7. Dusts | a) | b) | c) |
|---|---|---|---|
| active ingredient | 0.1% | 1% | 5% |
| talcum | 39.9% | 49% | 35% |
| kaolin | 60.0% | 50% | 60% |

Ready-to-use dusts are obtained by mixing the active ingredient with the carriers and grinding the mixture in a suitable mill.

| F8. Suspension concentrates | a) | b) | c) | d) |
|---|---|---|---|---|
| active ingredient | 3% | 10% | 25% | 50% |
| propylene glycol | 5% | 5% | 5% | 5% |
| nonylphenol polyglycol ether (15 mol of ethylene oxide) | — | 1% | 2% | — |
| sodium lignosulfonate | 3% | 3% | 7% | 6% |
| heteropolysacharide (Xanthan) | 0.2% | 0.2% | 0.2% | 0.2% |
| 1,2-Benzisothiazolin-3-on | 0.1% | 0.1% | 0.1% | 0.1% |
| silicone oil emulsion | 0.7% | 0.7% | 0.7% | 0.7% |
| water | 87% | 79% | 62% | 38% |

The finely ground active ingredient is intimately mixed with the adjuvants, yielding a suspension concentrate from which suspensions of any desired concentration can be prepared by dilution with water.

Crops of useful plants in which the compositions according to the invention can be used include especially cereals, in particular wheat and barley, rice, corn, rape, sugarbeet, sugarcane, soybean, cotton, sunflower, peanut and plantation crops.

The term "crops" is to be understood as also including crops that have been rendered tolerant to herbicides or classes of herbicides (for example ALS, GS, EPSPS, PPO and HPPD inhibitors) as a result of conventional methods of breeding or genetic engineering. An example of a crop that has been rendered tolerant e.g. to imidazolinones, such as imazamox, by conventional methods of breeding is Clearfield® summer rape (Canola). Examples of crops that have been rendered tolerant to herbicides by genetic engineering methods include e.g. glyphosate- and glufosinate-resistant maize varieties commercially available under the trade names RoundupReady® and LibertyLink®. The weeds to be controlled may be both monocotyledonous and dicotyledonous weeds, such as, for example, *Stellaria, Nasturtium, Agrostis, Digitaria, Avena, Setaria, Sinapis, Lolium, Solanum, Echinochloa, Scirpus, Monochoria, Sagittaria, Bromus, Alopecurus, Sorghum, Rottboellia, Cyperus, Abutilon, Sida, Xanthium, Amaranthus, Chenopodium, Ipomoea, Chrysanthemum, Galium, Viola* and *Veronica*. Control of monocotyledonous weeds, in particular *Agrostis, Avena, Setaria, Lolium, Echinochloa, Bromus, Alopecurus* and *Sorghum* is very extensive.

Crops are also to be understood as being those which have been rendered resistant to harmful insects by genetic engineering methods, for example Bt maize (resistant to European corn borer), Bt cotton (resistant to cotton boll weevil) and also Bt potatoes (resistant to Colorado beetle). Examples of Bt maize are the Bt-176 maize hybrids of NK® (Syngenta Seeds). The Bt toxin is a protein that is formed naturally by *Bacillus thuringiensis* soil bacteria. Examples of toxins and transgenic plants able to synthesise such toxins are described in EP-A-451 878, EP-A-374 753, WO 93/07278, WO 95/34656, WO 03/052073 and EP-A-427 529. Examples of transgenic plants that contain one or more genes which code for an insecticidal resistance and express one or more toxins are KnockOut® (maize), Yield Gard® (maize), NuCOTN33B® (cotton), Bollgard® (cotton), NewLeaf® (potatoes), NatureGard® and Protexcta®. Plant crops and their seed material can be resistant to herbicides and at the same time also to insect feeding ("stacked" transgenic events). Seed can, for example, have the ability to express an insecticidally active Cry3 protein and at the same time be glyphosate-tolerant. The term "crops" is to be understood as also including crops obtained as a result of conventional methods of breeding or genetic engineering which contain so-called output traits (e.g. improved flavour, storage stability, nutritional content).

Areas under cultivation are to be understood as including land where the crop plants are already growing as well as land intended for the cultivation of those crop plants.

The compounds of formula I according to the invention can also be used in combination with further herbicides. Preferably, in these mixtures, the compound of the formula I is one of those compounds listed in Tables 1 to 56 below. The following mixtures of the compound of formula I are especially important:

compound of formula I+acetochlor, compound of formula I+acifluorfen, compound of formula I+acifluorfen-sodium, compound of formula I+aclonifen, compound of formula I+acrolein, compound of formula I+alachlor, compound of formula I+alloxydim, compound of formula I+allyl alcohol, compound of formula I+ametryn, compound of formula I+amicarbazone, compound of formula I+amidosulfuron, compound of formula I+aminopyralid, compound of formula I+amitrole, compound of formula I+ammonium sulfamate, compound of formula I+anilofos, compound of formula I+asulam, compound of formula I+atraton, compound of formula I+atrazine, compound of formula I+azimsulfuron, compound of formula I+BCPC, compound of formula I+beflubutamid, compound of formula I+benazolin, compound of formula I+benfluralin, compound of formula I+benfuresate, compound of formula I+bensulfuron, compound of formula I+bensulfuron-methyl, compound of formula I+bensulide, compound of formula I+bentazone, compound of formula I+benzfendizone, compound of formula I+benzobicyclon, compound of formula I+benzofenap, compound of formula I+bifenox, compound of formula I+bilanafos, compound of formula I+bispyribac, compound of formula I+bispyribac-sodium, compound of formula I+borax, compound of formula I+bromacil, compound of formula I+bromobutide, compound of formula I+bromoxynil, compound of formula I+butachlor, compound of formula I+butafenacil, compound of formula I+butamifos, compound of formula I+butralin, compound of formula I+butroxydim, compound of formula I+butylate, compound of formula I+cacodylic acid, compound of formula I+calcium chlorate, compound of formula I+cafenstrole, compound of formula I+carbetamide, compound of formula I+carfentrazone, compound of formula I+carfentrazone-ethyl, compound of formula I+CDEA, compound of formula I+CEPC, compound of formula I+chlorflurenol, compound of formula I+chlorflurenol-methyl, compound of formula I+chloridazon, compound of formula I+chlorimuron, compound of formula I+chlorimuron-ethyl, compound of formula I+chloroacetic acid, compound of formula I+chlorotoluron, compound of formula I+chlorpropham, compound of formula I+chlorsulfuron, compound of formula I+chlorthal, compound of formula I+chlorthal-dimethyl, compound of formula I+cinidon-ethyl, compound of formula I+cinmethylin, compound of formula I+cinosulfuron, compound of formula I+cisanilide, compound of formula I+clethodim, compound of formula I+clodinafop, compound of formula I+clodinafop-propargyl, compound of formula I+clomazone, compound of formula I+clomeprop, compound of formula I+clopyralid, compound of formula I+cloransulam, compound of formula I+cloransulam-methyl, compound of formula I+CMA, compound of formula I+4-CPB, compound of formula I+CPMF, compound of formula I+4-CPP, compound of formula I+CPPC, compound of formula I+cresol, compound of formula I+cumyluron, compound of formula I+cyanamide, compound of formula I+cyanazine, compound of formula I+cycloate, compound of formula I+cyclosulfamuron, compound of formula I+cycloxydim, compound of formula I+cyhalofop, compound of formula I+cyhalofop-butyl, compound of formula I+2,4-D, compound of formula I+3,4-DA, compound of formula I+daimuron, compound of formula I+dalapon, compound of formula I+dazomet, compound of formula I+2,4-DB, compound of formula I+3,4-DB, compound of formula I+2,4-DEB, compound of formula I+desmedipham, compound of formula I+dicamba, compound of formula I+dichlobenil, compound of formula I+ortho-dichlorobenzene, compound of formula I+para-dichlorobenzene, compound of formula I+dichlorprop, compound of formula I+dichlorprop-P, compound of formula I+diclofop, compound of formula I+diclofop-methyl, compound of formula I+diclosulam, compound of formula I+difenzoquat, compound of formula I+difenzoquat metilsulfate, compound of formula I+diflufenican, compound of formula I+diflufenzopyr, compound of formula I+dimefuron, compound of formula I+dimepiperate, compound of formula I+dimethachlor, compound of formula I+dimethametryn, compound of formula I+dimethenamid, compound of formula I+dimethenamid-P, compound of formula I+dimethipin, compound of formula I+dimethylarsinic acid, compound of formula I+dinitramine, compound of formula I+dinoterb, compound of formula I+diphenamid, compound of formula I+diquat, compound of formula I+diquat dibromide, compound of formula I+dithiopyr, compound of formula I+diuron, compound of formula I+DNOC, compound of formula I+3,4-DP, compound of formula I+DSMA, compound of formula I+EBEP, compound of formula I+endothal, compound of formula I+EPTC, compound of formula I+esprocarb, compound of formula I+ethalfluralin, compound of formula I+ethametsulfuron, compound of formula I+ethametsulfuron-methyl, compound of formula I+ethofumesate, compound of formula I+ethoxyfen, compound of formula I+ethoxysulfuron, compound of formula I+etobenzanid, compound of formula I+fenoxaprop-P, compound of formula I+fenoxaprop-P-ethyl, compound of formula I+fenoxasulfone (CAS RN 639826-16-7), compound of formula I+fentrazamide, compound of formula I+ferrous sulfate, compound of formula I+flamprop-M, compound of formula I+flazasulfuron, compound of formula I+florasulam, compound of formula I+fluazifop, compound of formula I+fluazifop-butyl, compound of formula I+fluazifop-P, compound of formula I+fluazifop-P-butyl, compound of formula I+flucarbazone, compound of formula I+flucarbazone-sodium, compound of formula I+flucetosulfuron, compound of formula I+fluchloralin, compound of formula I+flufenacet, compound of formula I+flufenpyr, compound of formula I+flufenpyr-ethyl, compound of formula I+flumetsulam, compound of formula I+flumiclorac, compound of formula I+flumiclorac-pentyl, compound of formula I+flumioxazin, compound of formula I+fluometuron, compound of formula I+fluoroglycofen, compound of formula I+fluoroglycofen-ethyl, compound of formula I+flupropanate, compound of formula I+flupyrsulfuron, compound of formula I+flupyrsulfuron-methyl-sodium, compound of formula I+flurenol, compound of formula I+fluridone, compound of formula I+fluorochloridone, compound of formula I+fluoroxypyr, compound of formula I+flurtamone, compound of formula I+fluthiacet, compound of formula I+fluthiacet-methyl, compound of formula I+fomesafen, compound of formula I+foramsulfuron, compound of formula I+fosamine, compound of formula I+glufosinate, compound of formula I+glufosinate-ammonium, compound of formula I+glyphosate, compound of formula I+halosulfuron, compound of formula I+halosulfuron-methyl, compound of formula I+haloxyfop, compound of formula I+haloxyfop-P, compound of formula I+HC-252, compound of formula I+hexazinone, compound of formula I+imazamethabenz, compound of formula I+imazamethabenz-methyl, compound of formula I+imazamox, compound of formula I+imazapic, compound of formula I+imazapyr, compound of formula I+imazaquin, compound of formula I+imazethapyr, compound of formula I+imazosulfuron, compound of formula I+indanofan, compound of formula I+iodomethane, compound of formula I+iodosulfuron, compound of formula I+iodosulfuron-methyl-sodium, compound of formula I+ioxynil, compound of formula I+ipfencarbazone (CAS RN 212201-70-2), compound of formula I+isoproturon, compound of formula I+isouron, compound of formula I+isoxaben, compound of formula I+isoxachlortole, compound of formula I+isoxaflutole, compound of formula I+karbutilate, compound of formula I+lactofen, compound of formula I+lenacil, compound of formula I+linuron, compound of formula I+MAA, compound of formula I+MAMA, compound of formula I+MCPA, compound of formula I+MCPA-thioethyl, compound of formula I+MCPB, compound of formula I+mecoprop, compound of formula I+mecoprop-P, compound of formula I+mefenacet, compound of formula I+mefluidide, compound of formula I+mesosulfuron, compound of formula I+mesosulfuron-methyl, compound of formula I+mesotrione, compound of formula I+metam, compound of formula I+metamifop, compound of formula I+metamitron, compound of formula I+metazachlor, compound of formula I+metazosulfuron (NC-620, CAS RN 868680-84-6), compound of formula I+methabenzthiazuron, compound of formula I+methylarsonic acid, compound of formula I+methyldymron, compound of formula I+methyl isothiocyanate, compound of formula I+metobenzuron, compound of formula I+metolachlor, compound of formula I+S-metolachlor, compound of formula I+metosulam, compound of formula I+metoxuron, compound of formula I+metribuzin, compound of formula I+metsulfuron, compound of formula I+metsulfuron-methyl, compound of formula I+MK-616, compound of formula I+molinate, compound of formula I+monolinuron, compound of formula I+MSMA, compound of formula I+naproanilide, compound of formula I+napropamide, compound of formula I+naptalam, compound of formula I+neburon, compound of formula I+nicosulfuron, compound of formula I+nonanoic acid, compound of formula I+norflurazon, compound of formula I+oleic acid (fatty acids), compound of formula I+orbencarb, compound of formula I+orthosulfamuron, compound of formula I+oryzalin, compound of formula I+oxadiargyl, compound of formula I+oxadiazon, compound of formula I+oxasulfuron, compound of formula I+oxaziclomefone, compound of formula I+oxyfluorfen, compound of formula I+paraquat, compound of formula I+paraquat dichloride, compound of formula I+pebulate, compound of formula I+pendimethalin, compound of formula I+penoxsulam, compound of formula I+pentachlorophenol, compound of formula I+pentanochlor, compound of formula I+pentoxazone, compound of formula I+pethoxamid, compound of formula I+petrolium oils, compound of formula I+phenmedipham, compound of formula I+phenmedipham-ethyl, compound of formula I+picloram, compound of formula I+picolinafen, compound of formula I+pinoxaden, compound of formula I+piperophos, compound of formula I+potassium arsenite, compound of formula I+potassium azide, compound of formula I+pretilachlor, compound of formula I+primisulfuron, compound of formula I+primisulfuron-methyl, compound of formula I+prodiamine, compound of formula I+profluazol, compound of formula I+profoxydim, compound of formula I+prometon, compound of formula I+prometryn, compound of formula I+propachlor, compound of formula I+propanil, compound of formula I+propaquizafop, compound of formula I+propazine, compound of formula I+propham, compound of formula I+propisochlor, compound of formula I+propoxycarbazone, compound of formula I+propoxycarbazone-sodium, compound of formula I+propyrisulfuron (TH-547, CAS RN 570415-88-2), compound of formula I+propyzamide, compound of formula I+prosulfocarb, compound of formula I+prosulfuron, compound of formula I+pyraclonil, compound of formula I+pyraflufen, compound of formula I+pyraflufen-ethyl, compound of formula I+pyrazolynate, compound of formula I+pyrazosulfuron, compound of formula I+pyrazosulfuron-ethyl, compound of formula I+pyrazoxyfen, compound of formula I+pyribenzoxim, compound of formula I+pyributicarb, compound of formula I+pyridafol, compound of formula I+pyridate, compound of formula I+pyriftalid, compound of formula I+pyriminobac, compound of formula I+pyriminobac-methyl, compound of formula I+pyrimisulfan, compound of formula I+pyrithiobac, compound of formula I+pyrithiobac-sodium, compound of formula I+quinclorac, compound of formula I+quinmerac, compound of formula I+quinoclamine, compound of formula I+quizalofop, compound of formula I+quizalofop-P, compound of formula I+rimsulfuron, compound of formula I+sethoxydim, compound of formula I+siduron, compound of formula I+simazine, compound of formula I+simetryn, compound of formula I+SMA, compound of formula I+sodium arsenite, compound of formula I+sodium azide, compound of formula I+sodium chlorate, compound of formula I+sulcotrione, compound of formula I+sulfentrazone, compound of formula I+sulfometuron, compound of formula I+sulfometuron-methyl, compound of formula I+sulfosate, compound of formula I+sulfosulfuron, compound of formula I+sulfuric acid, compound of formula I+tar oils, compound of formula I+2,3,6-TBA, compound of formula I+TCA, compound of formula I+TCA-sodium, compound of formula I+tebuthiuron, compound of formula I+tepraloxydim, compound of formula I+terbacil, compound of formula I+terbumeton, compound of formula I+terbuthylazine, compound of formula I+terbutryn, compound of formula I+thenylchlor, compound of formula I+thiazopyr, compound of formula I+thifensulfuron, compound of formula I+thifensulfuron-methyl, compound of formula I+thiobencarb, compound of formula I+tiocarbazil, compound of formula I+topramezone, compound of formula I+tralkoxydim, compound of formula I+tri-allate, compound of formula I+triasulfuron, compound of formula I+triaziflam, compound of formula I+tribenuron, compound of formula I+tribenuron-methyl, compound of formula I+tricamba, compound of formula I+triclopyr, compound of formula I+trietazine, compound of formula I+trifloxysulfuron, compound of formula I+trifloxysulfuron-sodium, compound of formula I+trifluralin, compound of formula I+triflusulfuron, compound of formula I+triflusulfuron-methyl, compound of formula I+trihydroxytriazine, compound of formula I+tritosulfuron, compound of formula I+[3-[2-chloro-4-fluoro-5-(1-methyl-6-trifluoromethyl-2,4-dioxo-1,2,3,4-tetrahydropyrimidin-3-yl)phenoxy]-2-pyridyloxy]acetic acid ethyl ester (CAS RN 353292-31-6), compound of formula I+4-[(4,5-dihydro-3-methoxy-4-methyl-5-oxo)-1H-1,2,4-triazol-1-ylcarbonylsulfamoyl]-5-methylthiophene-3-carboxylic acid (BAY636), compound of formula I+BAY747 (CAS RN 335104-84-2), compound of formula I+topramezone (CAS RN 210631-68-8), compound of formula I+4-hydroxy-3-[[2-[(2-methoxyethoxy)methyl]-6-(trifluoromethyl)-3-pyridinyl]carbonyl]-bicyclo[3.2.1]oct-3-en-2-one (CAS RN 352010-68-5), and compound of formula I+4-hydroxy-3-[[2-(3-methoxypropyl)-6-(difluoromethyl)-3-pyridinyl]carbonyl]-bicyclo[3.2.1]oct-3-en-2-one.

The mixing partners for the compound of formula I may also be in the form of esters or salts, as mentioned e.g. in The Pesticide Manual, 12th Edition (BCPC) 2000.

For applications in cereals, the following mixtures are preferred: compound of formula I+aclonifen, compound of formula I+amidosulfuron, compound of formula I+aminopyralid, compound of formula I+beflubutamid, compound of formula I+benfluralin, compound of formula I+bifenox, compound of formula I+bromoxynil, compound of formula I+butafenacil, compound of formula I+carbetamide, compound of formula I+carfentrazone, compound of formula I+carfentrazone-ethyl, compound of formula I+chlorotoluron, compound of formula I+chlorpropham, compound of formula I+chlorsulfuron, compound of formula I+cinidon-ethyl, compound of formula I+clodinafop, compound of formula I+clodinafop-propargyl, compound of formula I+clopyralid, compound of formula I+2,4-D, compound of formula I+dicamba, compound of formula I+dichlobenil, compound of formula I+dichlorprop, compound of formula I+diclofop, compound of formula I+diclofop-methyl, compound of formula I+difenzoquat, compound of formula I+difenzoquat metilsulfate, compound of formula I+diflufenican, compound of formula I+diquat, compound of formula I+diquat dibromide, compound of formula I+fenoxaprop-P, compound of formula I+fenoxaprop-P-ethyl, compound of formula I+flamprop-M, compound of formula I+florasulam, compound of formula I+fluazifop-P-butyl, compound of formula I+flucarbazone, compound of formula I+flucarbazone-sodium, compound of formula I+flufenacet, compound of formula I+flupyrsulfuron, compound of formula I+flupyrsulfuron-methyl-sodium, compound of formula I+fluorochloridone, compound of formula I+fluoroxypyr, compound of formula I+flurtamone, compound of formula I+imazamethabenz-methyl, compound of formula I+imazamox, compound of formula I+iodosulfuron, compound of formula I+iodosulfuron-methyl-sodium, compound of formula I+ioxynil, compound of formula I+isoproturon, compound of formula I+linuron, compound of formula I+MCPA, compound of formula I+mecoprop, compound of formula I+mecoprop-P, compound of formula I+mesosulfuron, compound of formula I+mesosulfuron-methyl, compound of formula I+mesotrione, compound of formula I+metribuzin, compound of formula I+metsulfuron, compound of formula I+metsulfuron-methyl, compound of formula I+pendimethalin, compound of formula I+picolinafen, compound of formula I+pinoxaden, compound of formula I+prodiamine, compound of formula I+propanil, compound of formula I+propoxycarbazone, compound of formula I+propoxycarbazone-sodium, compound of formula I+prosulfocarb, compound of formula I+pyrasulfotole, compound of formula I+pyridate, compound of formula I+pyroxasulfone (KIN-485), compound of formula I+pyroxsulam compound of formula I+sulfosulfuron, compound of formula I+tembotrione, compound of formula I+terbutryn, compound of formula I+thifensulfuron, compound of formula I+thiencarbazone, compound of formula I+thifensulfuron-methyl, compound of formula I+topramezone, compound of formula I+tralkoxydim, compound of formula I+tri-allate, compound of formula I+triasulfuron, compound of formula I+tribenuron, compound of formula I+tribenuron-methyl, compound of formula I+trifluralin, compound of formula I+trinexapac-ethyl and compound of formula I+tritosulfuron, where the mixtures comprising a compound of formula (I)+amidosulfuron, compound of formula (I)+aminopyralid, compound of formula (I)+beflubutamid, compound of formula (I)+bromoxynil, compound of formula (I)+carfentrazone, compound of formula (I)+carfentrazone-ethyl, compound of formula (I)+chlorotoluron, compound of formula (I)+chlorsulfuron, compound of formula (I)+clodinafop, compound of formula (I)+clodinafop-propargyl, compound of formula (I)+clopyralid, 2,4-D, compound of formula (I)+dicamba, compound of formula (I)+difenzoquat, compound of formula (I)+difenzoquat metilsulfate, compound of formula (I)+diflufenican, compound of formula (I)+fenoxaprop-P, compound of formula (I)+fenoxaprop-P-ethyl, compound of formula (I)+florasulam, compound of formula (I)+flucarbazone, compound of formula (I)+flucarbazone-sodium, compound of formula (I)+flufenacet, compound of formula (I)+flupyrsulfuron, compound of formula (I)+flupyrsulfuron-methyl-sodium, compound of formula (I)+fluoroxypyr, compound of formula (I)+flurtamone, compound of formula (I)+iodosulfuron, compound of formula (I)+iodosulfuron-methyl-sodium, compound of formula (I)+MCPA, compound of formula (I)+mesosulfuron, compound of formula (I)+mesosulfuron-methyl, compound of formula (I)+metsulfuron, compound of formula (I)+metsulfuron-methyl, compound of formula (I)+pendimethalin, compound of formula (I)+picolinafen, compound of formula (I)+pinoxaden, compound of formula (I)+prosulfocarb, compound of formula (I)+pyrasulfotole, compound of formula (I)+pyroxasulfone (KIN-485), compound of formula (I)+pyroxsulam, compound of formula (I)+sulfosulfuron, compound of formula (I)+thifensulfuron, compound of formula (I)+thifensulfuron-methyl, compound of formula (I)+tralkoxydim, compound of formula (I)+triasulfuron, compound of formula (I)+tribenuron, compound of formula (I)+tribenuron-methyl, compound of formula (I)+trifluralin, compound of formula (I)+trinexapac-ethyl and compound of formula (I)+tritosulfuron are particularly preferred.

For applications in rice, the following mixtures are preferred: compound of formula (I)+azimsulfuron, compound of formula (I)+bensulfuron, compound of formula (I)+bensulfuron-methyl, compound of formula (I)+benzobicyclon, compound of formula (I)+benzofenap, compound of formula (I)+bispyribac, compound of formula (I)+bispyribac-sodium, compound of formula (I)+butachlor, compound of formula (I)+cafenstrole, compound of formula (I)+cinosulfuron, compound of formula (I)+clomazone, compound of formula (I)+clomeprop, compound of formula (I)+cyclosulfamuron, compound of formula (I)+cyhalofop, compound of formula (I)+cyhalofop-butyl, compound of formula (I)+2,4-D, compound of formula (I)+daimuron, compound of formula (I)+dicamba, compound of formula (I)+diquat, compound of formula (I)+diquat dibromide, compound of formula (I)+esprocarb, compound of formula (I)+ethoxysulfuron, compound of formula (I)+fenoxaprop-P, compound of formula (I)+fenoxaprop-P-ethyl, compound of formula I+fenoxasulfone (CAS RN 639826-16-7), compound of formula (I)+fentrazamide, compound of formula (I)+florasulam, compound of formula (I)+glufosinate-ammonium, compound of formula (I)+glyphosate, compound of formula (I)+halosulfuron, compound of formula (I)+halosulfuron-methyl, compound of formula (I)+imazosulfuron, compound of formula I+ipfencarbazone (CAS RN 212201-70-2), compound of formula (I)+MCPA, compound of formula (I)+mefenacet, compound of formula (I)+mesotrione, compound of formula (I)+metamifop, compound of formula I+metazosulfuron (NC-620, CAS RN 868680-84-6), compound of formula (I)+metsulfuron, compound of formula (I)+metsulfuron-methyl, compound of formula (I)+n-methyl glyphosate, compound of formula (I)+orthosulfamuron, compound of formula (I)+oryzalin, compound of formula (I)+oxadiargyl, compound of formula (I)+oxadiazon, compound of formula (I)+paraquat dichloride, compound of formula (I)+pendimethalin, compound of formula (I)+penoxsulam, compound of formula (I)+pretilachlor, compound of formula (I)+profoxydim, compound of formula (I)+propanil, compound of formula I+propyrisulfuron (TH-547, CAS RN 570415-88-2), compound of formula (I)+pyrazolynate, compound of formula (I)+pyrazosulfuron, compound of formula (I)+pyrazosulfuron-ethyl, compound of formula (I)+pyrazoxyfen, compound of formula (I)+pyribenzoxim, compound of formula (I)+pyriftalid, compound of formula (I)+pyriminobac, compound of formula (I)+pyriminobac-methyl, compound of formula (I)+pyrimisulfan, compound of formula (I)+quinclorac, compound of formula (I)+tefuryltrione, compound of formula (I)+triasulfuron and compound of formula (I)+trinexapac-ethyl, where the mixtures comprising a compound of formula (I)+azimsulfuron, compound of formula (I)+bensulfuron, compound of formula (I)+bensulfuron-methyl, compound of formula (I)+benzobicyclon, compound of formula (I)+benzofenap, compound of formula (I)+bispyribac, compound of formula (I)+bispyribac-sodium, compound of formula (I)+clomazone, compound of formula (I)+clomeprop, compound of formula (I)+cyhalofop, compound of formula (I)+cyhalofop-butyl, compound of formula (I)+2,4-D, compound of formula (I)+daimuron, compound of formula (I)+dicamba, compound of formula (I)+esprocarb, compound of formula (I)+ethoxysulfuron, compound of formula (I)+fenoxaprop-P, compound of formula (I)+fenoxaprop-P-ethyl, compound of formula I+fenoxasulfone (CAS RN 639826-16-7), compound of formula (I)+fentrazamide, compound of formula (I)+florasulam, compound of formula (I)+halosulfuron, compound of formula (I)+halosulfuron-methyl, compound of formula (I)+imazosulfuron, compound of formula I+ipfencarbazone (CAS RN 212201-70-2), compound of formula (I)+MCPA, compound of formula (I)+mefenacet, compound of formula (I)+mesotrione, compound of formula I+metazosulfuron (NC-620, CAS RN 868680-84-6), compound of formula (I)+metsulfuron, compound of formula (I)+metsulfuron-methyl, compound of formula (I)+orthosulfamuron, compound of formula (I)+oxadiargyl, compound of formula (I)+oxadiazon, compound of formula (I)+pendimethalin, compound of formula (I)+penoxsulam, compound of formula (I)+pretilachlor, compound of formula I+propyrisulfuron (TH-547, CAS RN 570415-88-2), compound of formula (I)+pyrazolynate, compound of formula (I)+pyrazosulfuron, compound of formula (I)+pyrazosulfuron-ethyl, compound of formula (I)+pyrazoxyfen, compound of formula (I)+pyribenzoxim, compound of formula (I)+pyriftalid, compound of formula (I)+pyriminobac, compound of formula (I)+pyriminobac-methyl, compound of formula (I)+pyrimisulfan, compound of formula (I)+quinclorac, compound of formula (I)+tefuryltrione, compound of formula (I)+triasulfuron and compound of formula (I)+trinexapac-ethyl are particularly preferred.

The compounds of formula I according to the invention can also be used in combination with safeners. Preferably, in these mixtures, the compound of the formula I is one of those compounds listed in Tables 1 to 56 below. The following mixtures with safeners, especially, come into consideration: compound of formula I+cloquintocet-mexyl, compound of formula I+cloquintocet acid and salts thereof, compound of formula I+fenchlorazole-ethyl, compound of formula I+fenchlorazole acid and salts thereof, compound of formula I+mefenpyr-diethyl, compound of formula I+mefenpyr diacid, compound of formula I+isoxadifen-ethyl, compound of formula I+isoxadifen acid, compound of formula I+furilazole, compound of formula I+furilazole R isomer, compound of formula (I)+N-(2-methoxybenzoyl)-4-[(methylaminocarbonyl)amino]benzenesulfonamide, compound of formula I+benoxacor, compound of formula I+dichlormid, compound of formula I+AD-67, compound of formula I+oxabetrinil, compound of formula I+cyometrinil, compound of formula I+cyometrinil Z-isomer, compound of formula I+fenclorim, compound of formula I+cyprosulfamide, compound of formula I+naphthalic anhydride, compound of formula I+flurazole, compound of formula I+CL 304,415, compound of formula I+dicyclonon, compound of formula I+fluxofenim, compound of formula I+DKA-24, compound of formula I+R-29148 and compound of formula I+PPG-1292. A safening effect can also be observed for the mixtures compound of the formula I+dymron, compound of the formula I+MCPA, compound of the formula I+mecoprop and compound of the formula I+mecoprop-P.

The above-mentioned safeners and herbicides are described, for example, in the Pesticide Manual, Twelfth Edition, British Crop Protection Council, 2000. R-29148 is described, for example by P. B. Goldsbrough et al., Plant Physiology, (2002), Vol. 130 pp. 1497-1505 and references therein, PPG-1292 is known from WO09211761 and N-(2-methoxybenzoyl)-4-[(methylaminocarbonyl)amino]benzenesulfonamide is known from EP365484. Benoxacor, cloquintocet-mexyl, cyprosulfamide, mefenpyr-diethyl and N-(2-methoxybenzoyl)-4-[(methylaminocarbonyl)amino] benzenesulfonamide are especially preferred, where cloquintocet-mexyl is particularly valuable.

The rate of application of safener relative to the herbicide is largely dependent upon the mode of application. In the case of field treatment, generally from 0.001 to 5.0 kg of safener/ha, preferably from 0.001 to 0.5 kg of safener/ha, and generally from 0.001 to 2 kg of herbicide/ha, but preferably from 0.005 to 1 kg/ha, are applied.

The herbicidal compositions according to the invention are suitable for all methods of application customary in agriculture, such as, for example, pre-emergence application, post-emergence application and seed dressing. Depending upon the intended use, the safeners can be used for pretreating the seed material of the crop plant (dressing the seed or seedlings) or introduced into the soil before or after sowing, followed by the application of the (unsafened) compound of the formula (I), optionally in combination with a co-herbicide. It can, however, also be applied alone or together with the herbicide before or after emergence of the plants. The treatment of the plants or the seed material with the safener can therefore take place in principle independently of the time of application of the herbicide. The treatment of the plant by simultaneous application of herbicide and safener (e.g. in the form of a tank mixture) is generally preferred. The rate of application of safener relative to herbicide is largely dependent upon the mode of application. In the case of field treatment, generally from 0.001 to 5.0 kg of safener/ha, preferably from 0.001 to 0.5 kg of safener/ha, are applied. In the case of seed dressing, generally from 0.001 to 10 g of safener/kg of seed, preferably from 0.05 to 2 g of safener/kg of seed, are applied. When the safener is applied in liquid form, with seed soaking, shortly before sowing, it is advantageous to use safener solutions which contain the active ingredient in a concentration of from 1 to 10 000 ppm, preferably from 100 to 1000 ppm.

It is preferred to apply the other herbicide together with one of the safeners mentioned above.

The following Examples illustrate the invention further but do not limit the invention.

PREPARATION EXAMPLES

Those skilled in the art will appreciate that certain compounds described below are β-ketoenols, and as such may exist as a single tautomer or as a mixture of keto-enol and diketone tautomers, as described, for example by J. March, Advanced Organic Chemistry, third edition, John Wiley and Sons. The compounds shown in Table T1 are drawn as an arbitrary single enol tautomer, but it should be inferred that this description covers both the diketone form and any possible enols which could arise through tautomerism. Where more than one tautomer is observed in proton NMR, the data shown are for the mixture of tautomers. Furthermore, some of the compounds shown below are drawn as single enantiomers for the purposes of simplicity, but unless specified as single enantiomers, these structures should be construed as representing a mixture of enantiomers in any ratio. Additionally, some of the compounds can exist as diastereoisomers, and it should be inferred that these can be present as a single diastereoisomer or as a mixture of diastereoisomers in any ratio. Within the detailed experimental section the diketone tautomer is chosen for naming purposes, even if the predominant tautomer is the enol form.

Example 1

Preparation of 4-[4-(4-bromo-2-fluorophenoxy)-2-ethylphenyl]-2,2,6,6-tetramethylpyran-3,5-dione

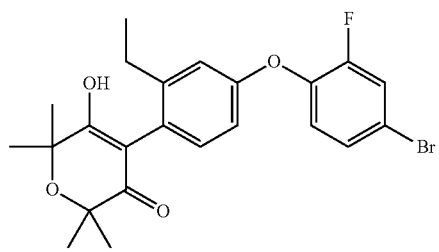 [SMILES: CCc1cc(Oc2ccc(Br)cc2F)ccc1C1=C(O)C(C)(C)OC(C)(C)C1=O]

Step 1: Preparation of 4-bromo-2-ethylphenyllead triacetate

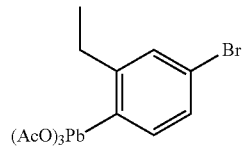

Dry chloroform (30 ml) is added to a mixture of lead tetraacetate (8.52 g, 19.3 mmol) and mercuric diacetate (0.28 g, 0.875 mmol) under an atmosphere of nitrogen, and the reaction mixture is stirred and heated to 40° C. 4-Bromo-2-ethylphenylboronic acid (4.0 g, 17.5 mmol) is added in one portion and the mixture is stirred at 40° C. for 4 hours. The reaction mixture is cooled to 0° C., and potassium carbonate (2.66 g, 19.3 mmol) is added portionwise. The mixture is stirred for 5 minutes, then filtered through a small plug of diatomaceous earth, washing with chloroform. The filtrate concentrated under reduced pressure to give 4-bromo-2-ethylphenyllead triacetate.

Step 2: Preparation of 4-(4-bromo-2-ethylphenyl)-2,2,6,6-tetramethylpyran-3,5-dione

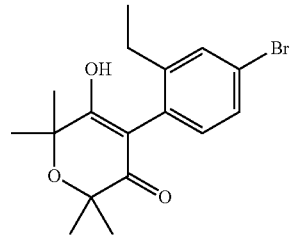 [SMILES: CCc1cc(Br)ccc1C1=C(O)C(C)(C)OC(C)(C)C1=O]

4-Dimethylaminopyridine (3.13 g, 25.7 mmol) and toluene (10 ml) are added to a solution of 2,2,6,6-tetramethylpyran-3,5-dione (0.87 g, 5.13 mmol) in chloroform (40 ml) and the reaction mixture is heated to 80° C. 4-Bromo-2-ethylphenyllead triacetate (3.50 g, 6.16 mmol) is added portionwise over 5 minutes, and once the addition is complete the reaction mixture is stirred at 80° C. for a further 4 hours. The mixture is cooled to room temperature, 2M aqueous hydrochloric acid (40 ml) is added, and the mixture is stirred vigorously for 20 minutes, then filtered through a small plug of diatomaceous earth, washing with dichloromethane (40 ml). The organic phase is separated, and the aqueous phase is extracted with dichloromethane (2×40 ml). The organic solutions are combined, dried over anhydrous magnesium sulfate, filtered and the filtrate is concentrated under reduced pressure. The residue is purified by column chromatography on silica gel to give 4-(4-bromo-2-ethylphenyl)-2,2,6,6-tetramethylpyran-3,5-dione.

Step 3: Preparation of 4-[4-(4-bromo-2-fluorophenoxy)-2-ethylphenyl]-2,2,6,6-tetramethylpyran-3,5-dione

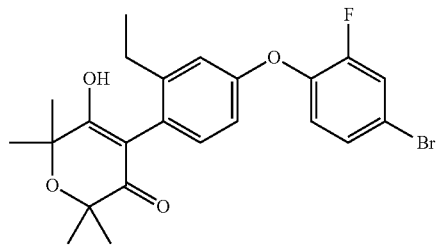 [SMILES: CCc1cc(Oc2ccc(Br)cc2F)ccc1C1=C(O)C(C)(C)OC(C)(C)C1=O]

A mixture of 4-(4-bromo-2-ethylphenyl)-2,2,6,6-tetramethylpyran-3,5-dione (0.42 g, 1.19 mmol), 4-bromo-2-fluorophenol (0.27 g, 1.43 mmol), cesium carbonate (0.78 g, 2.38 mmol), copper(II) trifluoromethanesulfonate (0.02 g, 0.06 mmol) and ethyl acetate (0.004 g, 0.06 mmol) in dry toluene (10 ml) are heated to reflux for 21 hours. The mixture is cooled to room temperature and N,N-dimethylformamide (2 ml) is added. The mixture is partitioned between 2M aqueous hydrochloric acid (10 ml) and ethyl acetate (3×10 ml). The organic extracts are combined, dried over anhydrous magnesium sulfate, filtered and the filtrate evaporated under reduced pressure. The residue is purified by preparative reverse phase HPLC to give 4-[4-(4-bromo-2-fluorophenoxy)-2-ethylphenyl]-2,2,6,6-tetramethylpyran-3,5-dione.

Example 2

Preparation of 4-[4-(4-chloro-3-fluorophenoxy)-2-ethylphenyl]-2,2,6,6-tetramethylpyran-3,5-dione

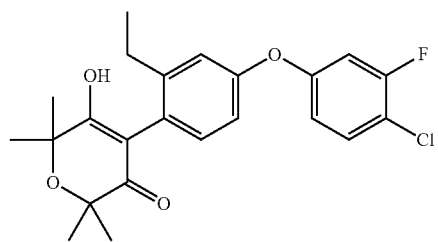 [SMILES: CCc1cc(Oc2ccc(Cl)c(F)c2)ccc1C1=C(O)C(C)(C)OC(C)(C)C1=O]

A mixture of 4-(4-bromo-2-ethylphenyl)-2,2,6,6-tetramethylpyran-3,5-dione (0.20 g, 0.57 mmol), 4-chloro-3-fluorophenol (0.41 g, 2.83 mmol), cesium carbonate (0.40 g, 1.13 mmol), copper(II) trifluoromethanesulfonate (0.01 g, 0.03 mmol) and powdered molecular sieve, 4 Å (0.40 g) in dry toluene (3.5 ml) is heated to 160° C. under microwave irradiation for 1 hour. The mixture is cooled to room temperature diluted with dichloromethane and 2M aqueous hydrochloric acid (10 ml) and passed through a phase separation cartridge. The organic phase is dried over anhydrous magnesium sulfate, filtered and the filtrate is evaporated under reduced pressure. The residue is dissolved in N,N-dimethylformamide (1 ml) and purified by preparative reverse phase HPLC to give 4-[4-(4-chloro-3-fluorophenoxy)-2-ethylphenyl]-2,2,6,6-tetramethylpyran-3,5-dione.

Example 3

Preparation of 4-[4-(5-trifluoromethylpyridin-2-yloxy)-2-ethylphenyl]-2,2,6,6-tetramethylpyran-3,5-dione

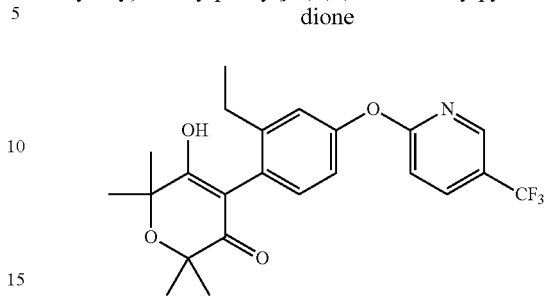

Step 1: Preparation of 4-(2-ethyl-4-hydroxyphenyl)-2,2,6,6-tetramethylpyran-3,5-dione

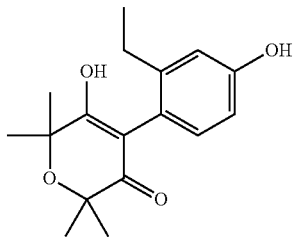 [SMILES: CCc1cc(O)ccc1C1=C(O)C(C)(C)OC(C)(C)C1=O]

A mixture of 4-(4-bromo-2-ethylphenyl)-2,2,6,6,-tetramethylpyran-3,5-dione (1.00 g, 2.8 mmol), copper(I) iodide (0.108 g, 0.57 mmol), and L-proline (0.033 g, 0.28 mmol) in 1M aqueous sodium hydroxide solution (8.8 ml) is heated at 200° C. under microwave irradiation, until the reaction is judged to be complete by LCMS. The mixture is cooled to room temperature, diluted with ethyl acetate and 2 M aqueous hydrochloric acid and filtered through a plug of diatomaceous earth, washing with ethyl acetate. The organic phase is collected, and the aqueous phase is extracted with ethyl acetate. The organic solutions are combined, washed with brine, dried over anhydrous magnesium sulfate, filtered and the filtrate is evaporated under reduced pressure. The residue is purified by column chromatography on silica gel to give 4-(2-ethyl-4-hydroxyphenyl)-2,2,6,6-tetramethylpyran-3,5-dione.

Step 2: Preparation of 4-[4-(5-trifluoromethylpyridin-2-yloxy)-2-ethylphenyl]-2,2,6,6-tetramethylpyran-3,5-dione

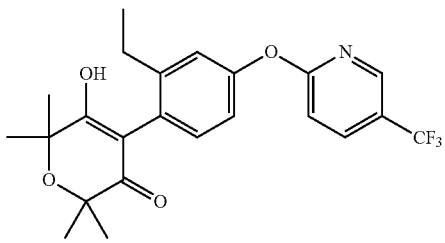 [SMILES: CCc1cc(Oc2ccc(C(F)(F)F)cn2)ccc1C1=C(O)C(C)(C)OC(C)(C)C1=O]

4-(2-Ethyl-4-hydroxyphenyl)-2,2,6,6-tetramethylpyran-3,5-dione (0.100 g, 0.34 mmol) is added to a mixture of 2-fluoro-5-trifluoromethylpyridine (0.061 g, 0.41 mmol) and potassium carbonate (0.110 g, 0.69 mmol) in N,N-dimethylformamide (2 ml), and the mixture is heated at 140° C. under microwave irradiation for 1 hour. The mixture is cooled to room temperature, then acidified by addition of 2M aqueous hydrochloric acid. The mixture is diluted with dichloromethane and passed through a phase separation cartridge. The organic phase is concentrated to around 2 ml, and purified by preparative reverse phase HPLC to give 4-[4-(5-trifluoromethylpyridin-2-yloxy)-2-ethylphenyl]-2,2,6,6-tetramethylpyran-3,5-dione.

Example 4

Preparation of 4-[4-(6-chloroquinoxalin-2-yloxy)-2-ethylphenyl]-2,2,6,6-tetramethylpyran-3,5-dione

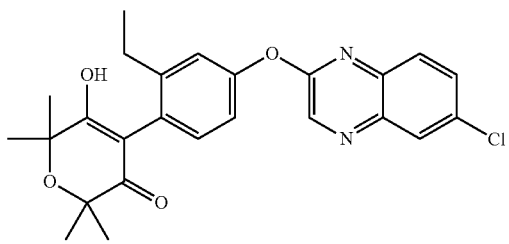 [SMILES: CCc1cc(Oc2cnc3cc(Cl)ccc3n2)ccc1C1=C(O)C(C)(C)OC(C)(C)C1=O]

4-(2-Ethyl-4-hydroxyphenyl)-2,2,6,6-tetramethylpyran-3,5-dione (0.100 g, 0.34 mmol) is added to a mixture of 2,6-dichloroquinoxaline (0.081 g, 0.41 mmol) and potassium carbonate (0.110 g, 0.69 mmol) in N,N-dimethylformamide (3 ml), and the mixture is heated at 140° C. under microwave irradiation for 40 minutes. The mixture is cooled to room temperature, then acidified by addition of 2M aqueous hydrochloric acid. The mixture is diluted with dichloromethane and passed through a phase separation cartridge. The organic phase is concentrated to around 2 ml, and purified by preparative reverse phase HPLC to give 4-[4-(6-choroquinoxalin-2-yloxy)-2-ethylphenyl]-2,2,6,6-tetramethylpyran-3,5-dione.

Example 5

Preparation of 2-[4-(6-chloroquinolin-3-yloxy)-2,6-dimethylphenyl]cyclohexane-1,3-dione

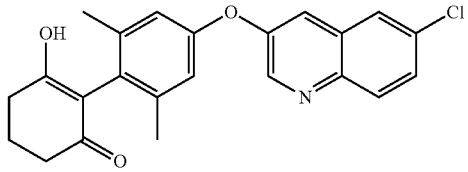

Step 1: Preparation of 4-benzyloxy-2,6-dimethylphenyl lead triacetate

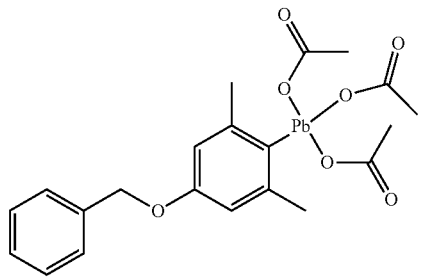

Lead tetraacetate (5.7 g, 0.013 mol) and mercury (II) acetate (0.2 g, 0.0006 mol) are stirred together and thoroughly flushed with nitrogen. Chloroform (20 ml) is added and the dark orange solution heated to 50° C., followed by the addition of 4-benzyloxy-2,6-dimethylphenyl boronic acid (3 g, 0.012 mol) in one portion. After further heating at 50° C. for 3 hours the reaction mixture is cooled to 0° C. and potassium carbonate added (1.9 g, 0.02 mol). The suspension is stirred for just 5 minutes before filtering and evaporation of the crude solution under reduced pressure. The crude product is then azeotroped with diethyl ether to afford 4-benzyloxy-2,6-dimethylphenyl lead triacetate as a pale solid.

Step 2: Preparation of 2-(4-benzyloxy-2,6-dimethylphenyl)cyclohexane-1,3-dione

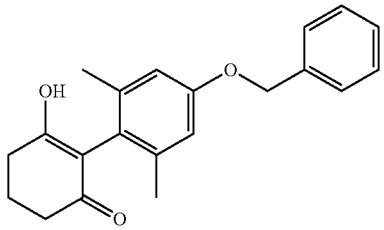 [SMILES: Cc1cc(OCc2ccccc2)cc(C)c1C1=C(O)CCCC1=O]

A solution of 4-benzyloxy-2,6-dimethylphenyl leadtriacetate (3.12 g, 0.005 mol), cyclohexane-1,3-dione (0.58 g, 0.005 mol), 4-(dimethylamino)pyridine (2.9 g, 0.024 mol), chloroform (30 ml) and toluene (12 ml) are heated at 80'C for 20 hours. After cooling to room temperature the reaction is dilluted with dichloromethane (50 ml) and quenched with 2M hydrochloric acid (50 ml). The resulting precipitate is filtered through diatomaceous earth and the organic phase is separated, washed with 2M hydrochloric acid (50 ml) then dried over magnesium sulfate and evaporated under reduced pressure. The crude product is finally purified by flash column chromatography on silica gel (1:1 ethyl acetate/hexane eluant) to afford 2-(4-benzyloxy-2,6-dimethylphenyl)cyclohexane-1,3-dione as a cream solid.

Step 3: Preparation of 2-(4-hydroxy-2,6-dimethylphenyl)cyclohexane-1,3-dione

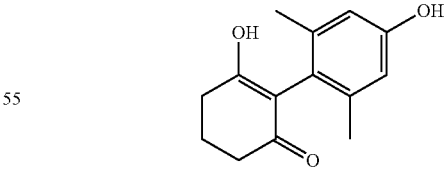

To a solution of 2-(4-benzyloxy-2,6-dimethylphenyl)cyclohexane-1,3-dione (0.57 g, 0.0018 mol) in ethyl acetate (30 ml) and methanol (530 ml) is added 5% palladium on carbon (0.100 g), and the suspension is then stirred under 4 bar hydrogen pressure for 5 hours. The suspension is filtered through diatomaceous earth and the filtrate evaporated under reduced pressure to afford 2-(4-hydroxy-2,6-dimethylphenyl)cyclohexane-1,3-dione as a grey solid.

Step 4: Preparation of 2-[4-(6-chloroquinolin-3-yloxy)-2,6-dimethylphenyl]cyclohexane-1,3-dione

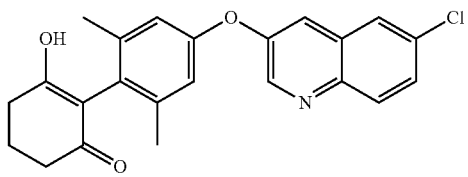 [SMILES: Cc1cc(Oc2cnc3ccc(Cl)cc3c2)cc(C)c1C1=C(O)CCCC1=O]

To a mixture of 2-(4-hydroxy-2,6-dimethylphenyl)cyclohexane-1,3-dione (0.200 g, 0.0009 mol), 2,6-dichloroquinoline (0.170 g, 0.0009 mol) and potassium carbonate (0.350 g, 0.0025 mol) is added N,N-dimethylformamide (3 ml), and the mixture is heated at 140° C. for 40 minutes under microwave irradiation. The reaction mixture is then diluted with ethyl acetate (20 ml) and 2M hydrochloric acid (20 ml), and the organic phase is separated, dried over magnesium sulfate and evaporated under reduced pressure. The crude product is purified by preparative reverse phase HPLC to afford 2-[4-(6-chloroquinolin-3-yloxy)-2,6-dimethylphenyl]cyclohexane-1,3-dione as a cream solid.

Additional compounds in Table T1 below are prepared by similar methods using appropriate starting materials.

TABLE T1

| Compound Number | Structure | $^1$H NMR (CDCl$_3$ unless stated) or other physical data |
|---|---|---|
| A-1 | 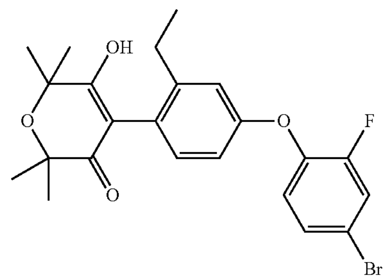 [SMILES: CCc1cc(Oc2ccc(Br)cc2F)ccc1C1=C(O)C(C)(C)OC(C)(C)C1=O] | δ 7.38 (dd, 1H), 7.27 (m, 1H), 7.05-6.94 (m, 3H), 6.83 (dd, 1H), 5.61 (br. s, 1H), 2.40 (m, 2H), 1.59 (s, 6H), 1.48 (d, 6H), 1.09 (t, 3H). |
| A-2 | 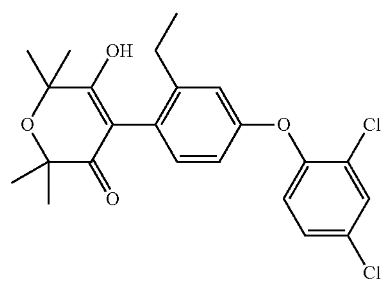 | δ 7.47 (d, 1H), 7.20 (dd, 1H), 7.01-6.97 (m, 2H), 6.93 (d, 1H), 6.78 (dd, 1H), 5.76 (br. s, 1H), 2.38-2.36 (br. m, 2H), 1.57-1.46 (br. m, 12H), 1.07 (t, 3H). |
| A-3 | 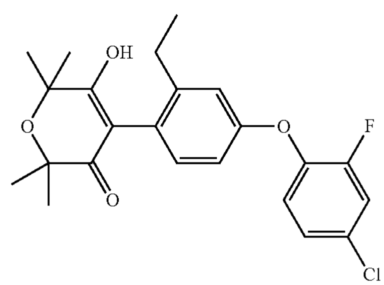 [SMILES: CCc1cc(Oc2ccc(Cl)cc2F)ccc1C1=C(O)C(C)(C)OC(C)(C)C1=O] | δ 7.21 (dd, 1H), 7.12-7.09 (m, 1H), 7.04 (t, 1H), 6.99 (d, 1H), 6.93 (d, 1H), 6.79 (dd, 1H), 5.60 (br. s, 1H), 2.37 (q, 2H), 1.51-1.46 (br. m, 12H), 1.06 (t, 3H). |
| A-4 | 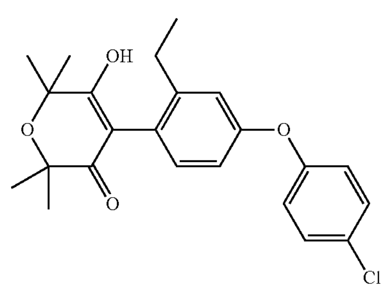 [SMILES: CCc1cc(Oc2ccc(Cl)cc2)ccc1C1=C(O)C(C)(C)OC(C)(C)C1=O] | δ 7.32-7.29 (m, 2H), 7.03-6.97 (m, 4H), 6.86 (dd, 1H), 5.61 (br. s, 1H), 2.42-2.35 (m, 2H), 1.59 (br. s, 6H), 1.47 (br. s, 6H), 1.08 (t, 3H). |

TABLE T1-continued

| Compound Number | Structure | ¹H NMR (CDCl₃ unless stated) or other physical data |
|---|---|---|
| A-5 | 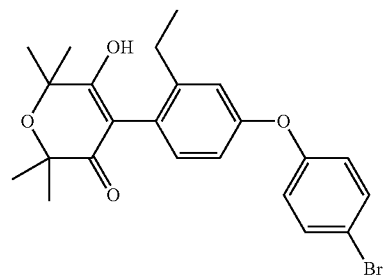 [SMILES: CCc1cc(Oc2ccc(Br)cc2)ccc1C1=C(O)C(C)(C)OC(C)(C)C1=O] | δ 7.44 (d, 2H), 7.01 (d, 1H), 6.97 (d, 1H), 6.92 (d, 2H), 6.85 (dd, 1H), 5.81 (br. s, 1H), 2.42-2.34 (m, 2H), 1.58 (s, 6H), 1.46 (d, 6H), 1.07 (t, 3H). |
| A-6 | 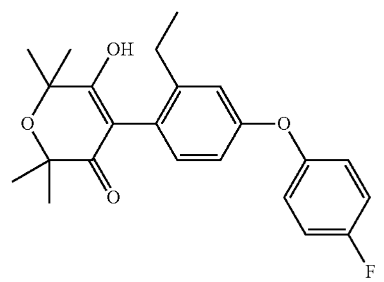 [SMILES: CCc1cc(Oc2ccc(F)cc2)ccc1C1=C(O)C(C)(C)OC(C)(C)C1=O] | δ 7.06-6.97 (m, 5H), 6.93 (d, 1H), 6.80 (dd, 1H), 5.94 (br. s, 1H), 2.41-2.33 (m, 2H), 1.57 (s, 6H), 1.45 (d, 6H), 1.06 (t, 3H). |
| A-7 | 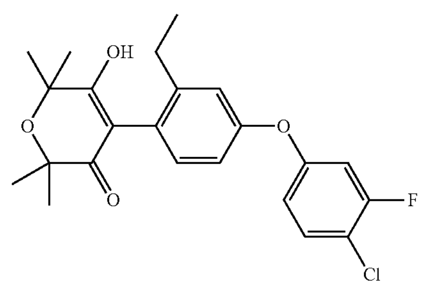 [SMILES: CCc1cc(Oc2ccc(Cl)c(F)c2)ccc1C1=C(O)C(C)(C)OC(C)(C)C1=O] | δ 7.33 (t, 1H), 7.06 (d, 1H), 7.00 (d, 1H), 6.90 (dd, 1H), 6.85 (dd, 1H), 6.79-6.77 (m, 1H), 5.59 (br. s, 1H), 2.44-2.37 (m, 2H), 1.59 (br. s, 6H), 1.47 (br. s, 6H), 1.09 (t, 3H). |
| A-8 | 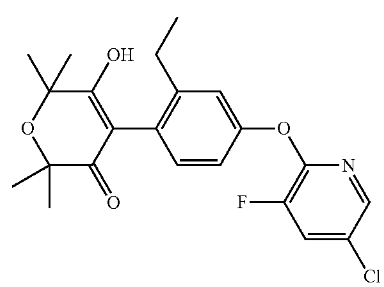 [SMILES: CCc1cc(Oc2ncc(Cl)cc2F)ccc1C1=C(O)C(C)(C)OC(C)(C)C1=O] | δ 7.78 (d, 1H), 7.53 (dd, 1H), 7.12-7.08 (m, 2H), 7.01 (dd, 1H), 2.47-2.40 (m, 2H), 1.95 (br. s, 1H), 1.58 (s, 6H), 1.47 (d, 6H), 1.11 (t, 3H). |
| A-9 | 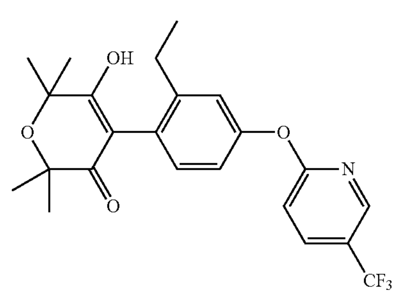 [SMILES: CCc1cc(Oc2ccc(C(F)(F)F)cn2)ccc1C1=C(O)C(C)(C)OC(C)(C)C1=O] | δ 8.36 (s, 1H), 7.95 (dd, 1H), 7.15-7.09 (m, 3H), 7.02 (dd, 1H), 2.44 (q, 2H), 1.54 (s, 12H), 1.11 (t, 3H). |

TABLE T1-continued

| Compound Number | Structure | $^1$H NMR (CDCl$_3$ unless stated) or other physical data |
|---|---|---|
| A-10 | 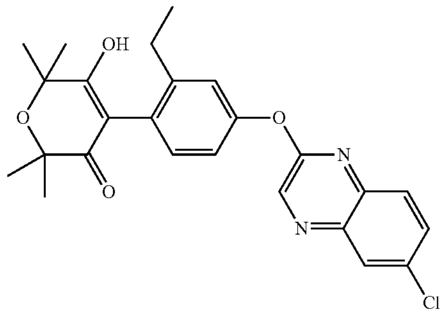 [SMILES: CCc1cc(Oc2cnc3cc(Cl)ccc3n2)ccc1C1=C(O)C(C)(C)OC(C)(C)C1=O] | δ .68 (s, 1H), 8.05 (d, 1H), 7.67-7.65 (m, 1H), 7.61-7.58 (m, 1H), 7.19-7.18 (m, 1H), 7.16-7.15 (m, 2H), 2.48-2.45 (br. m, 2H), 1.66-1.46 (1br. m, 2H), 1.13 (t, 3H). |
| A-11 | 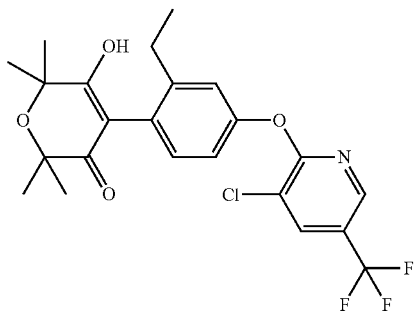 [SMILES: CCc1cc(Oc2ncc(C(F)(F)F)cc2Cl)ccc1C1=C(O)C(C)(C)OC(C)(C)C1=O] | δ 8.18 (s, 1H), 7.99 (d, 1H), 7.15-7.11 (m, 2H), 7.04 (dd, 1H), 2.45-2.44 (br. m, 2H), 1.56-1.44 (br. m, 12H), 1.12 (t, 3H) |
| A-12 | 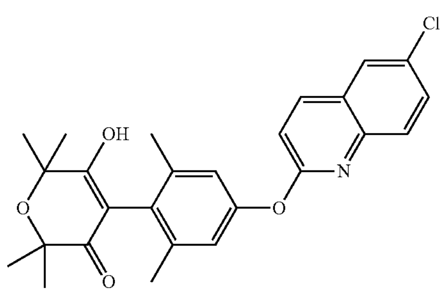 | δ 8.06 (d, 1H), 7.75 (m, 1H), 7.67 (d, 1H), 7.53 (m, 1H), 7.20 (d, 1H), 6.96 (s, 2H), 2.14 (s, 6H), 1.62 (br.s, 6H), 1.52 (br.s, 6H) |
| A-13 | 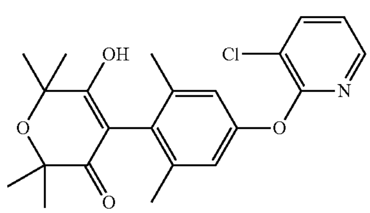 [SMILES: Cc1cc(Oc2ncccc2Cl)cc(C)c1C1=C(O)C(C)(C)OC(C)(C)C1=O] | δ 7.90 (m, 1H), 7.75 (d, 1H), 6.97 (m, 1H), 6.90 (s, 2H), 2.12 (s, 6H), 1.60 (s, 6H), 1.50 (s, 6H) |
| A-14 | 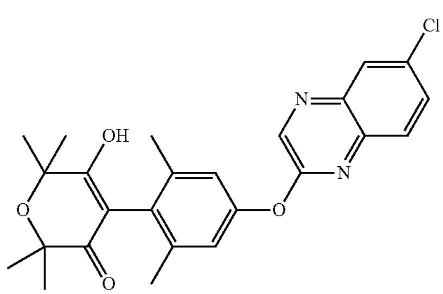 [SMILES: Cc1cc(Oc2cnc3cc(Cl)ccc3n2)cc(C)c1C1=C(O)C(C)(C)OC(C)(C)C1=O] | δ 8.61 (s, 1H), 8.01 (m, 1H), 7.66 (d, 1H), 7.60 (m, 1H), 6.95 (s, 2H), 2.13 (s, 6H), 1.64 (br.s, 6H), 1.51 (br.s, 6H) |

TABLE T1-continued

| Compound Number | Structure | $^1$H NMR (CDCl$_3$ unless stated) or other physical data |
|---|---|---|
| A-15 | 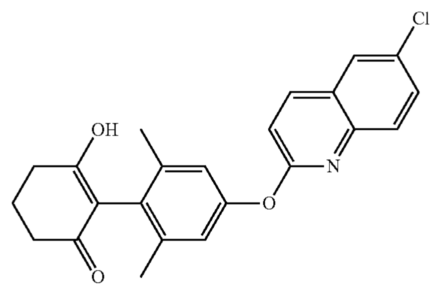 [SMILES: Cc1cc(Oc2ccc3cc(Cl)ccc3n2)cc(C)c1C1=C(O)CCCC1=O] | δ 8.05 (d, 1H), 7.70 (m, 1H), 7.67 (d, 1H), 7.52 (m, 1H), 7.17 (d, 1H), 6.95 (s, 2H), 2.60 (m, 4H), 2.14 (m, 2H), 2.11 (s, 6H) |
| A-16 | 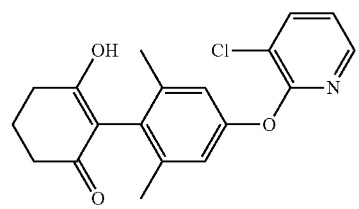 [SMILES: Cc1cc(Oc2ncccc2Cl)cc(C)c1C1=C(O)CCCC1=O] | δ 7.93 (m, 1H), 7.77 (d, 1H), 6.98 (m, 1H), 6.89 (s, 2H), 2.58 (m, 4H), 2.14 (m, 2H), 2.11 (s, 6H) |
| A-17 | 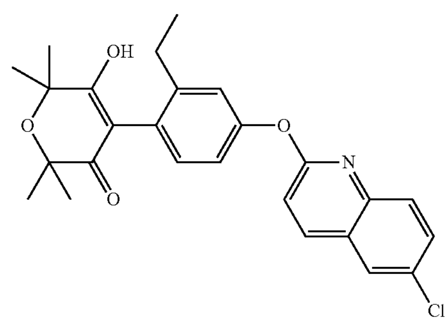 [SMILES: CCc1cc(Oc2ccc3cc(Cl)ccc3n2)ccc1C1=C(O)C(C)(C)OC(C)(C)C1=O] | δ 8.08 (d, 1H), 7.76 (d, 1H), 7.68 (d, 1H), 7.54-7.51 (m, 1H), 7.20-7.10 (m, 4H), 2.48 (q, 2H), 1.57 (s, 12H), 1.14 (t, 3H). |
| A-18 | 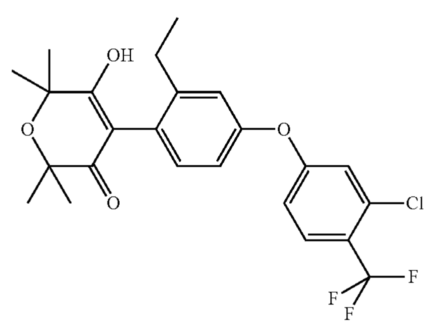 [SMILES: CCc1cc(Oc2ccc(C(F)(F)F)c(Cl)c2)ccc1C1=C(O)C(C)(C)OC(C)(C)C1=O] | δ 7.64 (d, 1H), 7.17 (d, 1H), 7.12 (d, 1H), 7.07 (d, 1H), 6.99-6.95 (m, 2H), 2.46-2.42 (br. m, 2H), 1.62-1.50 (br. d, 12H), 1.12 (t, 3H). |
| A-19 | 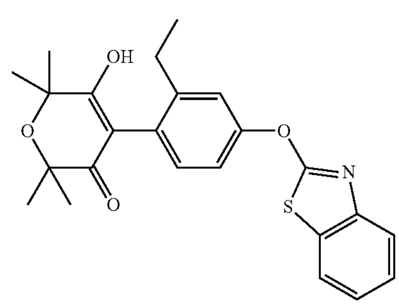 [SMILES: CCc1cc(Oc2nc3ccccc3s2)ccc1C1=C(O)C(C)(C)OC(C)(C)C1=O] | δ 7.69 (d, 1H), 7.63 (d, 1H), 7.40-7.36 (m, 1H), 7.31-7.23 (m, 3H), 7.17-7.15 (m, 1H), 2.49-2.46 (br. m, 2H), 1.55 (br. d, 12H), 1.14 (t, 3H). |

TABLE T1-continued

| Compound Number | Structure | $^1$H NMR (CDCl$_3$ unless stated) or other physical data |
|---|---|---|
| A-20 | 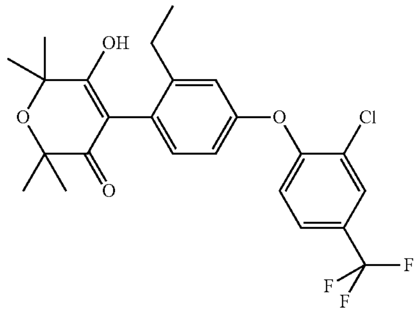 [SMILES: CCc1cc(Oc2ccc(C(F)(F)F)cc2Cl)ccc1C1=C(O)C(C)(C)OC(C)(C)C1=O] | δ 7.76 (d, 1H), 7.49-7.46 (m, 1H), 7.10-7.07 (m, 2H), 7.04 (d, 1H), 6.91 (dd, 1H), 2.47-2.39 (m, 2H), 1.61 (s, 6H), 1.49 (s, 6H), 1.11 (t, 3H). |

It should be noted that certain compounds of the invention exist as a mixture in any ratio of isomers, including atropisomers, noted above, under the conditions used to obtain the $^1$H NMR data. Where this has occurred, the characterising data are reported for all isomers present at ambient temperature in the specified solvent. Unless otherwise stated, proton NMR spectra were recorded at ambient temperature.

The compounds of the following Tables 1 to 57 can be obtained in an analogous manner. Table 1 covers compounds of the following type

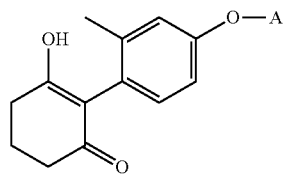

wherein A is as defined in Table 1.

TABLE 1

| Compound Number | A | Compound Number | A |
|---|---|---|---|
| 1.001 | phenyl | 1.002 | 2-bromophenyl |
| 1.003 | 2-chlorophenyl | 1.004 | 2-cyanophenyl |
| 1.005 | 2-difluoromethoxyphenyl | 1.006 | 2-fluorophenyl |
| 1.007 | 2-methoxyphenyl | 1.008 | 2-methylphenyl |
| 1.009 | 2-nitrophenyl | 1.010 | 2-trifluoromethoxyphenyl |
| 1.011 | 2-trifluoromethylphenyl | 1.012 | 3-bromophenyl |
| 1.013 | 3-chlorophenyl | 1.014 | 3-cyanophenyl |
| 1.015 | 3-difluoromethoxyphenyl | 1.016 | 3-fluorophenyl |
| 1.017 | 3-methoxyphenyl | 1.018 | 3-methylphenyl |
| 1.019 | 3-nitrophenyl | 1.020 | 3-trifluoromethoxyphenyl |
| 1.021 | 3-trifluoromethylphenyl | 1.022 | 4-bromophenyl |
| 1.023 | 4-chlorophenyl | 1.024 | 4-cyanophenyl |
| 1.025 | 4-difluoromethoxyphenyl | 1.026 | 4-fluorophenyl |
| 1.027 | 4-methanesulfonyl | 1.028 | 4-methoxyphenyl |
| 1.029 | 4-methylphenyl | 1.030 | 4-nitrophenyl |
| 1.031 | 4-trifluoromethoxyphenyl | 1.032 | 4-trifluoromethylphenyl |
| 1.033 | 4-bromo-2-chlorophenyl | 1.034 | 2,4-dichlorophenyl |
| 1.035 | 2-chloro-4-cyanophenyl | 1.036 | 2-chloro-4-difluoromethoxyphenyl |
| 1.037 | 2-chloro-4-fluorophenyl | 1.038 | 2-chloro-4-methoxyphenyl |
| 1.039 | 2-chloro-4-methylphenyl | 1.040 | 2-chloro-4-nitrophenyl |
| 1.041 | 2-chloro-4-trifluoromethoxyphenyl | 1.042 | 2-chloro-4-trifluoromethylphenyl |
| 1.043 | 4-bromo-3-chlorophenyl | 1.044 | 3,4-dichlorophenyl |
| 1.045 | 3-chloro-4-cyanophenyl | 1.046 | 3-chloro-4-difluoromethoxyphenyl |
| 1.047 | 3-chloro-4-fluorophenyl | 1.048 | 3-chloro-4-methoxyphenyl |
| 1.049 | 3-chloro-4-methylphenyl | 1.050 | 3-chloro-4-nitrophenyl |
| 1.051 | 3-chloro-4-trifluoromethoxyphenyl | 1.052 | 3-chloro-4-trifluoromethylphenyl |
| 1.053 | 2-bromo-4-chlorophenyl | 1.054 | 4-chloro-2-difluoromethoxyphenyl |
| 1.055 | 4-chloro-2-cyanophenyl | 1.056 | 4-chloro-2-methoxyphenyl |
| 1.057 | 4-chloro-2-fluorophenyl | 1.058 | 4-chloro-2-nitrophenyl |
| 1.059 | 4-chloro-2-methylphenyl | 1.060 | 4-chloro-2-trifluoromethylphenyl |
| 1.061 | 4-chloro-2-trifluoromethoxyphenyl | 1.062 | 4-chloro-3-trifluoromethoxyphenyl |
| 1.063 | 3-bromo-4-chlorophenyl | 1.064 | 4-chloro-3-difluoromethoxyphenyl |
| 1.065 | 4-chloro-3-cyanophenyl | 1.066 | 4-chloro-3-methoxyphenyl |
| 1.067 | 4-chloro-3-fluorophenyl | 1.068 | 4-chloro-3-nitrophenyl |
| 1.069 | 4-chloro-3-methylphenyl | 1.070 | 4-chloro-3-trifluoromethylphenyl |
| 1.071 | 4-bromo-2-fluorophenyl | 1.072 | 2-difluoro-4-difluoromethoxyphenyl |
| 1.073 | 4-cyano-2-fluorophenyl | 1.074 | 2-fluoro-4-methoxyphenyl |
| 1.075 | 2,4-fluorophenyl | 1.076 | 2-fluoro-4-nitrophenyl |
| 1.077 | 2-fluoro-4-methylphenyl | 1.078 | 2-fluoro-4-trifluoromethylphenyl |
| 1.079 | 2-fluoro-4-trifluoromethoxyphenyl | 1.080 | 4-bromo-3-fluorophenyl |
| 1.081 | 4-cyano-3-fluorophenyl | 1.082 | 3-difluoro-4-difluoromethoxyphenyl |

TABLE 1-continued

| Compound Number | A | Compound Number | A |
|---|---|---|---|
| 1.083 | 3,4-fluorophenyl | 1.084 | 3-fluoro-4-methoxyphenyl |
| 1.085 | 3-fluoro-4-methylphenyl | 1.086 | 3-fluoro-4-nitrophenyl |
| 1.087 | 3-fluoro-4-trifluoromethoxyphenyl | 1.088 | 3-fluoro-4-trifluoromethylphenyl |
| 1.089 | 4-chloro-2,3-difluorophenyl | 1.090 | 4-chloro-2,5-difluorophenyl |
| 1.091 | 4-chloro-2,6-difluorophenyl | 1.092 | 4-chloro-3,5-difluorophenyl |
| 1.093 | 2,4-dichloro-3-fluorophenyl | 1.094 | 2,4-dichloro-5-fluorophenyl |
| 1.095 | 2,4-dichloro-6-fluorophenyl | 1.096 | 2,3,4-trifluorophenyl |
| 1.097 | 2,4,6-trifluorophenyl | 1.098 | 2,4,5-trifluorophenyl |
| 1.099 | 3,4,5-trifluorophenyl | 1.100 | pentafluorophenyl |
| 1.101 | 2-bromo-4-cyanophenyl | 1.102 | 3-bromo-4-cyanophenyl |
| 1.103 | 4-bromo-2-cyanophenyl | 1.104 | 4-bromo-3-cyanophenyl |
| 1.105 | 2-cyano-4-nitrophenyl | 1.106 | 3-cyano-4-nitrophenyl |
| 1.107 | 2-cyano-4-trifluoromethylphenyl | 1.108 | 3-cyano-4-trifluoromethylphenyl |
| 1.109 | 2,4-dicyanophenyl | 1.110 | 3,4-dicyanophenyl |
| 1.111 | 3-chloropyridin-2-yl | 1.112 | 4-chloropyridin-2-yl |
| 1.113 | 5-chloropyridin-2-yl | 1.114 | 6-chloropyridin-2-yl |
| 1.115 | 2-chloropyridin-3-yl | 1.116 | 4-chloropyridin-3-yl |
| 1.117 | 5-chloropyridin-3-yl | 1.118 | 6-chloropyridin-3-yl |
| 1.119 | 2-chloropyridin-4-yl | 1.120 | 3-chloropyridin-4-yl |
| 1.121 | 3,4-dichloropyridin-2-yl | 1.122 | 3,5-dichloropyridin-2-yl |
| 1.123 | 3,6-dichloropyridin-2-yl | 1.124 | 2,5-dichloropyridin-3-yl |
| 1.125 | 2,6-dichloropyridin-3-yl | 1.126 | 2,3-dichloropyridin-4-yl |
| 1.127 | 2,5-dichloropyridin-4-yl | 1.128 | 3,5,6-trichloropyridin-2-yl |
| 1.129 | 3-fluoropyridin-2-yl | 1.130 | 4-fluoropyridin-2-yl |
| 1.131 | 5-fluoropyridin-2-yl | 1.132 | 6-fluoropyridin-2-yl |
| 1.133 | 2-fluoropyridin-3-yl | 1.134 | 4-fluoropyridin-3-yl |
| 1.135 | 5-fluoropyridin-3-yl | 1.136 | 6-fluoropyridin-3-yl |
| 1.137 | 2-fluoropyridin-4-yl | 1.138 | 3-fluoropyridin-4-yl |
| 1.139 | 3,4-difluoropyridin-2-yl | 1.140 | 3,5-difluoropyridin-2-yl |
| 1.141 | 3,6-difluoropyridin-2-yl | 1.142 | 2,5-difluoropyridin-3-yl |
| 1.143 | 2,6-difluoropyridin-3-yl | 1.144 | 2,3-difluoropyridin-4-yl |
| 1.145 | 2,5-difluoropyridin-4-yl | 1.146 | 3,5,6-trifluoropyridin-2-yl |
| 1.147 | 3-trifluoromethylpyridin-2-yl | 1.148 | 4-trifluoromethylpyridin-2-yl |
| 1.149 | 5-trifluoromethylpyridin-2-yl | 1.150 | 6-trifluoromethylpyridin-2-yl |
| 1.151 | 2-trifluoromethylpyridin-3-yl | 1.152 | 4-trifluoromethylpyridin-3-yl |
| 1.153 | 5-trifluoromethylpyridin-3-yl | 1.154 | 6-trifluoromethylpyridin-3-yl |
| 1.155 | 2-trifluoromethylpyridin-4-yl | 1.156 | 3-trifluoromethylpyridin-4-yl |
| 1.157 | 4-chloro-3-fluoropyridin-2-yl | 1.158 | 5-chloro-3-fluoropyridin-2-yl |
| 1.159 | 6-chloro-3-fluoropyridin-2-yl | 1.160 | 3-chloro-4-fluoropyridin-2-yl |
| 1.161 | 3-chloro-5-fluoropyridin-2-yl | 1.162 | 3-chloro-6-fluoropyridin-2-yl |
| 1.163 | 3-chloro-5-trifluoromethylpyridin-2-yl | 1.164 | 3-fluoro-5-trifluoromethylpyridin-2-yl |
| 1.165 | 6-fluoro-3,4,5-trichloropyridin-2-yl | 1.166 | 4-methyl-3,5,6-trifluoropyridin-2-yl |
| 1.167 | pyrimidin-2-yl | 1.168 | 5-fluoropyrimidin-2-yl |
| 1.169 | 5-chloropyrimidin-2-yl | 1.170 | 5-bromopyrimidin-2-yl |
| 1.171 | 6-chloropyridazin-3-yl | 1.172 | 6-bromopyridazin-3-yl |
| 1.173 | quinoline-2-yl | 1.174 | 6-fluoroquinolin-2-yl |
| 1.175 | 7-fluoroquinolin-2-yl | 1.176 | 6-chloroquinolin-2-yl |
| 1.177 | 7-chloroquinolin-2-yl | 1.178 | 6-bromoquinolin-2-yl |
| 1.179 | 7-bromoquinolin-2-yl | 1.180 | 6-trifluoromethylquinolin-2-yl |
| 1.181 | 7-trifluoromethylquinolin-2-yl | 1.182 | quinoxalin-2-yl |
| 1.183 | 6-fluoroquinoxazin-2-yl | 1.184 | 7-fluoroquinoxalin-2-yl |
| 1.185 | 6-chloroquinoxalin-2-yl | 1.186 | 7-chloroquinoxalin-2-yl |
| 1.187 | 6-bromoquinoxalin-2-yl | 1.188 | 7-bromoquinoxalin-2-yl |
| 1.189 | 6-trifluoromethylquinoxalin-2-yl | 1.190 | 7-trifluoromethylquinoxalin-2-yl |
| 1.191 | quinazolin-2-yl | 1.192 | 6-fluoroquinazolin-2-yl |
| 1.193 | 7-fluoroquinazolin-2-yl | 1.194 | 6-chloroquinazolin-2-yl |
| 1.195 | 7-chloroquinazolin-2-yl | 1.196 | 6-bromoquinazolin-2-y |
| 1.197 | 7-bromoquinazolin-2-yl | 1.198 | benzoxazol-2-yl |
| 1.199 | 5-fluorobenzoxazol-2-yl | 1.200 | 6-fluorobenzoxazol-2-yl |
| 1.201 | 5-chlorobenzoxazol-2-yl | 1.202 | 6-chlorobenzoxazol-2-yl |
| 1.203 | 5-bromobenzoxazol-2-yl | 1.204 | 6-bromobenzoxazol-2-yl |
| 1.205 | 5-trifluoromethylbenzoxazol-2-yl | 1.206 | 6-trifluoromethylbenzoxazol-2-yl |
| 1.207 | benzothiazol-2-yl | 1.208 | 5-fluorobenzothiazol-2-yl |
| 1.209 | 6-fluorobenzothiazol-2-yl | 1.210 | 5-chlorobenzothiazol-2-yl |
| 1.211 | 6-chlorobenzothiazol-2-yl | 1.212 | 5-bromobenzothiazol-2-yl |
| 1.213 | 6-bromobenzothiazol-2-yl | 1.214 | 5-trifluoromethylbenzothiazol-2-yl |
| 1.215 | 6-trifluoromethylbenzothiazol-2-yl | 1.216 | benzo[1,2,4]triazin-3-yl |
| 1.217 | 6-fluorobenzo[1,2,4]triazin-3-yl | 1.218 | 7-fluorobenzo[1,2,4]triazin-3-yl |
| 1.219 | 6-chlorobenzo[1,2,4]triazin-3-yl | 1.220 | 7-chlorobenzo[1,2,4]triazin-3-yl |
| 1.221 | 6-bromobenzo[1,2,4]triazin-3-yl | 1.222 | 7-bromo benzo[1,2,4]triazin-3-yl |

Table 2 covers compounds of the following type

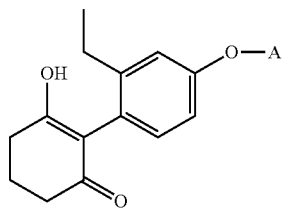

wherein A is as defined in Table 1.

Table 3 covers compounds of the following type

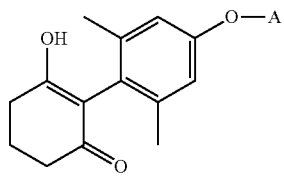

wherein A is as defined in Table 1.

Table 4 covers compounds of the following type

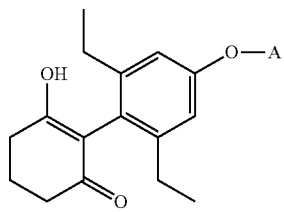

wherein A is as defined in Table 1.

Table 5 covers compounds of the following type

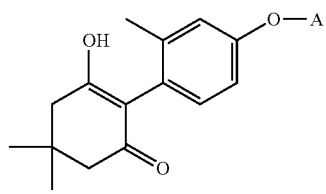

wherein A is as defined in Table 1.

Table 6 covers compounds of the following type

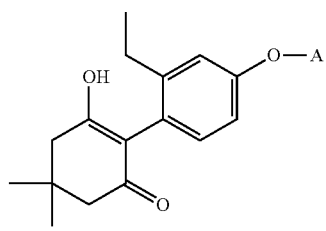

wherein A is as defined in Table 1.

Table 7 covers compounds of the following type

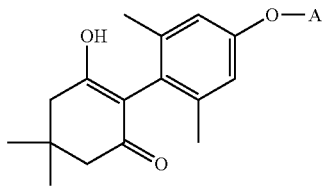

wherein A is as defined in Table 1.

Table 8 covers compounds of the following type

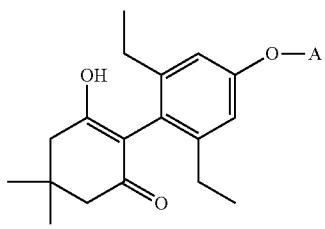

wherein A is as defined in Table 1.

Table 9 covers compounds of the following type

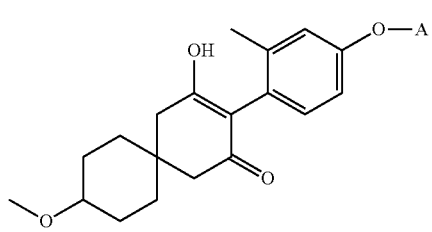

wherein A is as defined in Table 1.

Table 10 covers compounds of the following type

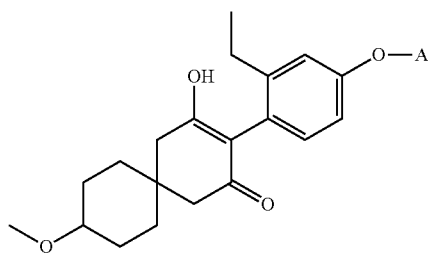

wherein A is as defined in Table 1.

Table 11 covers compounds of the following type

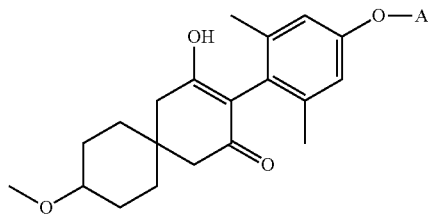

wherein A is as defined in Table 1.

Table 12 covers compounds of the following type

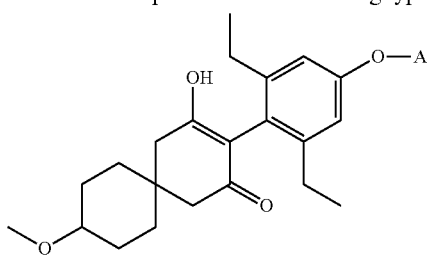

wherein A is as defined in Table 1.

Table 13 covers compounds of the following type

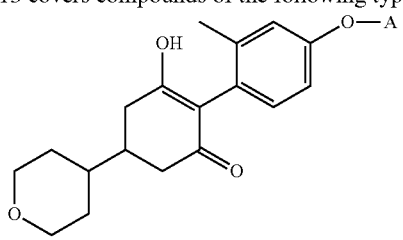

wherein A is as defined in Table 1.

Table 14 covers compounds of the following type

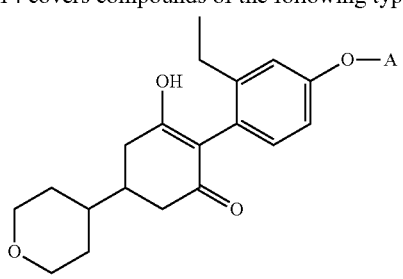

wherein A is as defined in Table 1.

Table 15 covers compounds of the following type

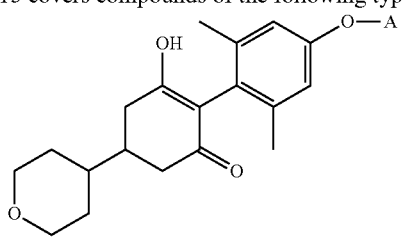

wherein A is as defined in Table 1.

Table 16 covers compounds of the following type

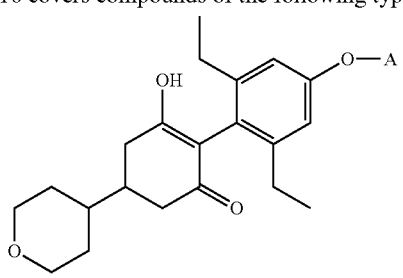

wherein A is as defined in Table 1.

Table 17 covers compounds of the following type

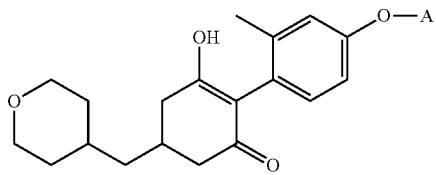

wherein A is as defined in Table 1.

Table 18 covers compounds of the following type

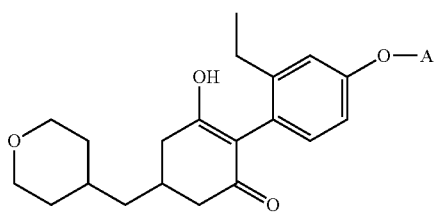

wherein A is as defined in Table 1.

Table 19 covers compounds of the following type

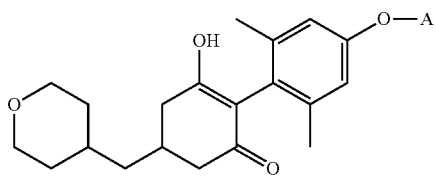

wherein A is as defined in Table 1.

Table 20 covers compounds of the following type

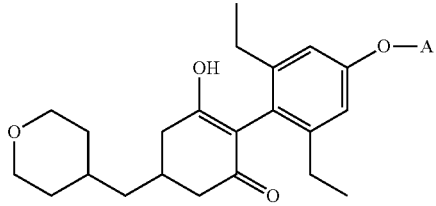

wherein A is as defined in Table 1.

Table 21 covers compounds of the following type

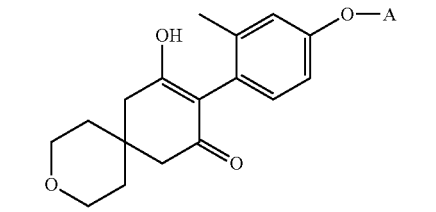

wherein A is as defined in Table 1.

Table 22 covers compounds of the following type

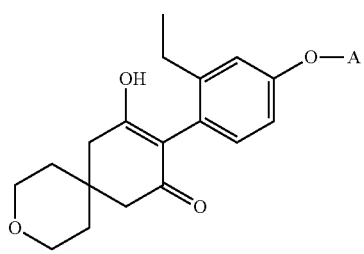

wherein A is as defined in Table 1.

Table 23 covers compounds of the following type

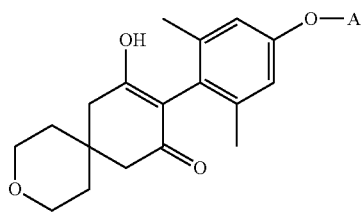

wherein A is as defined in Table 1.

Table 24 covers compounds of the following type

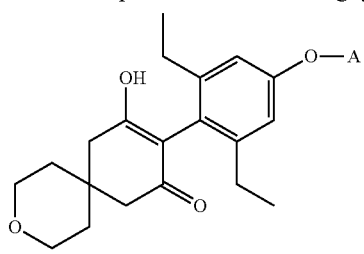

wherein A is as defined in Table 1.

Table 25 covers compounds of the following type

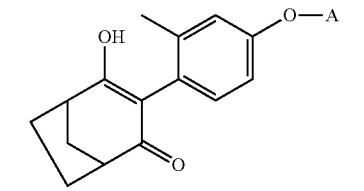

wherein A is as defined in Table 1.

Table 26 covers compounds of the following type

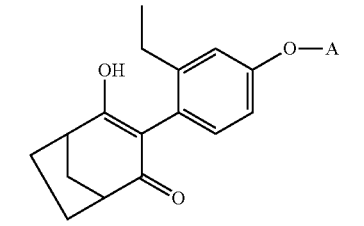

wherein A is as defined in Table 1.

Table 27 covers compounds of the following type

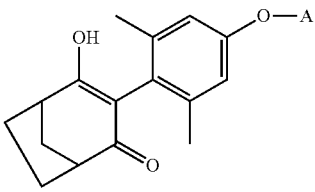

wherein A is as defined in Table 1.

Table 28 covers compounds of the following type

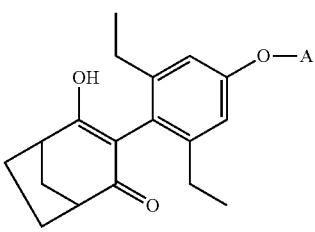

wherein A is as defined in Table 1.

Table 29 covers compounds of the following type

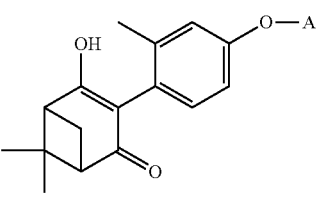

wherein A is as defined in Table 1.

Table 30 covers compounds of the following type

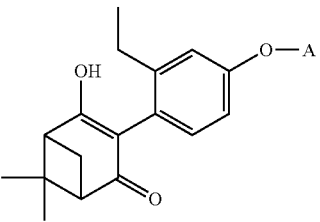

wherein A is as defined in Table 1.

Table 31 covers compounds of the following type

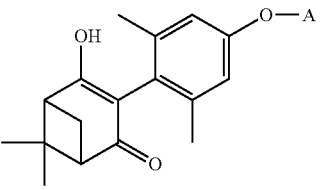

wherein A is as defined in Table 1.

Table 32 covers compounds of the following type

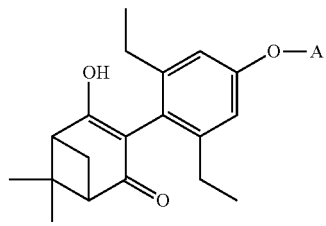

wherein A is as defined in Table 1.

Table 33 covers compounds of the following type

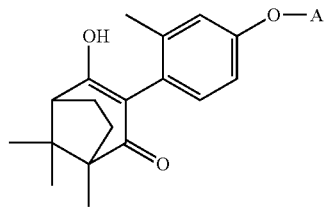

wherein A is as defined in Table 1.

Table 34 covers compounds of the following type

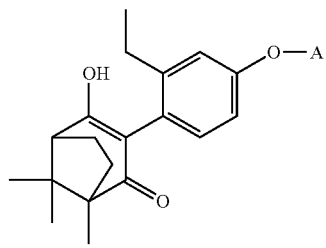

wherein A is as defined in Table 1.

Table 35 covers compounds of the following type

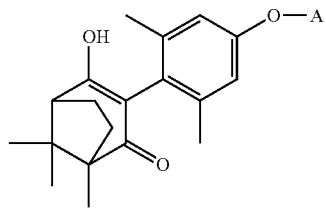

wherein A is as defined in Table 1.

Table 36 covers compounds of the following type

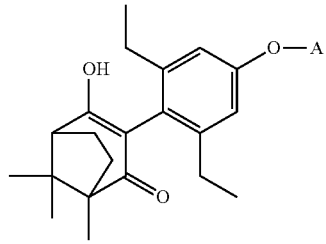

wherein A is as defined in Table 1.

Table 37 covers compounds of the following type

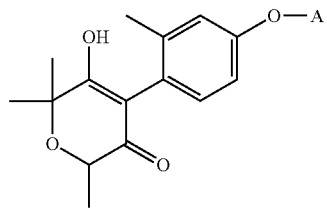

wherein A is as defined in Table 1.

Table 38 covers compounds of the following type

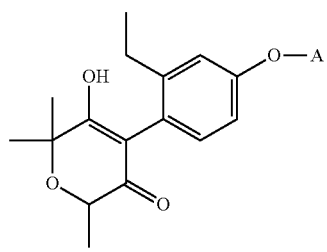

wherein A is as defined in Table 1.

Table 39 covers compounds of the following type

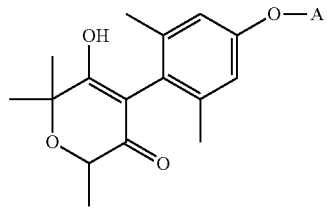

wherein A is as defined in Table 1.

Table 40 covers compounds of the following type

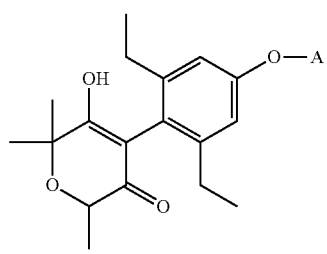

wherein A is as defined in Table 1.

Table 41 covers compounds of the following type

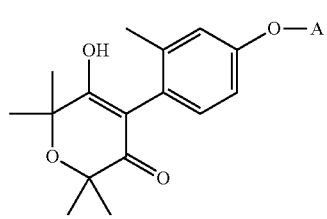

wherein A is as defined in Table 1.

Table 42 covers compounds of the following type

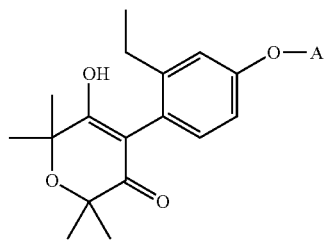

wherein A is as defined in Table 1.

Table 43 covers compounds of the following type

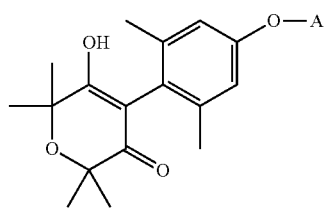

wherein A is as defined in Table 1.

Table 44 covers compounds of the following type

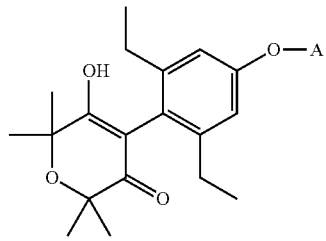

wherein A is as defined in Table 1.

Table 45 covers compounds of the following type

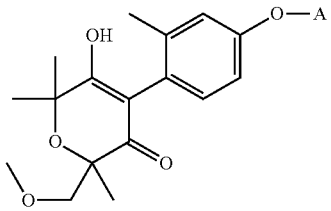

wherein A is as defined in Table 1.

Table 46 covers compounds of the following type

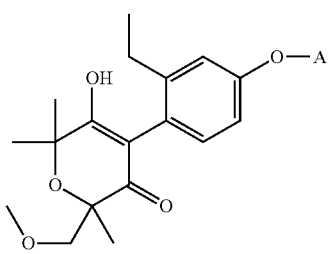

Table 47 covers compounds of the following type

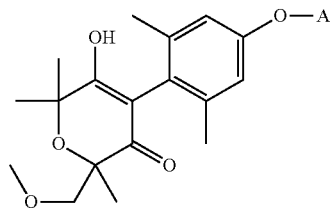

wherein A is as defined in Table 1.

Table 48 covers compounds of the following type

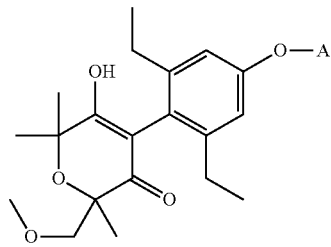

wherein A is as defined in Table 1.

Table 49 covers compounds of the following type

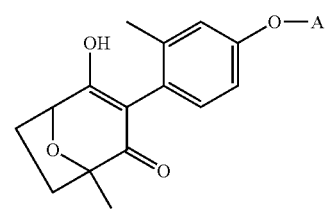

wherein A is as defined in Table 1.

Table 50 covers compounds of the following type

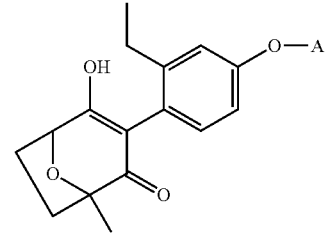

wherein A is as defined in Table 1.

Table 51 covers compounds of the following type

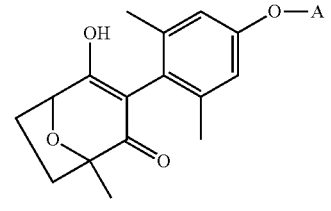

wherein A is as defined in Table 1.

Table 52 covers compounds of the following type

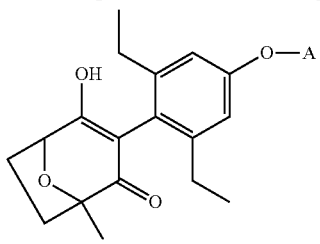

wherein A is as defined in Table 1.

Table 53 covers compounds of the following type

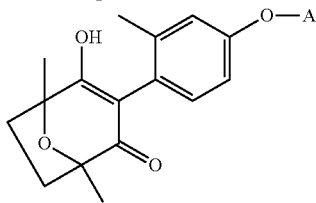

wherein A is as defined in Table 1.

Table 54 covers compounds of the following type

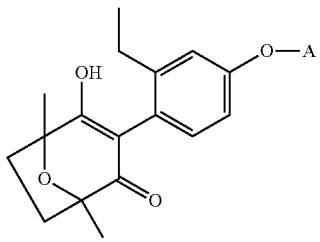

wherein A is as defined in Table 1.

Table 55 covers compounds of the following type

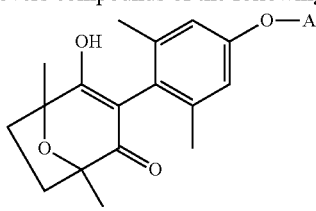

wherein A is as defined in Table 1.

Table 56 covers compounds of the following type

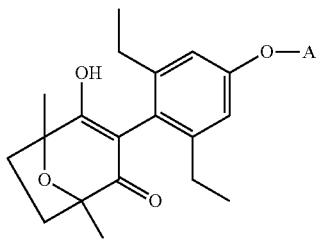

wherein A is as defined in Table 1.

Biological Examples

Seeds of a variety of test species were sown in standard soil in pots. After cultivation for one day (pre-emergence) or after 8 days cultivation (post-emergence) under controlled conditions in a glasshouse (at 24/16° C., day/night; 14 hours light; 65% humidity), the plants were sprayed with an aqueous spray solution derived from the formulation of the technical active ingredient in acetone/water (50:50) solution containing 0.5% Tween 20 (polyoxyethelyene sorbitan monolaurate, CAS RN 9005-64-5). The test plants were then grown in a glasshouse under controlled conditions in a glasshouse (at 24/16° C., day/night; 14 hours light; 65% humidity) and watered twice daily. After 13 days for pre and post-emergence, the test was evaluated (100=total damage to plant; 0=no damage to plant).

Test Plants:

*Lolium perenne* (LOLPE), *Alopecurus myosuroides* (ALOMY), *Echinochloa crus-galli* (ECHCG), and *Avena fatua* (AVEFA).

Pre-Emergence Activity

| Compound Number | Rate g/ha | LOLPE | ALOMY | ECHCG | AVEFA |
|---|---|---|---|---|---|
| A-2 | 250 | 70 | 20 | 50 | 0 |
| A-3 | 250 | 20 | 20 | 20 | 10 |
| A-4 | 250 | 60 | 20 | 60 | 20 |
| A-5 | 250 | 30 | 10 | 40 | 10 |
| A-6 | 250 | 100 | 60 | 100 | 30 |
| A-7 | 250 | 80 | 40 | 60 | 20 |
| A-8 | 250 | 100 | 40 | 100 | 30 |
| A-9 | 250 | 60 | 20 | 30 | 0 |
| A-10 | 250 | 100 | 70 | 100 | 90 |
| A-11 | 250 | 100 | 90 | 100 | 90 |
| A-14 | 250 | 50 | 30 | 20 | 10 |
| A-15 | 250 | 10 | 0 | 90 | 0 |
| A-16 | 250 | 0 | 0 | 0 | 0 |

What is claimed is:

1. A compound of formula I

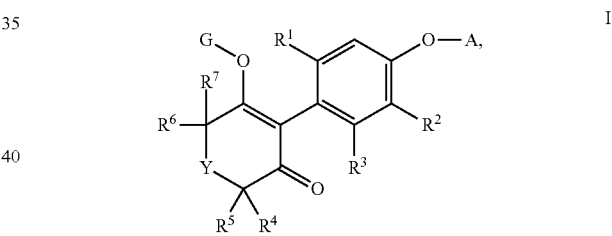

wherein

A is phenyl, naphthyl, a 5- or 6-membered heteroaryl or a bicyclic 8- to 10-membered heteroaryl,
wherein the heteroaryl contains a heteratom selected from nitrogen, oxygen and sulfur, and wherein A is unsubstituted or substituted;

$R^1$ is methyl, ethyl, n-propyl, isopropyl, cyclopropyl, halomethyl, haloethyl, vinyl, propenyl, ethynyl, propynyl, halogen, methoxy, ethoxy, halomethoxy or haloethoxy;

$R^2$ and $R^3$ are independently of each other hydrogen, methyl, ethyl, n-propyl, isopropyl, cyclopropyl, halomethyl, haloethyl, vinyl, propenyl, ethynyl, propynyl, halogen, methoxy, ethoxy, halomethoxy or haloethoxy; and $R^4$, $R^5$, $R^6$ and $R^7$ are independently of each other hydrogen, $C_1$-$C_6$alkyl, $C_1$-$C_6$alkyl substituted by $C_1$-$C_4$alkoxy or halogen, $C_2$-$C_6$ alkenyl, $C_2$-$C_6$ alkenyl substituted by $C_1$-$C_4$alkoxy or halogen, $C_2$-$C_6$alkynyl, $C_2$-$C_6$alkynyl substituted by $C_1$-$C_4$alkoxy or halogen, $C_3$-$C_7$cycloalkyl, $C_3$-$C_7$cycloalkyl substituted by $C_1$-$C_4$alkyl or $C_1$-$C_4$alkoxy, $C_5$-$C_7$cycloalkenyl, $C_5$-$C_7$cycloalkenyl substituted by $C_1$-$C_4$alkyl or $C_1$-$C_4$alkoxy, or heterocyclyl or heterocyclyl substituted by $C_1$-$C_4$alkyl or $C_1$-$C_4$alkoxy; or $R^4$ and $R^5$, or $R^6$ and $R^7$, together with the atoms to which they are bonded, form a 5- to 8-membered spiro-carbocyclyl or spiro-heterocyclyl, which contains one or two heteroatoms selected from nitrogen, oxygen and sulfur; or $R^5$ and $R^6$, together with the atoms to which they are bonded, form a 5- to 8-membered carbocyclyl or heterocyclyl, which contains one or two heteroatoms selected from nitrogen, oxygen and sulfur; and Y is O, S(O)$_n$, C=O, $CR^8R^9$ or $CR^{10}R^{11}CR^{12}R^{13}$;

n is 0, 1 or 2; and $R^8$ and $R^9$ are independently of each other hydrogen, $C_1$-$C_6$alkyl, $C_1$-$C_6$alkyl substituted by $C_1$-$C_4$alkoxy or halogen, $C_2$-$C_6$ alkenyl, $C_2$-$C_6$ alkenyl substituted by $C_1$-$C_4$alkoxy or halogen, $C_2$-$C_6$alkynyl, $C_2$-$C_6$alkynyl substituted by $C_1$-$C_4$alkoxy or halogen, $C_3$-$C_7$cycloalkyl, $C_3$-$C_7$cycloalkyl substituted by $C_1$-$C_4$alkyl or $C_1$-$C_4$alkoxy, $C_5$-$C_7$cycloalkenyl, $C_5$-$C_7$cycloalkenyl substituted by $C_1$-$C_4$alkyl or $C_1$-$C_4$alkoxy, or heterocyclyl or heterocyclyl substituted by $C_1$-$C_4$alkyl or $C_1$-$C_4$alkoxy; or $R^8$ and $R^9$, together with the atoms to which they are bonded, form a 5-to 8-membered spiro-carbocyclyl or spiro-heterocyclyl, which contains one or two heteroatoms selected from nitrogen, oxygen and sulfur; and $R^{10}$, $R^{11}$, $R^{12}$, and $R^{13}$ are independently of each other hydrogen, $C_1$-$C_6$alkyl or $C_1$-$C_6$alkoxy; and G is hydrogen or an agriculturally acceptable metal, sulfonium, ammonium or latentiating group;

and wherein when G is a latentiating group then G is phenyl$C_1$alkyl (wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano or by nitro), heteroaryl$C_1$alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano or by nitro), $C_3$alkenyl, $C_3$haloalkenyl, $C_3$alkynyl, $C(X^a)$—$R^a$, $C(X^b)$—$X^c$—$R^b$, $C(X^d)$—$N(R^c)$—$R^d$, —$SO_2$—$R^e$, —$P(X^e)(R^f)$—$R^g$, or $CH_2$—$X^f$—$R^h$;

wherein $X^a$, $X^b$, $X^b$, $X^d$, $X^e$ and $X^f$ are independently of each other oxygen or sulfur; and $R^a$ is H, $C_1$-$C_{18}$alkyl, $C_2$-$C_{18}$alkenyl, $C_2$-$C_{18}$alkynyl, $C_1$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino($C_1$-$C_5$)alkyl, $C_2$-$C_8$dialkylamino($C_1$-$C_8$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_1$-$C_5$)alkylamino($C_1$-$C_5$)alkyl, $C_3$-$C_6$trialkylsilyl($C_1$-$C_5$)alkyl, phenyl($C_1$-$C_5$)alkyl (wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl($C_1$-$C_5$)alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_5$cycloalkyl; phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro; or heteroaryl or heteroaryl substituted by $C_1$-$C_3$alkyl, $C_1$-$C_3$haloalkyl, $C_1$-$C_3$alkoxy, $C_1$-$C_3$haloalkoxy, halogen, cyano or nitro;

$R^b$ is $C_1$-$C_{18}$alkyl, $C_3$-$C_{18}$alkenyl, $C_3$-$C_{18}$alkynyl, $C_2$-$C_{10}$haloalkyl, $C_1$-$C_{10}$cyanoalkyl, $C_1$-$C_{10}$nitroalkyl, $C_2$-$C_{10}$aminoalkyl, $C_1$-$C_5$alkylamino($C_1$-$C_5$)alkyl, $C_2$-$C_8$dialkylamino($C_1$-$C_8$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_1$-$C_5$)alkylamino($C_1$-$C_5$)alkyl, $C_3$-$C_6$trialkylsilyl($C_1$-$C_5$)alkyl, phenyl($C_1$-$C_5$)alkyl (wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkyl-thio, $C_1$-$C_3$alkylsulfinyl, $C_1$-$C_3$alkylsulfonyl, halogen, cyano, or by nitro), $C_3$-$C_5$haloalkenyl, $C_3$-$C_8$cycloalkyl; phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro; or heteroaryl or heteroaryl substituted by $C_1$-$C_3$ alkyl, $C_1$-$C_3$haloalkyl, $C_1$-$C_3$alkoxy, $C_1$-$C_3$haloalkoxy, halogen, cyano or nitro; and $R^c$ and $R^d$ are each independently of each other hydrogen, $C_1$-$C_{10}$alkyl, $C_3$-$C_{10}$alkenyl, $C_3$-$C_{10}$alkynyl, $C_2$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_2$-$C_5$)alkylaminoalkyl, $C_3$-$C_6$trialkylsilyl($C_1$-$C_5$)alkyl, phenyl($C_1$-$C_5$)alkyl (wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl($C_1$-$C_5$)alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl; phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro; heteroaryl or heteroaryl substituted by $C_1$-$C_3$alkyl, $C_1$-$C_3$haloalkyl, $C_1$-$C_3$alkoxy, $C_1$-$C_3$haloalkoxy, halogen, cyano or nitro; heteroarylamino or heteroarylamino substituted by $C_1$-$C_3$alkyl, $C_1$-$C_3$haloalkyl, $C_1$-$C_3$alkoxy, $C_1$-$C_3$haloalkoxy, halogen, cyano or nitro; diheteroarylamino or diheteroarylamino substituted by $C_1$-$C_3$alkyl, $C_1$-$C_3$haloalkyl, $C_1$-$C_3$alkoxy, $C_1$-$C_3$haloalkoxy, halogen, cyano or nitro; phenylamino or phenylamino substituted by $C_1$-$C_3$alkyl, $C_1$-$C_3$haloalkyl, $C_1$-$C_3$alkoxy, $C_1$-$C_3$haloalkoxy, halogen, cyano or by nitro; diphenylamino or diphenylamino substituted by $C_1$-$C_3$alkyl, $C_1$-$C_3$haloalkyl, $C_1$-$C_3$alkoxy, $C_1$-$C_3$haloalkoxy, halogen, cyano or by nitro; or $C_3$-$C_7$cycloalkylamino, di-$C_3$-$C_7$cycloalkylamino or $C_3$-$C_7$cycloalkoxy;

or $R^c$ and $R^d$ are joined together to form a 3-7 membered ring, wherein the ring optionally contains one heteroatom selected from O or S in addition to the N from the $C(X^d)$—$N(R^c)$—$R^d$ group; and $R^e$ is $C_1$-$C_{10}$alkyl, $C_2$-$C_{10}$alkenyl, $C_2$-$C_{10}$alkynyl, $C_1$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_1$-$C_5$)alkylamino($C_1$-$C_5$)alkyl, $C_3$-$C_6$trialkylsilyl($C_1$-$C_5$)alkyl, phenyl($C_1$-$C_5$)alkyl (wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl($C_1$-$C_5$)alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl; phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro; heteroaryl or heteroaryl substituted by $C_1$-$C_3$alkyl, $C_1$-$C_3$haloalkyl, $C_1$-$C_3$alkoxy, $C_1$-$C_3$haloalkoxy, halogen, cyano or by nitro; heteroarylamino or heteroarylamino substituted by $C_1$-$C_3$ alkyl, $C_1$-$C_3$haloalkyl, $C_1$-$C_3$alkoxy, $C_1$-$C_3$haloalkoxy, halogen, cyano or by nitro; diheteroarylamino or diheteroarylamino substituted by $C_1$-$C_3$alkyl, $C_1$-$C_3$haloalkyl, $C_1$-$C_3$alkoxy, $C_1$-$C_3$haloalkoxy, halogen, cyano or nitro; phenylamino or phenylamino substituted by $C_1$-$C_3$alkyl, $C_1$-$C_3$haloalkyl, $C_1$-$C_3$alkoxy, $C_1$-$C_3$haloalkoxy, halogen, cyano or nitro; diphenylamino or diphenylamino substituted by $C_1$-$C_3$alkyl, $C_1$-$C_3$haloalkyl, $C_1$-$C_3$alkoxy, $C_1$-$C_3$haloalkoxy, halogen, cyano or nitro; or $C_3$-$C_7$cycloalkylamino, di$C_3$-$C_7$cycloalkylamino, $C_3$-$C_7$cycloalkoxy, $C_1$-$C_{10}$alkoxy, $C_1$-$C_{10}$haloalkoxy, $C_1$-$C_5$alkylamino or $C_2$-$C_8$dialkylamino;

$R^f$ and $R^g$ are each independently of each other $C_1$-$C_{10}$alkyl, $C_2$-$C_{10}$alkenyl, $C_2$-$C_{10}$alkynyl, $C_1$-$C_{10}$alkoxy, $C_1$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_1$-$C_5$)alkylamino($C_1$-$C_5$)alkyl, $C_3$-$C_6$trialkylsilyl($C_1$-$C_5$)alkyl, phenyl($C_1$-$C_5$)alkyl (wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano or by nitro), heteroaryl($C_1$-$C_5$)alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano or by nitro), phenoxy($C_1$-$C_5$)alkyl (wherein the phenyl

— alkyl, $C_3$-$C_5$alkenyloxy($C_1$-$C_5$)alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_2$-$C_5$)alkylaminoalkyl, $C_3$-$C_6$trialkylsilyl($C_1$-$C_5$)alkyl, phenyl($C_1$-$C_5$)alkyl (wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl($C_1$-$C_5$)alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl; phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro; heteroaryl or heteroaryl substituted by $C_1$-$C_3$ alkyl, $C_1$-$C_3$haloalkyl, $C_1$-$C_3$alkoxy, $C_1$-$C_3$haloalkoxy, halogen, cyano or by nitro; heteroarylamino or heteroarylamino substituted by $C_1$-$C_3$ alkyl, $C_1$-$C_3$haloalkyl, $C_1$-$C_3$alkoxy, $C_1$-$C_3$haloalkoxy, halogen, cyano or by nitro; diheteroarylamino or diheteroarylamino substituted by $C_1$-$C_3$ alkyl, $C_1$-$C_3$haloalkyl, $C_1$-$C_3$alkoxy, $C_1$-$C_3$haloalkoxy, halogen, cyano or nitro; phenylamino or phenylamino substituted by $C_1$-$C_3$alkyl, $C_1$-$C_3$haloalkyl, $C_1$-$C_3$alkoxy, $C_1$-$C_3$haloalkoxy, halogen, cyano or nitro; diphenylamino or diphenylamino substituted by $C_1$-$C_3$alkyl, $C_1$-$C_3$haloalkyl, $C_1$-$C_3$alkoxy, $C_1$-$C_3$haloalkoxy, halogen, cyano or nitro; or $C_3$-$C_7$cycloalkylamino, di$C_3$-$C_7$cycloalkylamino, $C_3$-$C_7$cycloalkoxy, $C_1$-$C_{10}$haloalkoxy, $C_1$-$C_5$alkylamino or $C_2$-$C_8$dialkylamino; or benzyloxy or phenoxy, wherein the benzyl and phenyl groups may in turn be substituted by $C_1$-$C_3$alkyl, $C_1$-$C_3$haloalkyl, $C_1$-$C_3$alkoxy, $C_1$-$C_3$haloalkoxy, halogen, cyano or nitro; and $R^h$ is $C_1$-$C_{10}$alkyl, $C_3$-$C_{10}$alkenyl, $C_3$-$C_{10}$alkynyl, $C_1$-$C_{10}$haloalkyl, $C_1$-$C_{10}$cyanoalkyl, $C_1$-$C_{10}$nitroalkyl, $C_2$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_1$-$C_5$)alkylamino($C_1$-$C_5$)alkyl, $C_3$-$C_6$trialkylsilyl($C_1$-$C_5$)alkyl, phenyl($C_1$-$C_5$)alkyl (wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano or by nitro), heteroaryl($C_1$-$C_5$)alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano or by nitro), phenoxy($C_1$-$C_5$)alkyl (wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano or by nitro), heteroaryloxy($C_1$-$C_5$)alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano or by nitro), $C_3$-$C_5$haloalkenyl, $C_3$-$C_8$cycloalkyl; phenyl or phenyl substituted by $C_1$-$C_3$alkyl, $C_1$-$C_3$haloalkyl, $C_1$-$C_3$alkoxy, $C_1$-$C_3$haloalkoxy, halogen or by nitro; or heteroaryl or heteroaryl substituted by $C_1$-$C_3$alkyl, $C_1$-$C_3$haloalkyl, $C_1$-$C_3$alkoxy, $C_1$-$C_3$haloalkoxy, halogen, cyano or by nitro;

and wherein:

"aryl" means phenyl or naphthyl; and

"heteroaryl" means an aromatic ring system containing at least one heteroatom and consisting either of a single ring or of two fused rings;

and wherein, when present, the optional substituents on aryl and heteroaryl are selected, independently, from halogen, nitro, cyano, rhodano, isothiocyanato, $C_1$-$C_6$alkyl, $C_1$-$C_6$haloalkyl, $C_1$-$C_6$alkoxy($C_1$-$C_6$)alkyl, $C_2$-$C_6$alkenyl, $C_2$-$C_6$haloalkenyl, $C_2$-$C_6$alkynyl, $C_3$-$C_7$cycloalkyl (optionally substituted with $C_1$-$C_6$alkyl or halogen), $C_5$-$C_7$cycloalkenyl (optionally substituted with $C_1$-$C_6$alkyl or halogen), hydroxy, $C_1$-$C_{10}$alkoxy, $C_1$-$C_{10}$alkoxy($C_1$-$C_{10}$)alkoxy, tri($C_1$-$C_4$)alkylsilyl($C_1$-$C_6$)alkoxy, $C_1$-$C_6$alkoxycarbonyl($C_1$-$C_{10}$)alkoxy, $C_1$-$C_{10}$haloalkoxy, aryl($C_1$-$C_4$)alkoxy (where the aryl group is optionally substituted with halogen or $C_1$-$C_6$alkyl), $C_3$-$C_7$cycloalkyloxy (where the cycloalkyl group is optionally substituted with $C_1$-$C_6$alkyl or halogen), $C_3$-$C_{10}$alkenyloxy, $C_3$-$C_{10}$alkynyloxy, mercapto, $C_1$-$C_{10}$alkylthio, $C_1$-$C_{10}$haloalkylthio, aryl($C_1$-$C_4$)alkylthio, $C_3$-$C_7$cycloalkylthio (where the cycloalkyl group is optionally substituted with $C_1$-$C_6$alkyl or halogen), tri($C_1$-$C_4$)-alkylsilyl($C_1$-$C_6$)alkylthio, arylthio, $C_1$-$C_6$alkylsulfonyl, $C_1$-$C_6$haloalkylsulfonyl, $C_1$-$C_6$alkylsulfinyl, $C_1$-$C_6$haloalkylsulfinyl, arylsulfonyl, tri($C_1$-$C_4$)alkylsilyl, aryldi($C_1$-$C_4$)alkylsilyl, $C_1$-$C_4$alkyldiarylsilyl, triarylsilyl, $C_1$-$C_{10}$alkylcarbonyl, $HO_2C$, $C_1$-$C_{10}$alkoxycarbonyl, aminocarbonyl, $C_1$-$C_6$alkylaminocarbonyl, di($C_1$-$C_6$alkyl)-aminocarbonyl, N—($C_1$-$C_3$ alkyl)-N—($C_1$-$C_3$alkoxy)aminocarbonyl, $C_1$-$C_6$alkylcarbonyloxy, arylcarbonyloxy, di($C_1$-$C_6$)alkylaminocarbonyloxy, aryl (optionally substituted with $C_1$-$C_6$alkyl or halogen), heteroaryl (optionally substituted with $C_1$-$C_6$alkyl or halogen), heterocyclyl (optionally substituted with $C_1$-$C_6$alkyl or halogen), aryloxy (where the aryl group is optionally substituted with $C_1$-$C_6$alkyl or halogen), heteroaryloxy (where the heteroaryl group is optionally substituted with $C_1$-$C_6$alkyl or halogen), heterocyclyloxy (where the heterocyclyl group is optionally substituted with $C_1$-$C_6$alkyl or halogen), amino, $C_1$-$C_6$alkylamino, di($C_1$-$C_6$)alkylamino, $C_1$-$C_6$alkylcarbonylamino, N—($C_1$-$C_6$)alkylcarbonyl-N—($C_1$-$C_6$)alkylamino, and arylcarbonyl (where the aryl group is optionally substituted with halogen or $C_1$-$C_6$alkyl);

or two adjacent positions on an aryl or heteroaryl system are cyclised to form a 5, 6 or 7 membered carbocyclic or heterocyclic ring, optionally substituted with halogen or $C_1$-$C_6$alkyl.

2. The compound according to claim 1, wherein A is substituted by halogen, $C_1$-$C_4$alkyl, $C_1$-$C_4$haloalkyl, $C_2$-$C_4$alkenyl, $C_2$-$C_4$haloalkenyl, $C_2$-$C_4$alkynyl, $C_1$-$C_4$alkoxy, $C_1$-$C_4$haloalkoxy, $C_1$-$C_4$alkylthio, $C_1$-$C_4$alkylsulfinyl, $C_1$-$C_4$alkylsulfonyl, $C_1$-$C_4$haloalkylthio, $C_1$-$C_4$haloalkylsulfinyl, $C_1$-$C_4$haloalkylsulfonyl, nitro, cyano, $C_3$-$C_6$cycloalkyl, $C_1$-$C_3$alkylcarbonyl, $C_1$-$C_4$alkoxycarbonyl, aminocarbonyl, $C_1$-$C_3$alkylaminocarbonyl, di-$C_1$-$C_3$alkylaminocarbonyl, $C_1$-$C_3$alkylaminocarbonyloxy, di-$C_1$-$C_3$alkylaminocarbonyloxy, aminothiocarbonyl, $C_1$-$C_3$alkylaminothiocarbonyl, di$C_1$-$C_3$alkylaminothiocarbonyl, $C_1$-$C_4$alkylcarbonylamino, $C_3$-$C_6$cycloalkylcarbonylamino, $C_1$-$C_4$alkoxycarbonylamino,$C_1$-$C_4$alkylthiocarbonylamino, $C_1$-$C_3$alkoxy$C_1$-$C_3$alkyl, $C_1$-$C_6$alkylthio$C_1$-$C_6$alkyl, $C_1$-$C_6$alkylsulfinyl$C_1$-$C_6$alkyl, $C_1$-$C_6$alkylsulfonyl$C_1$-$C_6$alkyl, $C_1$-$C_3$alkylsulfonyloxy, $C_1$-$C_3$haloalkylsulfonyloxy or di$C_1$-$C_6$alkylaminosulfonyl, or 2 substituents on adjacent carbon atoms of A together form a $C_3$-$C_4$alkylene, wherein 1 or 2 methylene groups are optionally substituted by halogen, or wherein 1 or 2 of these methylene groups are replaced by oxygen.

3. The compound according to claim 2, wherein A is phenyl, naphthyl, pyridyl, pyrazinyl, pyrimidinyl, pyridazinyl, benzothiazolyl, benzoxazolyl, cinnolinyl, quinolinyl, quinazolinyl, quinoxalinyl or benzotriazinyl, in each case substituted by halogen, methyl, ethyl, trifluoromethyl, methoxy, difluoromethoxy, trifluoromethoxy, nitro or cyano.

4. The compound according to claim 1, wherein $R^1$ is methyl, ethyl, n-propyl, cyclopropyl, halogen, halomethoxy or haloethoxy.

5. The compound according to claim 1, wherein $R^1$ is methyl or ethyl.

6. The compound according to claim 1, wherein $R^2$ is hydrogen, methyl or halogen.

7. The compound according to claim 6, wherein $R^2$ is hydrogen.

8. The compound according to claim 1, wherein $R^3$ is hydrogen, methyl, ethyl, n-propyl, cyclopropyl, halogen, halomethoxy or haloethoxy.

9. The compound according to claim 8, wherein $R^3$ is hydrogen, methyl or ethyl.

10. The compound according to claim 1, wherein $R^4$, $R^5$, $R^6$ and $R^7$ are independently of each other hydrogen or $C_1$-$C_6$alkyl, or $R^4$ and $R^5$, or $R^6$ and $R^7$, together with the atoms to which they are bonded form a spiro-tetrahydropyranyl or a spiro-tetrahydrofuranyl, or $R^5$ and $R^6$ together with the atoms to which they are bonded form a 6- or 7-membered carbocyclyl.

11. The compound according to claim 1, wherein Y is O or $CR^8R^9$, wherein $R^8$ and $R^9$ are as defined in claim 1.

12. The compound according to claim 1, wherein $R^8$ and $R^9$ are independently of each other hydrogen or methyl, or $R^8$ and $R^9$ together with the atoms to which they are bonded form a spiro-tetrahydropyranyl or a spiro-tetrahydrofuranyl.

13. The compound according to claim 1, wherein G is hydrogen or a group —C($X^a$)—$R^a$ or —C($X^b$) —$X^c$—$R^b$ wherein the meanings of $X^a$, $R^a$, $X^b$, $X^c$ and $R^b$ are as defined in claim 1.

14. The compound according to claim 13, wherein G is hydrogen.

15. The compound according to claim 1, wherein:

"aryl" means phenyl, and

"heterocyclyl" means a non-aromatic monocyclic or bicyclic ring system containing up to 7 atoms including one or two heteroatoms selected from O, S and N.

16. The compound according to claim 1, wherein A is phenyl, naphthyl, pyridyl, pyrazinyl, pyrimidinyl, pyridazinyl, benzothiazolyl, benzoxazolyl, cinnolinyl, quinolinyl, quinazolinyl, quinoxalinyl or benzotriazinyl, in each case substituted by halogen, methyl, trifluoromethyl, nitro or cyano, $R^1$ is ethyl, $R^2$ and $R^3$ are hydrogen, $R^4$ to $R^7$ are hydrogen or methyl or $R^5$ and $R^6$, together with the atoms to which they are bonded, form a 6- or 7-membered carbocyclyl, Y is O or $CR^8R^9$, wherein $R^8$ and $R^9$ are independently of each other hydrogen or methyl, or $R^8$ and $R^9$ together with the atoms to which they are bonded form a spiro-tetrahydropyranyl or a spiro-tetrahydrofuranyl, and G is hydrogen.

17. A process for the preparation of a compound of formula I according to claim 1, wherein G is hydrogen, which comprises the reaction of a compound of formula (K)

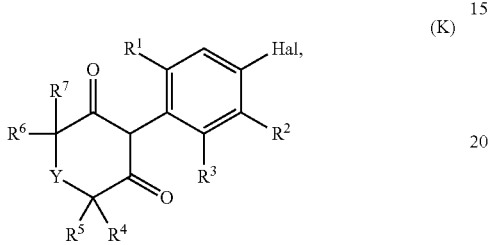

wherein Y and $R^1$ to $R^7$ are as defined in claim 1 and Hal is bromine or iodine, with a compound A-OH, wherein A is as defined in claim 1, in the presence of a catalyst, a ligand or additive, and a base, in a solvent.

18. A process for the preparation of a compound of formula I according to claim 1, wherein G is hydrogen, which comprises the reaction of a compound of formula (M)

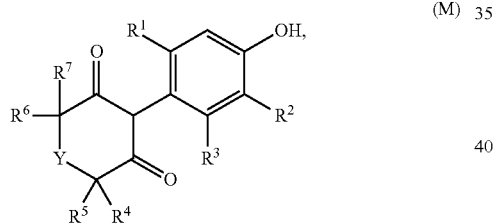

wherein Y and $R^1$ to $R^7$ are as defined in claim 1, with a compound A-Hal, wherein A is as defined in claim 1 and Hal is fluorine, chlorine, bromine or iodine, in the presence or absence of a catalyst and ligand, and in the presence of a base, and in a solvent.

19. A herbicidal composition, which, in addition to comprising formulation adjuvants, comprises a herbicidally effective amount of a compound of formula I as defined in claim 1.

20. A method of controlling grasses in crops of useful plants, which comprises applying a herbicidally effective amount of a compound of formula I as defined in claim 1, or of a composition comprising such a compound, to the plants or to the locus thereof.

21. A method according to claim 20, which comprises applying a herbicidally effective amount of the composition comprising the compound to the plants or to the locus thereof, and wherein the crops of useful plants are wheat, barley, rice, corn, rape, sugarbeet, sugarcane, soybean, cotton, sunflower, or peanut.

22. A mixture of a compound of formula I, as defined in claim 1, in combination with a further herbicide, wherein the mixture of the compound of formula I is selected from:

compound of formula I+acetochlor, compound of formula I+acifluorfen, compound of formula I+acifluorfen-sodium, compound of formula I+aclonifen, compound of formula I+acrolein, compound of formula I+alachlor, compound of formula I+alloxydim, compound of formula I+allyl alcohol, compound of formula I+ametryn, compound of formula I+amicarbazone, compound of formula I+amidosulfuron, compound of formula I+aminopyralid, compound of formula I+amitrole, compound of formula I+ammonium sulfamate, compound of formula I+anilofos, compound of formula I+asulam, compound of formula I+atraton, compound of formula I+atrazine, compound of formula I+azimsulfuron, compound of formula I+BCPC, compound of formula I+beflubutamid, compound of formula I+benazolin, compound of formula I+benfluralin, compound of formula I+benfuresate, compound of formula I+bensulfuron, compound of formula I+bensulfuron-methyl, compound of formula I+bensulide, compound of formula I+bentazone, compound of formula I+benzfendizone, compound of formula I+benzobicyclon, compound of formula I+benzofenap, compound of formula I+bifenox, compound of formula I+bilanafos, compound of formula I+bispyribac, compound of formula I+bispyribac-sodium, compound of formula I+borax, compound of formula I+bromacil, compound of formula I+bromobutide, compound of formula I+bromoxynil, compound of formula I+butachlor, compound of formula I+butafenacil, compound of formula I+butamifos, compound of formula I+butralin, compound of formula I+butroxydim, compound of formula I+butylate, compound of formula I+cacodylic acid, compound of formula I+calcium chlorate, compound of formula I+cafenstrole, compound of formula I+carbetamide, compound of formula I+carfentrazone, compound of formula I+carfentrazone-ethyl, compound of formula I+CDEA, compound of formula I+CEPC, compound of formula I+chlorflurenol, compound of formula I+chlorflurenol-methyl, compound of formula I+chloridazon, compound of formula I+chlorimuron, compound of formula I+chlorimuron-ethyl, compound of formula I+chloroacetic acid, compound of formula I+chlorotoluron, compound of formula I+chlorpropham, compound of formula I+chlorsulfuron, compound of formula I+chlorthal, compound of formula I+chlorthal-dimethyl, compound of formula I+cinidon-ethyl, compound of formula I+cinmethylin, compound of formula I+cinosulfuron, compound of formula I+cisanilide, compound of formula I+clethodim, compound of formula I+clodinafop, compound of formula I+clodinafop-propargyl, compound of formula I+clomazone, compound of formula I+clomeprop, compound of formula I+clopyralid, compound of formula I+cloransulam, compound of formula I+cloransulam-methyl, compound of formula I+CMA, compound of formula I+4-CPB, compound of formula I+CPMF, compound of formula I+4-CPP, compound of formula I+CPPC, compound of formula I+cresol, compound of formula I+cumyluron, compound of formula I+cyanamide, compound of formula I+cyanazine, compound of formula I+cycloate, compound of formula I+cyclosulfamuron, compound of formula I+cycloxydim, compound of formula I+cyhalofop, compound of formula I+cyhalofop-butyl, compound of formula I+2,4-D, compound of formula I+3,4-DA, compound of formula I+daimuron, compound of formula I+dalapon, compound of formula I+dazomet, compound of formula I+2,4-DB, compound of formula I+3,4-DB, compound of formula I+2,4-DEB, compound of formula I+desmedipham, compound of formula I+dicamba, compound of formula I+dichlobenil, compound of formula I+ortho-ichlorobenzene, compound of formula I+para-dichlorobenzene, compound of formula I+dichlorprop, compound of formula I+dichlorprop-P, compound of formula I+diclofop, compound of formula I+diclofop-methyl, compound of formula I+diclosulam, compound of formula I+difenzoquat, compound of formula I+difenzoquat metilsulfate, compound of formula I+diflufenican, compound of formula I+diflufenzopyr, compound of formula I+dimefuron, compound of formula I+dimepiperate, compound of formula I +dimethachlor, compound of formula I+dimethametryn, compound of formula I+dimethenamid, compound of formula I+dimethenamid-P, compound of formula I+dimethipin, compound of formula I+dimethylarsinic acid, compound of formula I+dinitramine, compound of formula I+dinoterb, compound of formula I+diphenamid, compound of formula I+diquat, compound of formula I+diquat dibromide, compound of formula I+dithiopyr, compound of formula I+diuron, compound of formula I+DNOC, compound of formula I+3,4-DP, compound of formula I+DSMA, compound of formula I+EBEP, compound of formula I+endothal, compound of formula I+EPTC, compound of formula I+esprocarb, compound of formula I+ethalfluralin, compound of formula I+ethametsulfuron, compound of formula I+ethametsulfuron-methyl, compound of formula I+ethofumesate, compound of formula I+ethoxyfen, compound of formula I+ethoxysulfuron, compound of formula I+etobenzanid, compound of formula I+fenoxaprop-P, compound of formula I+fenoxaprop-P-ethyl, compound of formula I+fentrazamide, compound of formula I+ferrous sulfate, compound of formula I+flamprop-M, compound of formula I+flazasulfuron, compound of formula I+florasulam, compound of formula I+fluazifop, compound of formula I+fluazifop-butyl, compound of formula I+fluazifop-P, compound of formula I+fluazifop-P-butyl, compound of formula I+flucarbazone, compound of formula I+flucarbazone-sodium, compound of formula I+flucetosulfuron, compound of formula I+fluchloralin, compound of formula I+flufenacet, compound of formula I+flufenpyr, compound of formula I+flufenpyr-ethyl, compound of formula I+flumetsulam, compound of formula I+flumiclorac, compound of formula I+flumiclorac-pentyl, compound of formula I+flumioxazin, compound of formula I+fluometuron, compound of formula I+fluoroglycofen, compound of formula I+fluoroglycofen-ethyl, compound of formula I+flupropanate, compound of formula I+flupyrsulfuron, compound of formula I+flupyrsulfuron-methyl-sodium, compound of formula I+flurenol, compound of formula I+fluridone, compound of formula I+flurochloridone, compound of formula I+fluroxypyr, compound of formula I+flurtamone, compound of formula I+fluthiacet, compound of formula I+fluthiacet-methyl, compound of formula I+fomesafen, compound of formula I+foramsulfuron, compound of formula I+fosamine, compound of formula I+glufosinate, compound of formula I+glufosinate-ammonium, compound of formula I+glyphosate, compound of formula I+halosulfuron, compound of formula I+halosulfuron-methyl, compound of formula I+haloxyfop, compound of formula I+haloxyfop-P, compound of formula I+HC-252, compound of formula I+hexazinone, compound of formula I+imazamethabenz, compound of formula I+imazamethabenz-methyl, compound of formula I+imazamox, compound of formula I+imazapic, compound of formula I+imazapyr, compound of formula I+imazaquin, compound of formula I+imazethapyr, compound of formula I+imazosulfuron, compound of formula I +indanofan, compound of formula I+iodomethane, compound of formula I+iodosulfuron, compound of formula I+iodosulfuron-methyl-sodium, compound of formula I+ioxynil, compound of formula I+isoproturon, compound of formula I+isouron, compound of formula I+isoxaben, compound of formula I+isoxachlortole, compound of formula I+isoxaflutole, compound of formula I+karbutilate, compound of formula I+lactofen, compound of formula I+lenacil, compound of formula I+linuron, compound of formula I+MAA, compound of formula I+MAMA, compound of formula I+MCPA, compound of formula I+MCPA-thioethyl, compound of formula I+MCPB, compound of formula I+mecoprop, compound of formula I+mecoprop-P, compound of formula I+mefenacet, compound of formula I+mefluidide, compound of formula I+mesosulfuron, compound of formula I+mesosulfuron-methyl, compound of formula I+mesotrione, compound of formula I+metam, compound of formula I+metamifop, compound of formula I+metamitron, compound of formula I+metazachlor, compound of formula I+methabenzthiazuron, compound of formula I+methylarsonic acid, compound of formula I+methyldymron, compound of formula I+methyl isothiocyanate, compound of formula I+metobenzuron, compound of formula I+metolachlor, compound of formula I+S-metolachlor, compound of formula I+metosulam, compound of formula I+metoxuron, compound of formula I+metribuzin, compound of formula I+metsulfuron, compound of formula I+metsulfuron-methyl, compound of formula I+MK-616, compound of formula I+molinate, compound of formula I+monolinuron, compound of formula I+naproanilide, compound of formula I+napropamide, compound of formula I+naptalam, compound of formula I+neburon, compound of formula I+nicosulfuron, compound of formula I+nonanoic acid, compound of formula I+norflurazon, compound of formula I+oleic acid (fatty acids), compound of formula I+orbencarb, compound of formula I+orthosulfamuron, compound of formula I+oryzalin, compound of formula I+oxadiargyl, compound of formula I+oxadiazon, compound of formula I+oxasulfuron, compound of formula I+oxaziclomefone, compound of formula I+oxyfluorfen, compound of formula I+paraquat, compound of formula I+paraquat dichloride, compound of formula I+pebulate, compound of formula I+pendimethalin, compound of formula I+penoxsulam, compound of formula I+pentachlorophenol, compound of formula I+pentanochlor, compound of formula I+pentoxazone, compound of formula I+pethoxamid, compound of formula I+petrolium oils, compound of formula I+phenmedipham, compound of formula I+phenmedipham-ethyl, compound of formula I+picloram, compound of formula I+picolinafen, compound of formula I+pinoxaden, compound of formula I+piperophos, compound of formula I+potassium arsenite, compound of formula I+potassium azide, compound of formula I+pretilachlor, compound of formula I+primisulfuron, compound of formula I+primisulfuron-methyl, compound of formula I+prodiamine, compound of formula I+profluazol, compound of formula I+profoxydim, compound of formula I+prometon, compound of formula I+prometryn, compound of formula I+propachlor, compound of formula I+propanil, compound of formula I+propaquizafop, compound of formula I+propazine, compound of formula I+propham, compound of formula I+propisochlor, compound of formula I+propoxycarbazone, compound of formula I+propoxycarbazone-sodium, compound of formula I+propyzamide, compound of formula I+prosulfocarb, compound of formula I+prosulfuron, compound of formula I+pyraclonil, compound of formula I+pyraflufen, compound of formula I+pyraflufen-ethyl, compound of formula I+pyrazolynate, compound of formula I+pyrazosulfuron, compound of formula I+pyrazosulfuron-ethyl, compound of formula I+pyrazoxyfen, compound of formula I+pyribenzoxim, compound of formula I+pyributicarb, compound of formula I+pyridafol, compound of formula I+pyridate, compound of formula I+pyriftalid, compound of formula I+pyriminobac, compound of formula I+pyriminobac-methyl, compound of formula I+pyrimisulfan, compound of formula I+pyrithiobac, compound of formula I+pyrithiobac-sodium, compound of formula I+quinclorac, compound of formula I+quinmerac, compound of formula I+quinoclamine, compound of formula I+quizalofop, compound of formula I+quizalofop-P, compound of formula I+rimsulfuron, compound of formula I+sethoxydim, compound of formula I+siduron, compound of formula I+simazine, compound of formula I+simetryn, compound of formula I+SMA, compound of formula I+sodium arsenite, compound of formula I+sodium azide, compound of formula I+sodium chlorate, compound of formula I+sulcotrione, compound of formula I+sulfentrazone, compound of formula I+sulfometuron, compound of formula I+sulfometuron-methyl, compound of formula I+sulfosate, compound of formula I+sulfosulfuron, compound of formula I+sulfuric acid, compound of formula I+tar oils, compound of formula I+2,3,6-TBA, compound of formula I+TCA, compound of formula I+TCA-sodium, compound of formula I+tebuthiuron, compound of formula I+tepraloxydim, compound of formula I+terbacil, compound of formula I+terbumeton, compound of formula I+terbuthylazine, compound of formula I+terbutryn, compound of formula I+thenylchlor, compound of formula I+thiazopyr, compound of formula I+thifensulfuron, compound of formula I+thifensulfuron-methyl, compound of formula I+thiobencarb, compound of formula I+tiocarbazil, compound of formula I+topramezone, compound of formula I+tralkoxydim, compound of formula I+tri-allate, compound of formula I+triasulfuron, compound of formula I+triaziflam, compound of formula I+tribenuron, compound of formula I+tribenuron-methyl, compound of formula I+tricamba, compound of formula I+triclopyr, compound of formula I+trietazine, compound of formula I+trifloxysulfuron, compound of formula I+trifloxysulfuron-sodium, compound of formula I+trifluralin, compound of formula I+triflusulfuron, compound of formula I+triflusulfuron-methyl, compound of formula I+trihydroxytriazine, compound of formula I+tritosulfuron, compound of formula I+[3-[2-chloro-4-fluoro-5-(1-methyl-6-trifluoromethyl-2,4-dioxo-1,2,3,4-tetrahydropyrimidin-3-yl)phenoxy]-2-pyridyloxy]acetic acid ethyl ester, compound of formula I+4-[(4,5-dihydro-3-methoxy-4-methyl-5-oxo)-1H-1,2,4-triazol-1-ylcarbonylsulfamoyl]-5-methylthiophene-3-carboxylic acid, compound of formula I+BAY747 as defined in Chemical Abstracts Service Registry Number 335104-84-2, compound of formula I+topramezone, compound of formula I+4-hydroxy-3-[[2-[(2-methoxyethoxy)methyl]-6-(trifluoromethyl)-3-pyridinyl]carbonyl]-bicyclo[3.2.1]oct-3-en-2-one, and compound of formula I+4-hydroxy-3-[[2-(3-methoxypropyl)-6-(difluoromethyl)-3-pyridinyl]carbonyl]-bicyclo[3.2.1]oct-3-en-2-one;
and wherein the further herbicide mixed with the compound of formula I is optionally in the form of an ester or a salt.

* * * * *